US007939526B2

(12) United States Patent
Radmer et al.

(10) Patent No.: US 7,939,526 B2
(45) Date of Patent: May 10, 2011

(54) SULFONE SUBSTITUTED IMIDAZO RING ETHERS

(75) Inventors: Matthew R. Radmer, Robbinsdale, MN (US); William H. Moser, St. Paul, MN (US); Joan T. Moseman, Lake Elmo, MN (US); Joseph F. Dellaria, Jr., Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1375 days.

(21) Appl. No.: 10/596,117

(22) PCT Filed: Dec. 3, 2004

(86) PCT No.: PCT/US2004/040383
§ 371 (c)(1),
(2), (4) Date: May 31, 2006

(87) PCT Pub. No.: WO2005/076783
PCT Pub. Date: Aug. 25, 2005

(65) Prior Publication Data
US 2007/0155767 A1    Jul. 5, 2007

Related U.S. Application Data

(60) Provisional application No. 60/526,772, filed on Dec. 4, 2003.

(51) Int. Cl.
*A61K 31/04* (2006.01)
*C07D 215/38* (2006.01)
(52) U.S. Cl. ..................... 514/229.8; 546/82
(58) Field of Classification Search .............. 546/82; 514/229.8
See application file for complete search history.

(56) References Cited

U.S. PATENT DOCUMENTS

| | | |
|---|---|---|
| 3,314,941 A | 4/1967 | Littell at al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |

(Continued)

FOREIGN PATENT DOCUMENTS

EP              0 394 026           10/1990

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983. Brennan at al., "Automated Bioassay of Interferons in Micro-test Plates.", *Biotechniques*, Jun./Jul., 78, 1983.
Testerman et al., "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem*, 15, pp. 1278-1284 (1950).
Jain et al., "Chemical and Pharmacological Investigations of Some ω-Substituted Alkylamino-3-aminopyridines.", *J. Med. Chem.*, 11, pp. 87-92 (1968).
Baranov et al., "Pyrazoles, Imidazoles, and Other 5-Membered Rings.", *Chem. Abs.* 85, 94362, (1976).

(Continued)

*Primary Examiner* — D. Margaret Seaman

(57) ABSTRACT

Imidazo ring compounds (e.g., imidazoquinolines, 6,7,8,9-tetrahydroimidazoquinolines, imidazonaphthyridines, and 6,7,8,9-tetrahydroimidazonaphthyridines) with a sulfide-, sulfinyl-, or sulfonyl-containing ether substituent at the 1-position, pharmaceutical compositions containing the compounds, intermediates, methods of making the compounds, and methods of use of these compounds as immunomodulators, for inducing cytokine biosynthesis in animals and in the treatment of diseases including viral and neoplastic diseases, are disclosed.

39 Claims, No Drawings

U.S. PATENT DOCUMENTS

| | | |
|---|---|---|
| 6,696,465 B2 | 2/2004 | Dellaria et al. |
| 6,706,728 B2 | 3/2004 | Hedenstrom et al. |
| 6,743,920 B2 | 6/2004 | Lindstrom et al. |
| 6,756,382 B2 | 6/2004 | Rice et al. |
| 6,797,718 B2 | 9/2004 | Dellaria et al. |
| 6,818,650 B2 | 11/2004 | Griesgraber |
| 6,841,678 B2 | 1/2005 | Merli et al. |
| 6,852,861 B2 | 2/2005 | Merli et al. |
| 7,091,214 B2 * | 8/2006 | Hays et al. .................... 514/293 |
| 7,226,928 B2 * | 6/2007 | Mitra et al. .................... 514/293 |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2003/0096835 A1 | 5/2003 | Crooks et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0144286 A1 | 7/2003 | Frenkel et al. |
| 2003/0161797 A1 | 8/2003 | Miller et al. |
| 2003/0199538 A1 | 10/2003 | Skwierczynski et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2005/0054590 A1 | 3/2005 | Averett |
| 2005/0085500 A1 | 4/2005 | Gutman et al. |
| 2005/0165236 A1 | 7/2005 | Colombo et al. |
| 2005/0245562 A1 | 11/2005 | Garcia-Echeverria et al. |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO 2006/065280 | 6/2006 |
| WO | WO 2006/074003 | 7/2006 |
| WO | WO 2006/004737 | 8/2006 |
| WO | WO 2006/083400 | 8/2006 |
| WO | WO 2006/083440 | 8/2006 |
| WO | WO 2006/086449 | 8/2006 |
| WO | WO 2006/086633 | 8/2006 |
| WO | WO 2006/091567 | 8/2006 |
| WO | WO 2006/091568 | 8/2006 |
| WO | WO 2006/091647 | 8/2006 |

OTHER PUBLICATIONS

Chollet et al., "Development of a Topically Active Imiquimod Formulation.", *Pharmaceutical Development and Technology*, 4(1), pp. 35-43 (1999).

Berènyi et al., "Ring Transformation of Condensed Dihydro-astriazines.", *J. Heterocyclic Chem.*, 18, pp. 1537-1540 (1981).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

* cited by examiner

SULFONE SUBSTITUTED IMIDAZO RING ETHERS

RELATED APPLICATIONS

This application is the National Stage of International Application No. PCT/US2004/040383, filed Dec. 3, 2004, which claims priority to U.S. Provisional Application Ser. No. 60/526,772, filed Dec. 4, 2003, which is incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

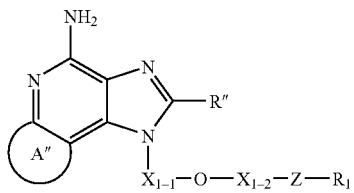

and, more particularly, compounds of the following Formula Ia:

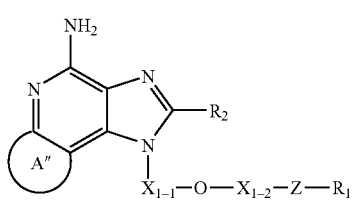

wherein A", R", $R_1$, $R_2$, $X_{1-1}$, $X_{1-2}$, and Z are as defined below.

The compounds of Formulas I and Ia are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I or Formula Ia and methods of inducing cytokine biosynthesis in an animal, treating a viral infection and/or treating a neoplastic disease in an animal by administering an effective amount of a compound of Formula I to the animal.

In addition, methods of synthesizing compounds of Formula I and Formula Ia and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through IVa:

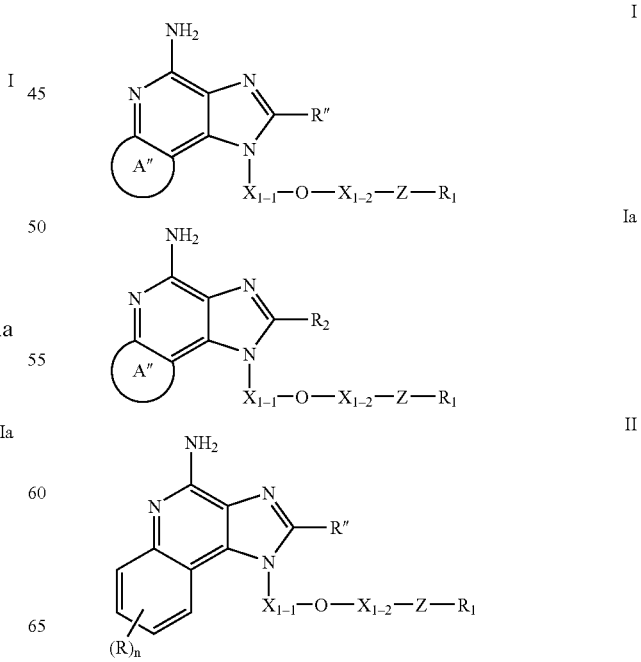

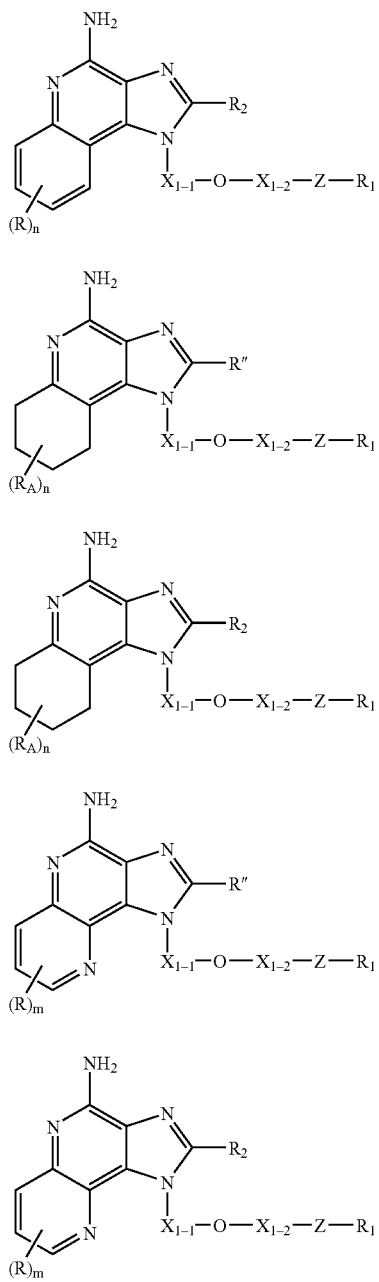
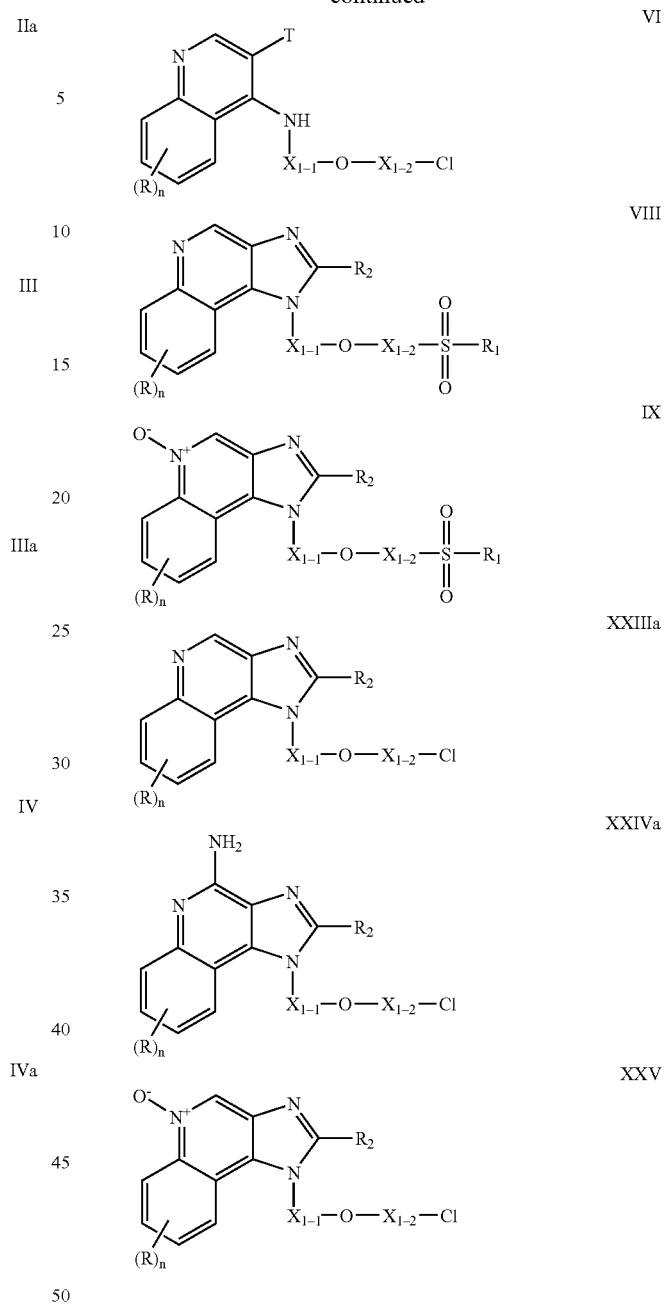
as well as intermediates of the following Formulas V, VI, VIII, IX, XXIIIa, XXIVA, and XXV:
wherein A″, R″, $R_1$, $R_2$, R, $R_A$, T, $X_{1-1}$, $X_{1-2}$, Z, m, and n are as defined below.
In one embodiment, the present invention provides a compound of Formula I:
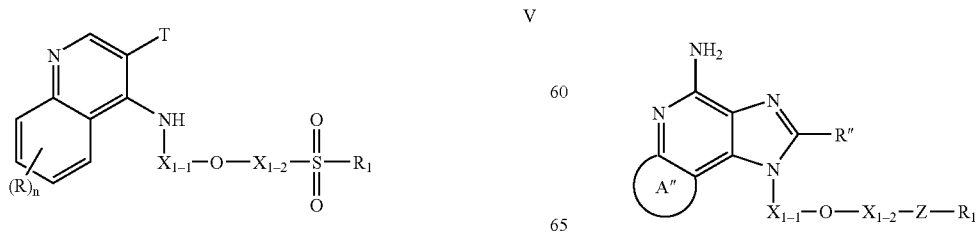

wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

A" is a fused aryl ring or heteroaryl ring containing one heteroatom selected from the group consisting of N and S, wherein the aryl or heteroaryl ring is unsubstituted or substituted by one or more R groups, or a fused 5 to 7 membered saturated ring, optionally containing one heteroatom selected from the group consisting of N and S, and unsubstituted or substituted by one or more $R_A$ groups;

each R is independently selected from the group consisting of alkyl, alkoxy, hydroxy, fluoro, and trifluoromethyl;

each $R_A$ is independently selected from the group consisting of halogen, hydroxy, alkyl, alkenyl, haloalkyl, alkoxy, alkylthio, and —N(R$_9$)$_2$;

$R_9$ is selected from the group consisting of hydrogen and alkyl; and

R" is hydrogen or a non-interfering substituent;

or a pharmaceutically acceptable salt thereof.

In one embodiment, the present invention provides a compound of Formula Ia:

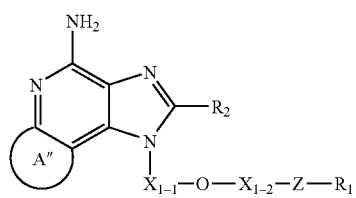

Ia wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

A" is a fused aryl ring or heteroaryl ring containing one heteroatom selected from the group consisting of N and S, wherein the aryl or heteroaryl ring is unsubstituted or substituted by one or more R groups, or a fused 5 to 7 membered saturated ring, optionally containing one heteroatom selected from the group consisting of N and S, and unsubstituted or substituted by one or more $R_A$ groups;

each R is independently selected from the group consisting of alkyl, alkoxy, hydroxy, fluoro, and trifluoromethyl;

each $R_A$ is independently selected from the group consisting of halogen, hydroxy, alkyl, alkenyl, haloalkyl, alkoxy, alkylthio, and —N(R$_9$)$_2$;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

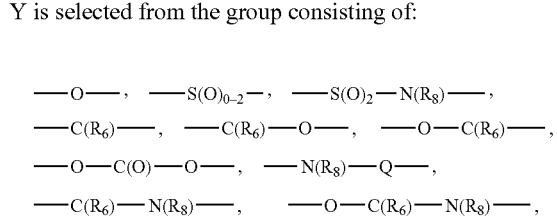

-continued $$-C(R_6)-N(OR_9)-, \quad \overset{\displaystyle \left(\ \right)}{\underset{R_{10}}{N}}-Q-,$$

$$-N\overset{\displaystyle \left(\ \right)}{\underset{R_7}{-C(R_6)-N-W-}}, \quad -N\overset{\displaystyle \left(\ \right)}{\underset{R_7}{-R_7-N-W-}},$$

$$-V-N\overset{\displaystyle \left(\ \right)}{\underset{R_{10}}{}}, \text{ and}$$

$$\overset{\displaystyle \left(\ \right)}{\underset{R_{10}}{N}}-C(R_6)-\overset{\displaystyle \left(\ \right)}{\underset{R_{10}}{N}};$$

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

$$-N\overset{\displaystyle \left(\ \right)}{\underset{R_7}{-C(R_6)}}, \quad -N\overset{\displaystyle \left(\ \right)}{\underset{R_7}{-S(O)_2}}, \quad -V-N\overset{\displaystyle \left(\overset{(CH_2)_a}{\underset{(CH_2)_b}{}}\ \right)}{}A, \text{ and}$$

$$\overset{\displaystyle \left(\ \right)}{\underset{R_{10}}{N}}-C(R_6)-N\overset{\displaystyle \left(\overset{(CH_2)_a}{\underset{(CH_2)_b}{}}\ \right)}{}A;$$

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —(O)$_2$—; and
a and b are independently integers from 1 to 6 with the proviso that a+b is ≦7;

or a pharmaceutically acceptable salt thereof.

In one embodiment, the present invention provides a compound of Formula II:

wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

R is selected from the group consisting of alkyl, alkoxy, hydroxy, fluoro, and trifluoromethyl;

n is 0 to 4; and

R" is hydrogen or a non-interfering substituent;

or a pharmaceutically acceptable salt thereof.

In one embodiment, the present invention provides a compound of Formula IIa:

IIa wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
  $C_{1-10}$ alkyl,
  $C_{2-10}$ alkenyl,
  $C_{2-10}$ alkynyl,
  aryl,
  aryl-$C_{1-10}$ alkylenyl,
  aryloxy-$C_{1-10}$ alkylenyl,
  $C_{1-10}$ alkylarylenyl,
  heteroaryl,
  heteroaryl-$C_{1-10}$ alkylenyl,
  heteroaryloxy-$C_{1-10}$ alkylenyl,
  $C_{1-10}$ alkylheteroarylenyl,
  heterocyclyl,
  heterocyclyl-$C_{1-10}$ alkylenyl, and
  $C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

R is selected from the group consisting of alkyl, alkoxy, hydroxy, fluoro, and trifluoromethyl;

n is 0 to 4;

$R_2$ is selected from the group consisting of
  —$R_4$,
  —X—$R_4$,
  —X—Y—$R_4$, and
  —X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—, —S(O)$_{0-2}$—, —S(O)$_2$—N(R$_8$)—,
—C(R$_6$)—, —C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,
—C(R$_6$)—N(OR$_9$)—, and $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In one embodiment, the present invention provides a compound of Formula IIa:

IIa

[Chemical structure showing imidazoquinoline core with NH₂, R₂, X₁₋₁—O—X₁₋₂—Z—R₁, and (R)ₙ substituents]

wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)₂—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

R is selected from the group consisting of alkyl, alkoxy, hydroxy, fluoro, and trifluoromethyl;

n is 0 to 4;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—S(O)₀₋₂—, —S(O)₂—N($R_8$)—, —C($R_6$)—,
—C($R_6$)—O—, —O—C($R_6$)—,
—O—C(O)—O—, —N($R_8$)—Q—,
—C($R_6$)—N($R_8$)—, —O—C($R_6$)—N($R_8$)—,
—C($R_6$)—N(OR₉)—, [cyclic N—Q with R₁₀],
—N—C($R_6$)—N—W—, —N—$R_7$—N—W—, [with R₇]
—V—N— [cyclic with R₁₀], and
[cyclic N—C($R_6$)—N with R₁₀];

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

[Structures: —N(R₇)—C(R₆)—, —N(R₇)—S(O)₂—, —V—N cyclic with (CH₂)ₐ—A—(CH₂)ᵦ, and cyclic N—C(R₆)—N with R₁₀ and (CH₂)ₐ—A—(CH₂)ᵦ]

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)₀₋₂—, —CH₂—, and —N($R_4$)—;
Q is selected from the group consisting of a bond, —C($R_6$)—, —C($R_6$)—C($R_6$)—, —S(O)₂—, —C($R_6$)—N($R_8$)—W—, —S(O)₂—N($R_8$)—, —C($R_6$)—O—, and —C($R_6$)—N(OR₉)—;
V is selected from the group consisting of —C($R_6$)—, —O—C($R_6$)—, —N($R_8$)—C($R_6$)—, and —S(O)₂—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In one embodiment, the present invention provides a compound of Formula III:

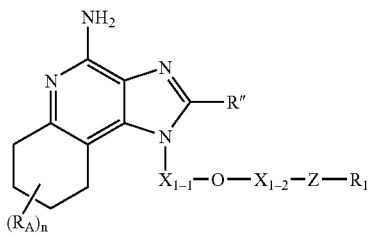

III wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and $C_{1-10}$ alkyl, $C_{2-10}$ alkenyl, $C_{2-10}$ alynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

$R_A$ is selected from the group consisting of:
halogen,
hydroxy,
alkyl,
alkenyl,
haloalkyl,
alkoxy,
alkylthio, and
—N($R_9$)$_2$;

n is 0 to 4; and

R'' is hydrogen or a non-interfering substituent;

or a pharmaceutically acceptable salt thereof.

In one embodiment, the present invention provides a compound of Formula IIIa:

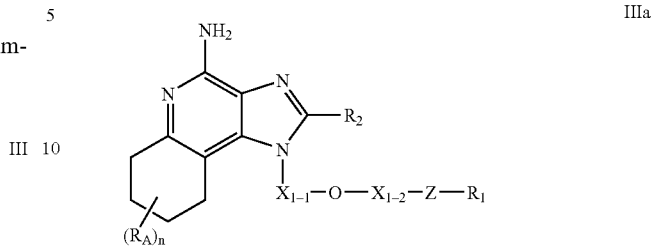

IIIa wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and $C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

$R_A$ is selected from the group consisting of:
halogen,
hydroxy,
alkyl,
alkenyl,
haloalkyl,
alkoxy,
alkylthio, and
—N($R_9$)$_2$;

n is 0 to 4;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

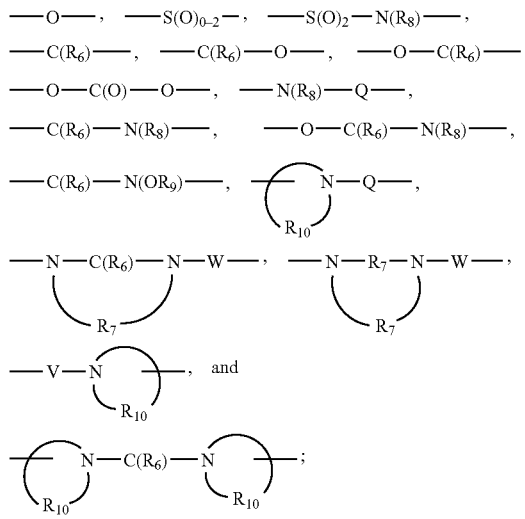

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

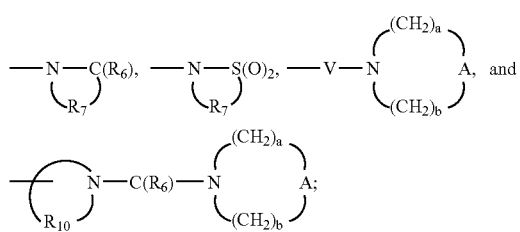

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In one embodiment, the present invention provides a compound of Formula IIIa:

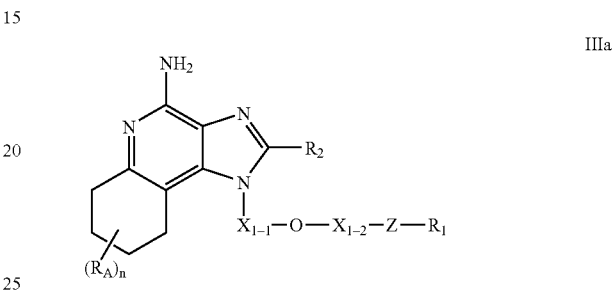

IIIa wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

$R_A$ is selected from the group consisting of:
halogen,
hydroxy,
alkyl,
alkenyl,
haloalkyl, alkoxy,
alkylthio, and
—N(R$_9$)$_2$;
n is 0 to 4;
R$_2$ is selected from the group consisting of
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

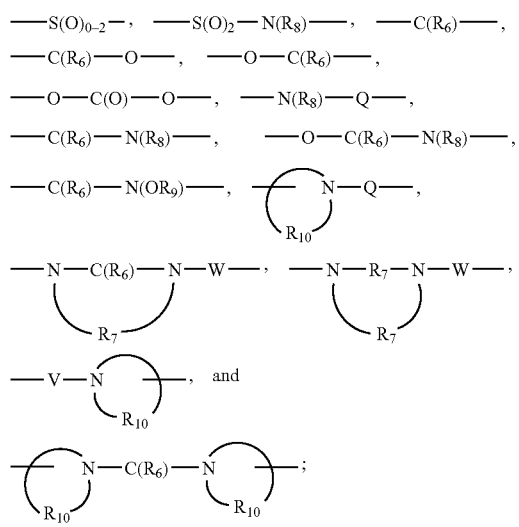

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

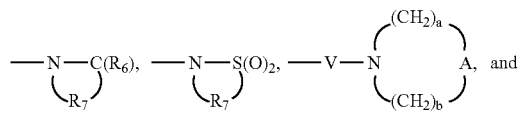

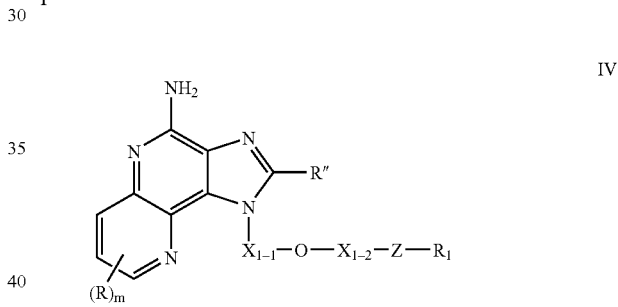

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In one embodiment, the present invention provides a compound of Formula IV:

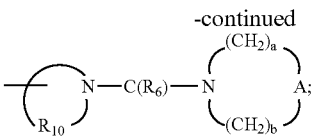

wherein:
X$_{1-1}$ and X$_{1-2}$ are independently selected from the group consisting of C$_{1-10}$ alkylene, C$_{4-10}$ alkenylene, and C$_{4-10}$ alkynylene; wherein the terminal carbon atoms of alkenylene and alkynylene are tetrahedral;
Z is selected from the group consisting of —S—, —S(O)—, and —S(O)$_2$—;
R$_1$ is selected from the group consisting of:
C$_{1-10}$ alkyl,
C$_{2-10}$ alkenyl,
C$_{2-10}$ alkynyl,
aryl,
aryl-C$_{1-10}$ alkylenyl,
aryloxy-C$_{1-10}$ alkylenyl,
C$_{1-10}$ alkylarylenyl,
heteroaryl,
heteroaryl-C$_{1-10}$ alkylenyl,
heteroaryloxy-C$_{1-10}$ alkylenyl,
C$_{1-10}$ alkylheteroarylenyl,
heterocyclyl,
heterocyclyl-C$_{1-10}$ alkylenyl, and
C$_{1-10}$ alkyl, C$_{2-10}$ alkenyl, C$_{2-10}$ alkynyl, aryl, aryl-C$_{1-10}$ alkylenyl, aryloxy-C$_{1-10}$ alkylenyl, C$_{1-10}$ alkylarylenyl, heteroaryl, heteroaryl-C$_{1-10}$ alkylenyl, heteroaryloxy-C$_{1-10}$ alkylenyl, C$_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

R is selected from the group consisting of alkyl, alkoxy, hydroxy, fluoro, and trifluoromethyl;

m is 0 to 3; and

R" is hydrogen or a non-interfering substituent;

or a pharmaceutically acceptable salt thereof.

In one embodiment, the present invention provides a compound of Formula IVa:

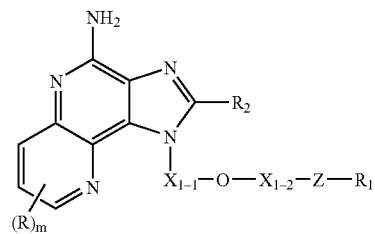

IVa wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

R is selected from the group consisting of alkyl, alkoxy, hydroxy, fluoro, and trifluoromethyl;

m is 0 to 3;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—, —S(O)$_{0-2}$—, —S(O)$_2$—N($R_8$)—,

—C($R_6$)—, —C($R_6$)—O—, —O—C($R_6$)—,

—O—C(O)—O—, —N($R_8$)—Q—,

—C($R_6$)—N($R_8$)—, —O—C($R_6$)—N($R_8$)—,

—C($R_6$)—N(O$R_9$)—,

[cyclic structure with N—Q and $R_{10}$],

—N—C($R_6$)—N—W—, —N—$R_7$—N—W—,
    |                      |
    $R_7$                  $R_7$

—V—N[cyclic with $R_{10}$]—, and

[cyclic with $R_{10}$]N—C($R_6$)—N[cyclic with $R_{10}$];

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

—N—C($R_6$), —N—S(O)$_2$, —V—N[(CH$_2$)$_a$ / (CH$_2$)$_b$]A, and
  |             |
  $R_7$         $R_7$

[cyclic with $R_{10}$]N—C($R_6$)—N[(CH$_2$)$_a$ / (CH$_2$)$_b$]A;

$R_6$ is selected from the group consisting of =O and =S;
$R_7$ is $C_{2-7}$ alkylene;

R$_8$ is selected from the group consisting of hydrogen, alkyl, alkoxyalkylenyl, and arylalkylenyl;

R$_9$ is selected from the group consisting of hydrogen and alkyl;

R$_{10}$ is C$_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —(O)$_2$—; and a and b are independently integers from 1 to 6 with the proviso that a+b is $\leq 7$;

or a pharmaceutically acceptable salt thereof.

The present invention also provides intermediate compounds, which are useful, for example, in preparing compounds of Formulas I-IIIa. In one embodiment, the present invention provides a compound of Formula V:

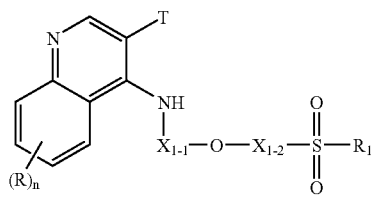

V wherein:

T is —NH$_2$ or —NO$_2$;

X$_{1-1}$ and X$_{1-2}$ are independently selected from the group consisting of C$_{1-10}$ alkylene, C$_{4-10}$ alkenylene, and C$_{4-10}$ alkynylene; wherein the terminal carbon atoms of alkenylene and alkynylene are tetrahedral;

R$_1$ is selected from the group consisting of:
C$_{1-10}$ alkyl,
C$_{2-10}$ alkenyl,
C$_{2-10}$ alkynyl,
aryl,
aryl-C$_{1-10}$ alkylenyl,
aryloxy-C$_{1-10}$ alkylenyl,
C$_{1-10}$ alkylarylenyl,
heteroaryl,
heteroaryl-C$_{1-10}$ alkylenyl,
heteroaryloxy-C$_{1-10}$ alkylenyl,
C$_{1-10}$ alkylheteroarylenyl,
heterocyclyl,
heterocyclyl-C$_{1-10}$ alkylenyl, and
C$_{1-10}$ alkyl, C$_{2-10}$ alkenyl, C$_{2-10}$ alkynyl, aryl, aryl-C$_{1-10}$ alkylenyl, aryloxy-C$_{1-10}$ alkylenyl, C$_{1-10}$ alkylarylenyl, heteroaryl, heteroaryl-C$_{1-10}$ alkylenyl, heteroaryloxy-C$_{1-10}$ alkylenyl, C$_{1-10}$ alkylheteroarylenyl, heterocyclyl, and heterocyclyl-C$_{1-10}$ alkylenyl substituted by one or more substituents independently selected from the group consisting of C$_{1-10}$ alkyl, C$_{1-10}$ alkoxy, hydroxy-C$_{1-10}$ alkyl, halo-C$_{1-10}$ alkyl, halo-C$_{1-10}$ alkoxy, halogen, nitro, hydroxy, cyano, aryl, aryloxy, heteroaryl, heteroaryloxy, heterocyclyl, amino, C$_{1-10}$ alkylamino, di(C$_{1-10}$ alkyl)amino, and in the case of C$_{1-10}$ alkyl, C$_{2-10}$ alkenyl, C$_{2-10}$ alkynyl, and heterocyclyl, oxo; wherein heteroaryl, C$_{1-10}$ alkylheteroarylenyl, and heterocyclyl are attached to Z through a carbon atom;

R is selected from the group consisting of alkyl, alkoxy, hydroxy, fluoro, and trifluoromethyl; and n is 0 to 4;

or a pharmaceutically acceptable salt thereof.

In one embodiment, the present invention provides a compound of Formula VI:

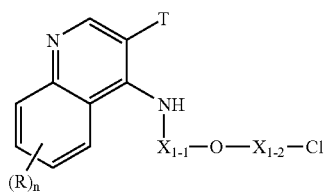

VI wherein:

T is —NH$_2$ or —NO$_2$;

X$_{1-1}$ and X$_{1-2}$ are independently selected from the group consisting of C$_{1-10}$ alkylene, C$_{4-10}$ alkenylene, and C$_{4-10}$ alkynylene; wherein the terminal carbon atoms of alkenylene and alkynylene are tetrahedral;

R is selected from the group consisting of alkyl, alkoxy, hydroxy, fluoro, and trifluoromethyl; and n is 0 to 4;

or a pharmaceutically acceptable salt thereof.

In one embodiment, the present invention provides a compound of Formula VIII:

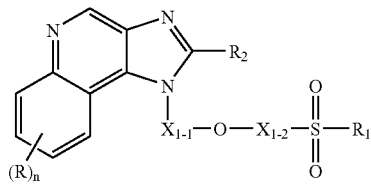

VIII wherein:

X$_{1-1}$ and X$_{1-2}$ are independently selected from the group consisting of C$_{1-10}$ alkylene, C$_{4-10}$ alkenylene, and C$_{4-10}$ alkynylene; wherein the terminal carbon atoms of alkenylene and alkynylene are tetrahedral;

R$_1$ is selected from the group consisting of:
C$_{1-10}$ alkyl,
C$_{2-10}$ alkenyl,
C$_{2-10}$ alkynyl,
aryl,
aryl-C$_{1-10}$ alkylenyl,
aryloxy-C$_{1-10}$ alkylenyl,
C$_{1-10}$ alkylarylenyl,
heteroaryl,
heteroaryl-C$_{1-10}$ alkylenyl,
heteroaryloxy-C$_{1-10}$ alkylenyl,
C$_{1-10}$ alkylheteroarylenyl,
heterocyclyl,
heterocyclyl-C$_{1-10}$ alkylenyl, and
C$_{1-10}$ alkyl, C$_{2-10}$ alkenyl, C$_{2-10}$ alkynyl, aryl, aryl-C$_{1-10}$ alkylenyl, aryloxy-C$_{1-10}$ alkylenyl, C$_{1-10}$ alkylarylenyl, heteroaryl, heteroaryl-C$_{1-10}$ alkylenyl, heteroaryloxy-C$_{1-10}$ alkylenyl, C$_{1-10}$ alkylheteroarylenyl, heterocyclyl, and heterocyclyl-C$_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

R is selected from the group consisting of alkyl, alkoxy, hydroxy, fluoro, and trifluoromethyl;

n is 0 to 4;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—, —S(O)$_{0-2}$—, —S(O)$_2$—N(R$_8$)—,
—C(R$_6$)—, —C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,
—C(R$_6$)—N(OR$_9$)—,

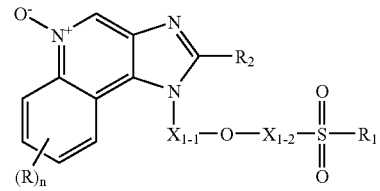

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of:

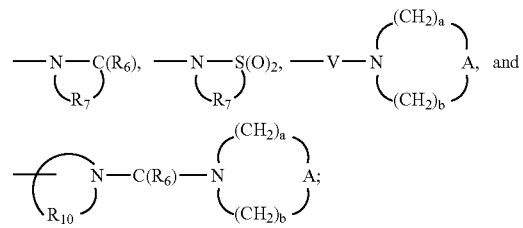

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_9$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In one embodiment, the present invention provides a compound of Formula IX:

IX wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and $C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ to alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;

R is selected from the group consisting of alkyl, alkoxy, hydroxy, fluoro, and trifluoromethyl;

n is 0 to 4;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—, —S(O)$_{0-2}$—, —S(O)$_2$—N($R_8$)—,
—C($R_6$)—, —C($R_6$)—O—, —O—C($R_6$)—,
—O—C(O)—O—, —N($R_8$)—Q—,
—C($R_6$)—N($R_8$)—, —O—C($R_6$)—N($R_8$)—,
—C($R_6$)—N(OR$_9$)—,

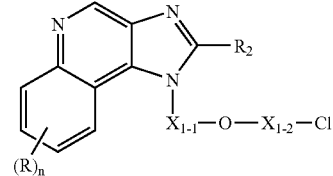

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of:

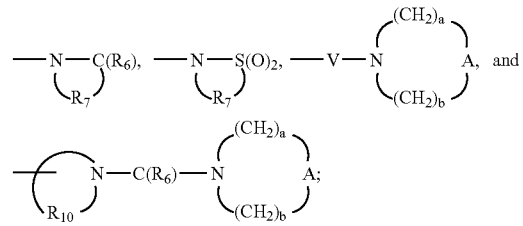

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, —CH$_2$—, and —N($R_4$)—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(OR$_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and S(O)$_2$—; and a and b are independently integers from 1 to 6 with the proviso that a+b is ≦7.

In one embodiment, the present invention provides a compound of Formula XXIIIa:

XXIIIa

[Structure: bicyclic imidazoquinoline with $R_2$ substituent at 2-position, $X_{1-1}$—O—$X_{1-2}$—Cl substituent at N1, and $(R)_n$ on the benzene ring]

wherein:

$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

R is selected from the group consisting of alkyl, alkoxy, hydroxy, fluoro, and trifluoromethyl;

n is 0 to 4;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—, —S(O)$_{0-2}$—, —S(O)$_2$—N(R$_8$)—,
—C(R$_6$)—, —C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,

—C(R$_6$)—N(OR$_9$)—, ⟨N(R$_{10}$)—Q⟩—,

—N(R$_7$)—C(R$_6$)—N—W—, —N(R$_7$)—R$_7$—N—W—,

—V—N⟨R$_{10}$⟩, and

⟨N(R$_{10}$)—C(R$_6$)—N(R$_{10}$)⟩;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

—N(R$_7$)—C(R$_6$), —N(R$_7$)—S(O)$_2$, —V—N⟨(CH$_2$)$_a$/A/(CH$_2$)$_b$⟩, and

⟨N(R$_{10}$)—C(R$_6$)—N⟨(CH$_2$)$_a$/A/(CH$_2$)$_b$⟩;

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In one embodiment, the present invention provides a compound of Formula XXV:

XXV wherein:
X$_{1-1}$ and X$_{1-2}$ are independently selected from the group consisting of C$_{1-10}$ alkylene, C$_{4-10}$ alkenylene, and C$_{4-10}$ alkynylene; wherein the terminal carbon atoms of alkenylene and alkynylene are tetrahedral;
R is selected from the group consisting of alkyl, alkoxy, hydroxy, fluoro, and trifluoromethyl;
n is 0 to 4;
R$_2$ is selected from the group consisting of
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

—O—, —S(O)$_{0-2}$—, —S(O)$_2$—N(R$_8$)—,
—C(R$_6$)—, —C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,

—C(R$_6$)—N(OR$_9$)—, ⟨N(R$_{10}$)—Q⟩—,

—N(R$_7$)—C(R$_6$)—N—W—, —N(R$_7$)—R$_7$—N—W—,

—V—N⟨R$_{10}$⟩, and

⟨N(R$_{10}$)—C(R$_6$)—N(R$_{10}$)⟩;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of allyl, alkenyl, alkynyl, and heterocyclyl, oxo;

$R_5$ is selected from the group consisting of:

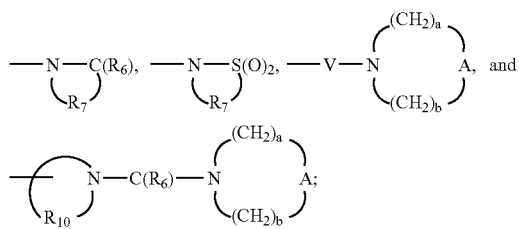

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —(O)$_2$—; and
a and b are independently integers from 1 to 6 with the proviso that a+b is ≦7.

In one embodiment, the present invention provides a compound of Formula XXIVa:

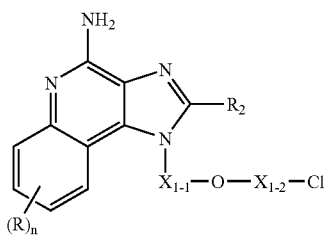

XXIVa wherein:

$X_{1-1}$ and $X_{1-2}$ are independently selected from the group consisting of $C_{1-10}$ alkylene, $C_{1-10}$ alkenylene, and $C_{4-10}$ alkynylene; wherein the terminal carbon atoms of alkenylene and alkynylene are tetrahedral;

R is selected from the group consisting of alkyl, alkoxy, hydroxy, fluoro, and trifluoromethyl;

n is 0 to 4;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

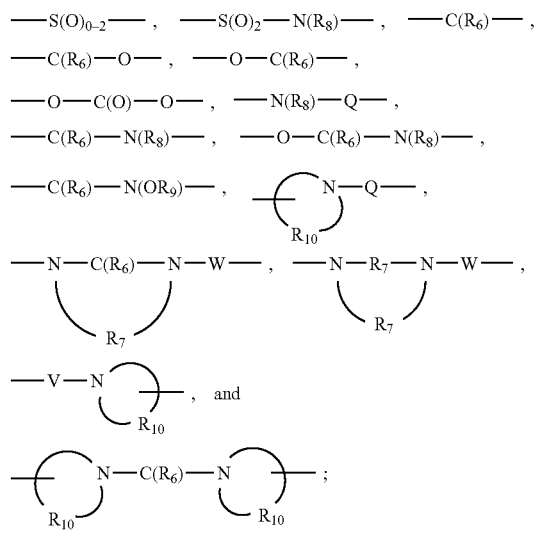

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

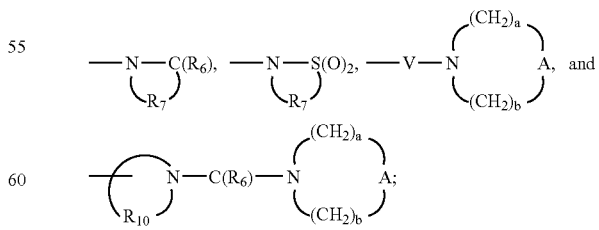

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;

R₉ is selected from the group consisting of hydrogen and alkyl;

R₁₀ is C$_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

Herein, "non-interfering" means that the ability of the compound or salt, which includes a non-interfering substituent, to modulate the biosynthesis of one or more cytokines is not destroyed by the non-interfering substitutent. For certain embodiments, R" is hydrogen or a non-interfering substituent. Illustrative non-interfering R" groups include those described above for R$_2$.

As used herein, a carbon atom which is tetrahedral is a carbon atom which is bonded to four atoms wherein each of the four bonds is a single bond.

As used herein, the terms "alkyl," "alkenyl," "alkynyl" and the prefix "alk-" are inclusive of both straight chain and branched chain groups and of cyclic groups, i.e. cycloalkyl and cycloalkenyl, as well as combinations thereof. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "-cyclic(CH$_2$)$_{3-6}$—" represents the divalent form of cycloalkyl groups of three to six carbon atoms. In one embodiment, "-cyclic(CH$_2$)$_{3-6}$—" is

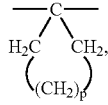

wherein p is an integer of 0 to 3.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno. In certain embodiments, the fused aryl ring is benzo.

The term "fused heteroaryl ring" includes the fused forms of 5 or 6 membered aromatic rings that contain one heteroatom selected from S and N. In certain embodiments, the fused heteroaryl ring is pyrido or thieno. In certain embodiments, the fused heteroaryl ring is pyrido. In certain of these embodiments, the pyrido ring is

wherein the highlighted bond indicates the position where the ring is fused.

The term "fused 5 to 7 membered saturated ring" includes rings which are fully saturated except for the bond where the ring is fused. In certain embodiments, the ring is a cyclohexene ring. In certain embodiments wherein one heteroatom (N or S) is present, the ring is tetrahydropyrido or dihydrothieno. In certain embodiments, the ring is tetrahydropyrido. In certain of these embodiments, the ring is

wherein the highlighted bond indicates the position where the ring is fused.

When a group (or substituent or variable) is present more than once in any Formula described herein, each group (or substituent or variable) is independently selected, whether explicitly stated or not. For example, for the formula —N($R_9$)$_2$ each $R_9$ group is independently selected. In another example, when an —N($R_8$)—C($R_6$)—N($R_8$)— group is present, each $R_8$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., A", R", $R_1$, $R_2$, R, $R_A$, $X_{1-1}$, $X_{1-2}$, Z, Q, T, m, and n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In some embodiments, A" is a fused aryl ring or heteroaryl ring containing one heteroatom selected from the group consisting of N and S, wherein the aryl or heteroaryl ring is unsubstituted or substituted by one or more R groups, or a fused 5 to 7 membered saturated ring, optionally containing one heteroatom selected from the group consisting of N and S, and unsubstituted or substituted by one or more $R_A$ groups.

In some embodiments, A" is a fused aryl ring which is unsubstituted or substituted by one or more R groups. In some embodiments the fused aryl ring is unsubstituted.

In some embodiments, A" is a fused heteroaryl ring containing one heteroatom selected from the group consisting of N and S, and unsubstituted or substituted by one or more R groups. In some embodiments the fused heteroaryl ring is unsubstituted.

In some embodiments, A" is a fused 5 to 7 membered saturated ring which is unsubstituted or substituted by one or more $R_A$ groups. In some embodiments, the 5 to 7 membered ring is unsubstituted.

In some embodiments, A" is a fused 5 to 7 membered saturated ring containing one heteroatom selected from the group consisting of N and S, and unsubstituted or substituted by one or more $R_A$ groups. In some embodiments, the 5 to 7 membered saturated ring containing one heteroatom is unsubstituted.

In some embodiments, each R is independently selected from the group consisting of alkyl, alkoxy, hydroxy, fluoro, and trifluoromethyl.

In some embodiments, each $R_A$ is independently selected from the group consisting of halogen, hydroxy, alkyl, alkenyl, haloalkyl, alkoxy, alkylthio, and —N($R_9$)$_2$.

In some embodiments, $R_1$ is selected from the group consisting of $C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, heterocyclyl-$C_{1-10}$ alkylenyl, and $C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom.

In some embodiments, $R_1$ is linear or branched $C_{1-4}$ alkyl, aryl, or 5 to 10 membered heteroaryl containing one or two heteroatoms, wherein the alkyl, aryl, or heteroaryl group may be unsubstituted or substituted with one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino, $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom.

In some embodiments, $R_1$ is methyl, ethyl, 1-propyl, 2-propyl, 2-methylpropyl, 2-hydroxy-2-methylpropyl, phenyl, 4-chlorophenyl, or 4-fluorophenyl.

In some embodiments, $R_1$ is methyl, ethyl, 2-propyl, 2-methylpropyl, 2-hydroxy-2-methylpropyl, or phenyl.

In some embodiments, R" is hydrogen or a non-interfering substituent.

In some embodiments, R" is selected from the group consisting of —$R_4$, —X—$R_4$, —X—Y—$R_4$, and —X—$R_5$.

In some embodiments, R" is hydrogen, alkyl, hydroxyalkylenyl, or alkoxyalkylenyl.

In some embodiments, R" is hydrogen, $C_{1-4}$ alkyl, hydroxy$C_{1-4}$ alkylenyl, or $C_{1-4}$ alkoxy$C_{1-4}$ alkylenyl.

In some embodiments, R" is alkyl, hydroxyalkylenyl, or alkoxyalkylenyl.

In some embodiments, R" is $C_{1-4}$ alkyl, hydroxy$C_{1-4}$ alkylenyl, or $C_{1-4}$ alkoxy$C_{1-4}$ alkylenyl.

In some embodiments, R" is hydrogen, methyl, ethyl, propyl, butyl, 2-hydroxyethyl, hydroxymethyl, 2-methoxyethyl, or ethoxymethyl.

In some embodiments, R" is methyl, ethyl, propyl, butyl, 2-methoxyethyl, or ethoxymethyl.

In some embodiments, $R_2$ is selected from the group consisting of —$R_4$, —X—$R_4$, —X—Y—$R_4$, and —X—$R_5$.

In some embodiments, $R_2$ is hydrogen, alkyl, hydroxyalkylenyl, or alkoxyalkylenyl.

In some embodiments, $R_2$ is hydrogen, $C_{1-4}$ alkyl, hydroxy$C_{1-4}$ alkylenyl, or $C_{1-4}$ alkoxy$C_{1-4}$ alkylenyl.

In some embodiments, $R_2$ is alkyl, or alkoxyalkylenyl.

In some embodiments, $R_2$ is $C_{1-4}$ alkyl, hydroxy$C_{1-4}$ alkylenyl, or $C_{1-4}$ alkoxy$C_{1-4}$ alkylenyl.

In some embodiments, $R_2$ is $C_{1-4}$ alkyl, or $C_{1-4}$ alkoxy$C_{1-4}$ alkylenyl.

In some embodiments, $R_2$ is hydrogen, methyl, ethyl, propyl, butyl, 2-hydroxyethyl, hydroxymethyl, 2-methoxyethyl, or ethoxymethyl.

In some embodiments, $R_2$ is methyl, ethyl, propyl, butyl, 2-methoxyethyl, or ethoxymethyl.

In some embodiments, $X_{1-1}$ and $X_{1-2}$ are independently selected from $C_{2-7}$ alkylene groups.

In some embodiments, $X_{1-1}$ and $X_{1-2}$ are independently selected from $C_{2-4}$ alkylene groups.

In some embodiments, $X_{1-1}$ is —(CH$_2$)$_{2-4}$—, —CH$_2$—C(CH$_3$)$_2$—, or —CH$_2$-cyclic(CH$_2$)$_{3-6}$—.

In some embodiments, —CH$_2$-cyclic(CH$_2$)$_{3-6}$— is

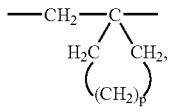

wherein p is an integer of 0 to 3.

In some embodiments, X$_{1-1}$ is —(CH$_2$)$_{2-4}$—, or —CH$_2$—C(CH$_3$)$_2$—.

In some embodiments, X$_{1-1}$ is

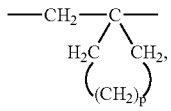

wherein p is an integer of 0 to 3.

In some embodiments, X$_{1-2}$ is —(CH$_2$)$_2$— or —(CH$_2$)$_3$—.

In some embodiments, Z is selected from the group consisting of —S—, —S(O)—, and —S(O)$_2$—.

In some embodiments, Z is —S(O)$_2$—.

In some embodiments, Z is —S(O)—.

In some embodiments, Z is —S—.

In some embodiments, m is an integer of 0 to 3.

In some embodiments, m is 0.

In some embodiments, n is an integer of 0 to 4.

In some embodiments, n is 0.

In some embodiments, A is selected from the group consisting of —O—, —C(O)—, —S(O)$_{0-2}$—, —CH$_2$—, and —N(R$_4$)—.

In some embodiments, A is —O—.

In some embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—.

In some embodiments, Q is —C(R$_6$)—, —S(O)$_2$—, or —C(R$_6$)—N(R$_8$)—W—.

In some embodiments, T is —NH$_2$ or —NO$_2$. In some embodiments, T is —NH$_2$. In some embodiments, T is —NO$_2$.

In some embodiments, V is selected from the group consisting of —C(R$_6$)—, —O—C(R$_6$)—, —N(R$_8$)—C(R$_6$)—, and —S(O)$_2$—.

In some embodiments, W is selected from the group consisting of a bond, —C(O)—, and —S(O)$_2$—.

In some embodiments, W is a bond.

In some embodiments, a and b are independently integers from 1 to 6 with the proviso that a+b is ≦7.

In some embodiments, a and b are each the integer 2.

In some embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups.

In some embodiments, X is alkylene.

In some embodiments, X is —(CH$_2$)$_{1-3}$—.

In some embodiments, Y is selected from the group consisting of

—S(O)$_{0-2}$—, —S(O)$_2$—N(R$_8$)—,

—C(R$_6$)—, —C(R$_6$)—O—, —O—C(R$_6$)—,

—O—C(O)—O—, —N(R$_8$)—Q—,

—C(R$_6$)—N(R$_8$)—, —O—C(R$_6$)—N(R$_8$)—,

—C(R$_6$)—N(OR$_9$)—,

![ring with N-Q and R10]

—N—C(R$_6$)—N—W—, —N—R$_7$—N—W—,
   \R$_7$/           \R$_7$/

—V—N (ring R$_{10}$), and (ring R$_{10}$) N—C(R$_6$)—N (ring R$_{10}$).

In some embodiments, Y is selected from the group consisting of

—S(O)$_{0-2}$—, —S(O)$_2$—N(R$_8$)—,

—C(R$_6$)—, —C(R$_6$)—O—, —O—C(R$_6$)—,

—O—C(O)—O—, —N(R$_8$)—Q—,

—C(R$_6$)—N(R$_8$)—, —O—C(R$_6$)—N(R$_8$)—,

—C(R$_6$)—N(OR$_9$)—,

![ring with N-Q and R10]

—N—C(R$_6$)—N—W—, —N—R$_7$—N—W—,
   \R$_7$/           \R$_7$/

—V—N (ring R$_{10}$), and (ring R$_{10}$) N—C(R$_6$)—N (ring R$_{10}$).

In some embodiments, R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.-

In some embodiments, $R_5$ is selected from the group consisting of:

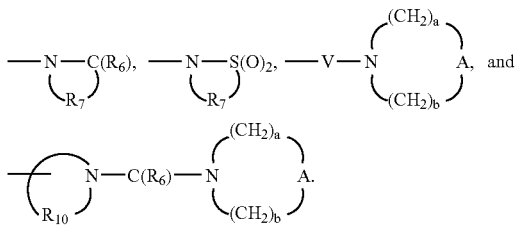

In some embodiments, $R_6$ is selected from the group consisting of =O and =S.

In some embodiments, $R_6$ is =O.

In some embodiments, $R_7$ is $C_{2-7}$ alkylene.

In some embodiments, $R_8$ is selected from the group consisting of hydrogen, alkyl, alkoxyalkylenyl, and arylalkylenyl.

In some embodiments, $R_8$ is hydrogen or methyl.

In some embodiments, $R_8$ is hydrogen.

In some embodiments, $R_9$ is selected from the group consisting of hydrogen and alkyl.

In some embodiments, $R_{10}$ is $C_{3-8}$ alkylene.

In some embodiments, particularly embodiments of Formulas I, Ia, II, IIa, III, IIIa, IV, IVa, V, VI, VIII, IX, XXIIIa, XXIVa, or XXV, $X_{1-1}$ and $X_{1-2}$ are independently selected from $C_{2-7}$ alkylene groups; and in certain embodiments $X_{1-1}$ and $X_{1-2}$ are independently selected from $C_{2-4}$ alkylene groups. In certain embodiments, $X_{1-1}$ is —$(CH_2)_{2-4}$—, —$CH_2$—$C(CH_3)_2$—, or —$CH_2$-cyclic$(CH_2)_{3-6}$—. In certain of these embodiments, $X_{1-1}$ is —$(CH_2)_{2-4}$— or —$CH_2$—$C(CH_3)_2$—. In certain of these embodiments $X_{1-2}$ is —$(CH_2)_2$—, or —$(CH_2)_3$—.

In some embodiments, particularly embodiments of Formulas I, Ia, IIa, III, IIIa, IV, or IVa, Z is —$S(O)_2$—.

In some embodiments, particularly embodiments of Formulas I, Ia, II, IIa, III, IIIa, IV, or IVa, Z is —$S(O)$—.

In some embodiments, particularly embodiments of Formulas I, Ia, II, IIa, III, IIIa, IV, or IVa, Z is —S—.

In some embodiments, particularly embodiments of Formulas I, Ia, II, IIa, III, IIIa, IV, IVa, V, VIII, or IX, $R_1$ is linear or branched $C_{1-4}$ alkyl, aryl, or 5 to 10 membered heteroaryl containing one or two heteroatoms, wherein the alkyl, aryl, or heteroaryl group may be unsubstituted or substituted with one or more substituents. In certain embodiments $R_1$ is methyl, ethyl, 1-propyl, 2-propyl, 2-methylpropyl, 2-hydroxy-2-methylpropyl, phenyl, 4-chlorophenyl, or 4-fluorophenyl. In certain embodiments $R_1$ is methyl, ethyl, 2-propyl, 2-methylpropyl, 2-hydroxy-2-methylpropyl, or phenyl.

In some embodiments, particularly embodiments of Formulas Ia, IIa, IIIa, IVa, VIII, IX, XXIIIa, XXIVa, or XXV, X is —$(CH_2)_{1-3}$—.

In some embodiments, particularly embodiments of Formulas I, II, III, or IV, R" is hydrogen, alkyl, hydroxyalkylenyl, or alkoxyalkylenyl.

In some embodiments, particularly embodiments of Formulas I, II, III, or IV, R" is hydrogen, methyl, ethyl, propyl, butyl, 2-hydroxyethyl, hydroxymethyl, 2-methoxyethyl, or ethoxymethyl.

In some embodiments, particularly embodiments of Formulas Ia, IIa, IIIa, IVa, VIII, IX, XXIIIa, XXIVa, or XXV, $R_2$ is hydrogen, alkyl, hydroxyalkylenyl, or alkoxyalkylenyl. In certain embodiments $R_2$ is hydrogen, methyl, ethyl, propyl, butyl, 2-hydroxyethyl, hydroxymethyl, 2-methoxyethyl, or ethoxymethyl.

In some embodiments, particularly embodiments of Formulas Ia, IIa, IIIa, IVa, VII, IX, XXIIIa, XXIVa, or XXV, $R_2$ is alkyl or alkoxyalkylenyl. In certain embodiments $R_2$ is methyl, ethyl, propyl, butyl, 2-methoxyethyl, or ethoxymethyl.

In some embodiments, particularly embodiments of Formulas II, IIa, III, IIIa, V, VI, VIII, IX, XXIIIa, XXIVa, or XXV, n is 0.

In some embodiments, particularly embodiments of Formulas IV or IVa, m is 0.

In some embodiments, particularly embodiments of Formulas I, II, III, or IV, the compound or salt induces the biosynthesis of one or more cytokines.

Preparation of the Compounds

Compounds of the invention can be prepared according to Reaction Scheme I where R, $R_1$, $R_2$, $X_{1-1}$, $X_{1-2}$, and n are as defined above. In step (1) a 4-chloro-3-nitroquinoline of Formula XXVII is reacted with an amine of the formula $R_1$—$S(O)_2$—$X_{1-2}$—O—$X_{1-1}$—$NH_2$ or a salt thereof to provide a 3-nitroquinolin-4-amine of Formula XXVIII. The reaction can be carried out by adding the 4-chloro-3-nitroquinoline to a solution of an amine of the formula $R_1$—$S(O)_2$—$X_{1-2}$—O—$X_{1-1}$—$NH_2$ or salt thereof in a suitable solvent such as anhydrous dichloromethane in the presence of a base such as triethylamine. The reaction can be run at ambient temperature. The product or a pharmaceutically acceptable salt thereof can be isolated by conventional methods. Many 4-chloro-3-nitroquinolines of Formula XXVII are known or can be prepared using known synthetic methods, see for example, U.S. Pat. Nos. 4,689,338; 5,175,296; 5,367,076; and 5,389,640; and the references cited therein.

Amines of the formula $R_1$—$S(O)_2$—$X_{1-2}$—O—$X_{1-1}$—$NH_2$ or salts thereof can be prepared using known synthetic methods. For example, the hydrochloride salt of $CH_3$—$S(O)_2$—$CH_2$—$CH_2$—O—$CH_2$—$CH_2$—$NH_2$ can be prepared by reacting sodium thiomethoxide with 2-{2-[(tert-butoxycarbonyl)amino]ethoxy}ethyl methanesulfonate followed by oxidation of the sulfur atom and removal of the tert-butoxycarbonyl group as described in Parts A-C of Example 1 infra.

In step (2) of Reaction Scheme I, a 3-nitroquinolin-4-amine of Formula XXVIII is reduced to provide a quinoline-3,4-diamine of Formula VII. The reduction can be carried out using a conventional heterogeneous hydrogenation catalyst such as platinum on carbon or palladium on carbon. The reaction can be conveniently carried out in a Parr vessel in a suitable solvent such as acetonitrile, toluene and/or isopropanol. The product or a pharmaceutically acceptable salt thereof can be isolated by conventional methods.

In step (3) of Reaction Scheme I, a quinoline-3,4-diamine of Formula VII is reacted with a carboxylic acid or an equivalent thereof to provide a 1H-imidazo[4,5-c]quinoline of Formula VIII. Suitable equivalents to a carboxylic acid include orthoesters, and 1,1-dialkoxyalkyl alkanoates. The carboxylic acid or equivalent is selected such that it will provide the desired $R_2$ substituent in a compound of Formula VI. For example, triethyl orthoformate will provide a compound with hydrogen at the 2-position, and trimethyl orthovalerate will provide a compound with butyl at the 2-position. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (3) can be carried out by (i) reacting a compound of Formula VII with an acyl halide of formula $R_2$—C(O)Cl or $R_2$—C(O)Br and then (ii) cyclizing. In part (i) the acyl halide is added to a solution of a compound of Formula VII in an inert solvent such as acetonitrile, pyridine or dichloromethane. The reaction can be carried out at ambient temperature. In part (ii) the product of part (i) is heated in pyridine or alternatively in an alcohol such as ethanol with a tertiary amine such as triethylamine. The two steps can be combined into a single step in solvents such as pyridine, dichloromethane, and dichloroethane.

In step (4a) of Reaction Scheme L a 1H-imidazo[4,5-c]quinoline of Formula VIII is oxidized to provide an N-oxide of Formula IX using a conventional oxidizing agent that is capable of forming N-oxides. The reaction can be conveniently carried out by treating a solution of a compound of Formula VIII in a suitable solvent such as chloroform or dichloromethane with 3-chloroperoxybenzoic acid at ambient temperature.

In step (4b) an N-oxide of Formula IX is aminated to provide a 1H-imidazo[4,5-c]quinolin-4-amine of Formula IIa-1, which is a subgenus of Formulas I, Ia, II, IIa, and IIb. The reaction is carried out in two parts. In part (i) a compound of Formula IX is reacted with an acylating agent. Suitable acylating agents include alkyl- or arylsulfonyl chorides (e.g., benesulfonyl chloride). In part (ii) the product of part (i) is reacted with an excess of an aminating agent. Suitable animenzenesulfonyl choride, methanesulfonyl choride, or p-toluating agents include ammonia (e.g. in the form of ammonium hydroxide) and ammonium salts (e.g., ammonium carenesulfonyl chloride). In part (ii) the product of part (i) is reacted with an excess of an aminating agent. Suitable animbonate, ammonium bicarbonate, ammonium phosphate). The reaction can be carried out by dissolving a compound of Formula IX in a suitable solvent such as dichloromethane or chloroform, adding ammonium hydroxide to the solution, and then adding p-toluenesulfonyl chloride. The product or a pharmaceutically acceptable salt thereof can be isolated using conventional methods.

Alternatively, in step (4), the oxidation of step (4a) and the amination of step (4b) can be carried out without isolating the product of the oxidation to provide a 1H-imidazo[4,5-c]quinolin-4-amine of Formula IIa-1. In step (4), after the 1H-imidazo[4,5-c]quinoline of Formula VIII is consumed by reaction with 3-chloroperoxybenzoic acid as described in step (4a), the aminating and acylating agents are added to the reaction mixture as described in step (4b) above. The product or a pharmaceutically acceptable salt thereof can be isolated using conventional methods.

Reaction Scheme I

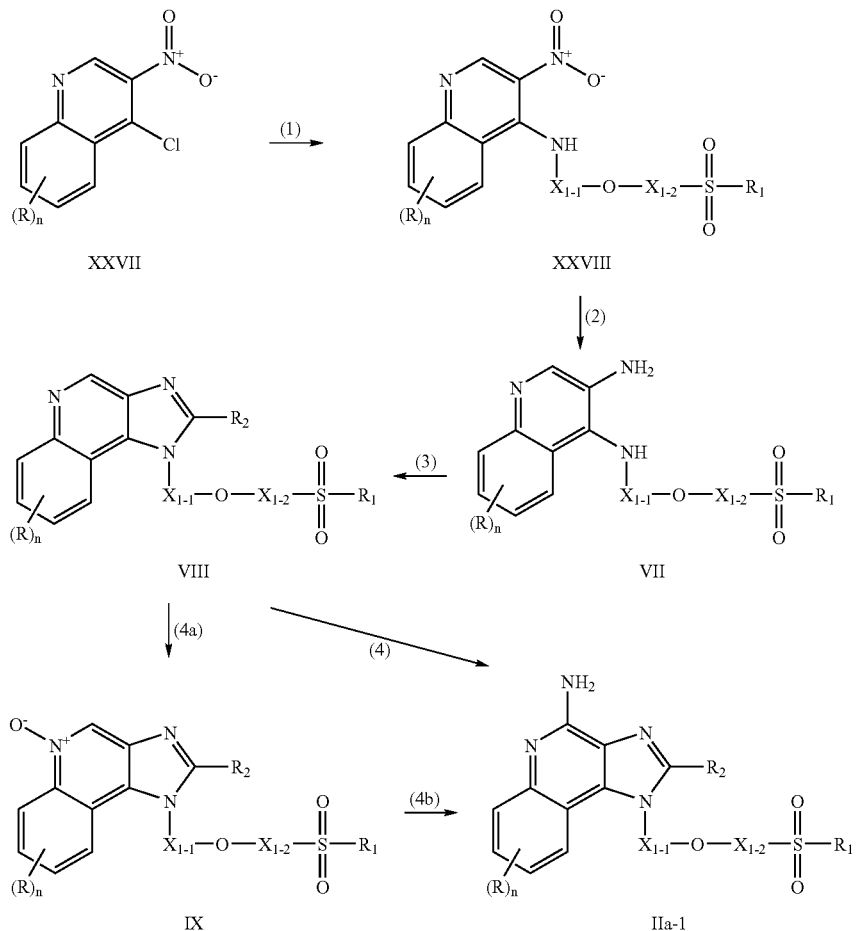

Compounds of the invention can be prepared according to Reaction Scheme II where R, $R_1$, $R_2$, $X_{1-1}$, and n are as defined above. In step (1) a 3-nitroquinolin-4-amine of Formula X is reduced to provide a quinoline-3,4-diamine of Formula XI. The reaction can be carried out as in step (2) of Reaction Scheme I. The product or a pharmaceutically acceptable salt thereof can be isolated by conventional methods. Many 3-nitroquinolin-4 amines of Formula X are known or can be prepared using known synthetic methods, see for example, U.S. Pat. Nos. 4,689,338; 5,175,296; and 5,389,640; and the references cited therein.

In step (2) of Reaction Scheme II, a quinoline-3,4-diamine of Formula XI is reacted with a carboxylic acid or an equivalent thereof to provide a 1H-imidazo[4,5-c]quinoline of Formula XII. The reaction can be conveniently carried out as described in step (3) of Reaction Scheme I. The product or a pharmaceutically acceptable salt thereof can be isolated by conventional methods.

In step (4) of Reaction Scheme II, a 1H-imidazo[4,5-c] quinoline of Formula XIII is oxidized to provide an N-oxide of Formula XIV. The reaction can be conveniently carried out as in step (4a) of Reaction scheme I.

In step (5) of Reaction Scheme II, an N-oxide of Formula XIV is aminated to provide a 1H-imidazo[4,5-c]quinolin-4-amine of Formula IIa-2, which is a subgenus of Formulas I, Ia, II, IIa, and IIb. The reaction is carried as in step (4b) of Reaction Scheme I. The product or a pharmaceutically acceptable salt thereof can be isolated by conventional methods.

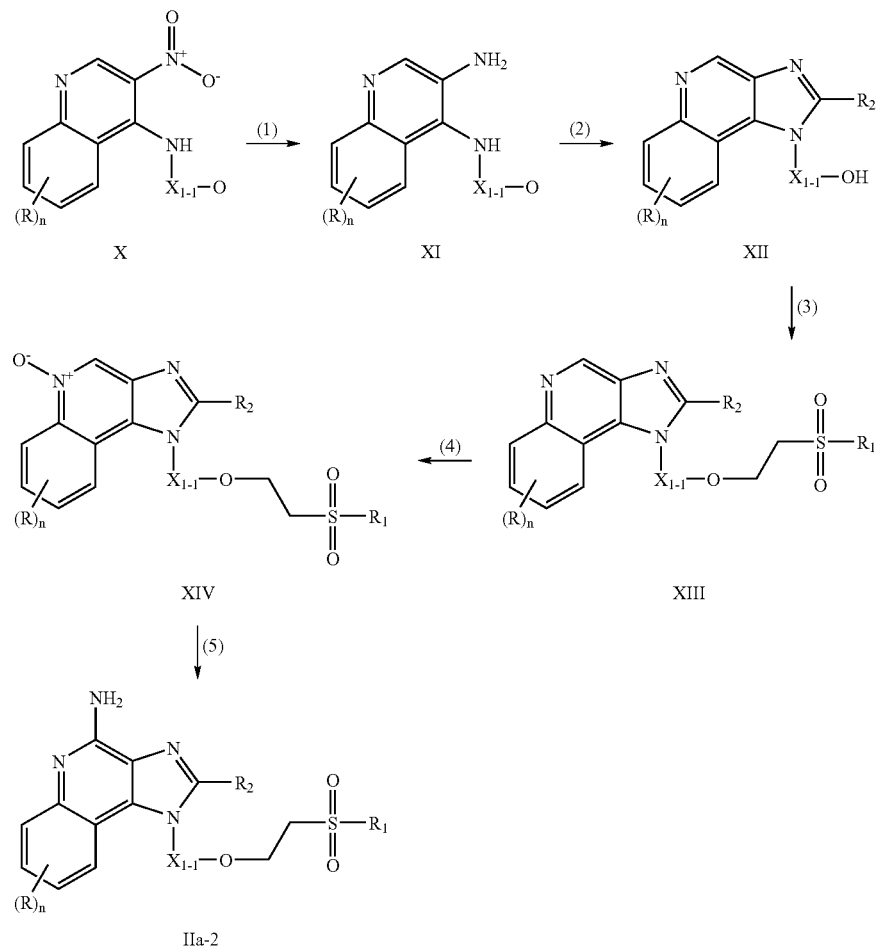

In step (3) of Reaction Scheme II, a 1H-imidazo[4,5-c] quinoline of Formula XII is reacted with sodium hydride to form an alkoxide, which is reacted with a vinyl sulfone of formula $CH_2=CH-S(O)_2-R_1$ to provide a 1H-imidazo[4,5-c]quinoline of Formula XIII. The reaction can be carried out by adding a substoichiometric amount of sodium hydride dispersed in mineral oil to a solution of a 1H-imidazo[4,5-c] quinoline of Formula XII and a vinyl sulfone of the formula $CH_2=CH-S(O)_2-R_1$ in a suitable solvent such DMF or tetrahydrofuran. The reaction can be run at ambient temperature. The product or a pharmaceutically acceptable salt thereof can be isolated by conventional methods. Many vinyl sulfones are commercially available or can be prepared using known synthetic methods.

Compounds of the invention can be prepared according to Reaction Scheme III where n is as defined above; $X_{1-1a}$ and $X_{1-2a}$ are independently $C_{1-10}$ alkylene; each $R_B$ is independently selected from the group consisting of hydroxyl, alkyl, alkoxy, and $-N(R_9)_2$; and $R_{1a}$ and $R_{2a}$ are a subset of $R_1$ and $R_2$, respectively, as defined above, which do not include those groups that one skilled in the art would recognize as being susceptible to reduction or decomposition under the mildly acidic conditions in step (1). These susceptible groups include, for example, alkenyl, alkynyl, and aryl groups, and groups bearing nitro and —S— substitutents.

In step (1) of Reaction Scheme III, a 1H-imidazo[4,5-c] quinolin-4-amine of Formula IIa-3 is reduced to provide a 6,7,8,9-tetrahydro-1H-imidazo[4,5-c]quinolin-4-amine of Formula IIIa-1, which is a subgenus of the Formulas I, Ia, III, IIIa, and IIIb. The reaction can be conveniently carried out by suspending or dissolving a compound of Formula IIa-3 in trifluoroacetic acid, adding a catalytic amount of platinum on carbon, and hydrogenating. The reaction can be carried out in a Parr apparatus. The product or a pharmaceutically acceptable salt thereof can be isolated using conventional methods.

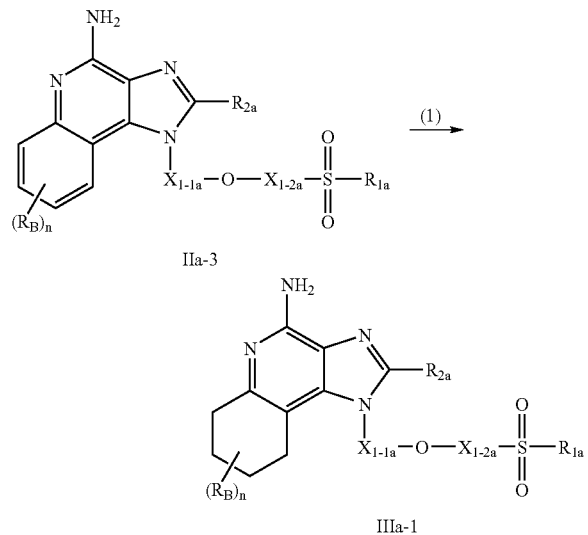

Reaction Scheme III

Compounds of the invention can be prepared according to Reaction Scheme IV where R, $R_1$, $R_2$, $X_{1-1}$, and n are as defined above; P is a protecting group such as, for example, tert-butoxycarbonyl; and Hal is chloro, bromo, or iodo. In step (1) the amino group of an amino alcohol of Formula XV is protected with a removable protecting group such as an alkoxycarbonyl group (e.g., tert-butoxycarbonyl) to provide a protected amine of Formula XVI. The reaction can be conveniently carried out by adding a base, such as aqueous sodium hydroxide, to a solution of the hydroxy amine of Formula XV in a suitable solvent such as tetrahydrofuran, and then adding tert-butyl dicarbonate. The product can be isolated by conventional methods.

In step (2) of Reaction Scheme IV, the hydroxy group of the protected amine of Formula XVI is alkylated with an allyl halide to provide an allyloxy compound of Formula XVII. The reaction can be conveniently carried out by combining the protected amine of Formula XVI with allyl bromide in a biphasic mixture of aqueous 50% sodium hydroxide in an inert solvent such as dichloromethane in the presence of a phase transfer catalyst such as benzyltrimethylammonium chloride. The reaction can be carried out at ambient temperature. The product can be isolated by conventional methods.

In step (3) of Reaction Scheme IV, the allyloxy compound of Formula XVII is hydroborated and oxidized to provide a hydroxypropoxy compound of Formula XVIII. The reaction is carried out by first adding 9-borabicyclo[3.3.1]nonane, dissolved in a suitable solvent such as tetrahydrofuran, to an allyloxy compound of Formula XVII, then adding water followed by aqueous sodium hydroxide, and then adding an excess of hydrogen peroxide. After completion of the reaction, excess peroxide can be neutralized with aqueous sodium metabisulfite. The product can be isolated by conventional methods.

In step (4) of Reaction Scheme IV, the amine protecting group on the hydroxypropoxy compound of Formula XVIII is removed to provide a hydroxypropoxy amine of Formula XIX. Removal of the tert-butoxycarbonyl protecting group can be conveniently carried out by adding hydrochloric acid in a solvent such as dioxane to the hydroxypropoxy compound of Formula XVIII.

In step (5) of Reaction Scheme IV, a hydroxypropoxy amine of Formula XIX or a salt thereof is reacted with a 4-chloro-3-nitroquinoline of Formula XXVII to provide a 3-nitroquinolin-4-amine of Formula XX. The reaction can be carried out by adding a 4-chloro-3-nitroquinoline to a solution of a hydroxpropoxy amine of Formula XIX or a salt thereof in a suitable solvent such as anhydrous dichloromethane in the presence of a base such as triethylamine. The reaction can be run at ambient temperature. The product or a pharmaceutically acceptable salt thereof can be isolated by conventional methods.

In step (6) of Reaction Scheme IV, the hydroxy group of a 3-nitroquinolin-4-amine of Formula XX is replaced with a halogen to provide a 3-nitroquinolin-4-amine of Formula XXI. The reaction can be carried out by adding thionyl chloride to a 3-nitroquinolin-4-amine of Formula XX in a suitable solvent such as dichloromethane. The reaction can be run at an elevated temperature, for example, at reflux. The product or a pharmaceutically acceptable salt thereof can be isolated by conventional methods.

In step (7) of Reaction Scheme IV, a 3-nitroquinolin-4-amine of Formula XXI is reduced to provide a quinoline-3,4-diamine of Formula XXI. The reduction can be carried out as in step (2) of Reaction Scheme I. The product or a pharmaceutically acceptable salt thereof can be isolated by conventional methods.

In step (8) of Reaction Scheme IV, a quinoline-3,4-diamine of Formula XXII is reacted with a carboxylic acid or an equivalent thereof to provide a 1H-imidazo[4,5-c]quinoline of Formula XXIII. The reaction can be carried out as in step (3) of Reaction Scheme I. The product or a pharmaceutically acceptable salt thereof can be isolated by conventional methods.

In step (9) of Reaction Scheme IV, a 1H-imidazo[4,5-c]quinoline of Formula XXIII is oxidized to a 5-N-oxide and then aminated to provide a 1H-imidazo[4,5-c]quinolin-4-amine of Formula XXIV. The reaction can be conveniently carried out as in step (4) or steps (4a) and (4b) of Reaction Scheme I. The product or a pharmaceutically acceptable salt thereof can be isolated using conventional methods.

In step (10) of Reaction Scheme IV, a 1H-imidazo[4,5-c]quinolin-4-amine of Formula XXV is reacted with a sodium thiolate of formula $Na^+S^-$—$R_1$ to provide a 1H-imidazo[4,5-c]quinolin-4-amine of Formula IIa-4, which is a subgenus of Formulas I, Ia, II, IIa, and IIb. The reaction can be carried out by adding a 1H-imidazo[4,5-c]quinolin-4-amine of Formula XXIV to a sodium thiolate of formula $Na^+S^-$—$R_1$ in a suitable solvent such as DMF. The reaction can be run at ambient temperature. The product or a pharmaceutically acceptable salt thereof can be isolated using conventional methods. Sodium thiolates of formula $Na^+S^-$—$R_1$ are commercially available or can be readily prepared by adding a thiol of formula HS—$R_1$ to a suspension of sodium hydride in a suitable solvent such as DMF.

In step (11) of Reaction Scheme IV, the sulfide moiety of a 1H-imidazo[4,5-c]quinolin-4-amine of Formula IIa-4 can be oxidized to a sulfinyl or sulfonyl moiety to provide a 1H-imidazo[4,5-c]quinolin-4-amine of Formula IIa-5, which is a subgenus of Formulas I, Ia, II, IIa, and IIb. The reaction can be carried out by treating a solution of a 1H-imidazo[4,5-c]quinolin-4-amine of Formula IIa-4 in a suitable solvent such as dichloromethane or chloroform with 3-chloroperoxybenzoic acid at ambient temperature. The degree of oxidation is controlled by adjusting the amount of 3-chloroperoxybenzoic acid used in the reaction. Using approximately one equivalent will provide the sulfinyl moiety, and using two equivalents will provide the sulfonyl moiety. The product or a pharmaceutically acceptable salt thereof can be isolated using conventional methods.

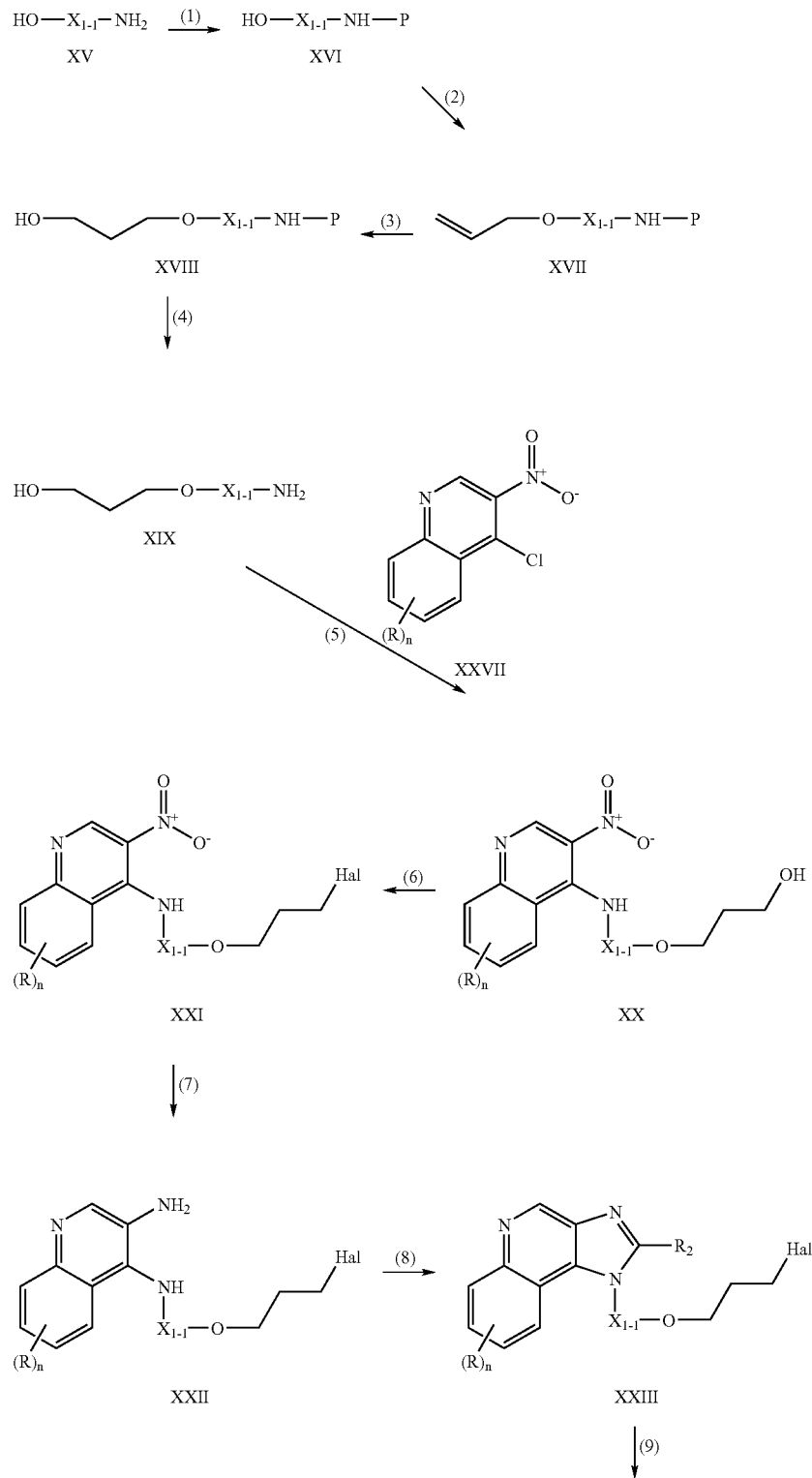

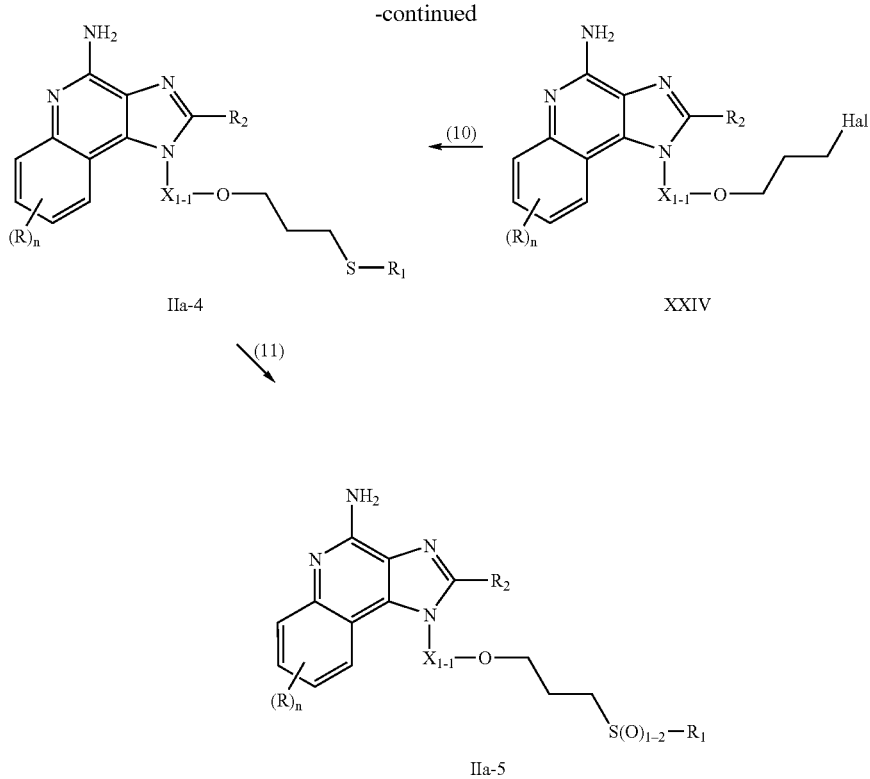

Compounds of the invention can be prepared according to Reaction Scheme V where $R_1$, $R_{2a}$, $R_B$, n, and $X_{1-1a}$ are as defined above. In step (1) a 1H-imidazo[4,5-c]quinolin-4-amine of Formula XXIVb is reduced to provide a 6,7,8,9-tetrahydro-1H-imidazo[4,5-c]quinolin-4-amine of Formula XXVI. The reaction can be carried out as in step (1) of Reaction Scheme III. The product or a pharmaceutically acceptable salt thereof can be isolated using conventional methods.

In step (2) of Reaction Scheme V, a 6,7,8,9-tetrahydro-1H-imidazo[4,5-c]quinolin-4-amine of Formula XXVI is reacted with a sodium thiolate of formula $Na^+S^-$—$R_1$ to provide a 6,7,8,9-tetrahydro-1H-imidazo[4,5-c]quinolin-4-amine of Formula IIIa-2, which is a subgenus of Formulas I, Ia, III, IIIa, and IIIb. The reaction can be carried out and sodium thiolates obtained as described in step (10) of Reaction Scheme IV. The product or a pharmaceutically acceptable salt thereof can be isolated using conventional methods.

In step (3) of Reaction Scheme V, a 6,7,8,9-tetrahydro-1-H-imidazo[4,5-c]quinolin-4-amine of Formula IIIa-2 can be oxidized to provide a 6,7,8,9-tetrahydro-1H-imidazo[4,5-c]quinolin-4-amine of Formula IIIa-3, which is a subgenus of Formulas I, Ia, II, IIIa, and IIIb. The reaction can be carried out as described in step (11) of Reaction Scheme IV. The product or a pharmaceutically acceptable salt thereof can be isolated using conventional methods.

Reaction Scheme V

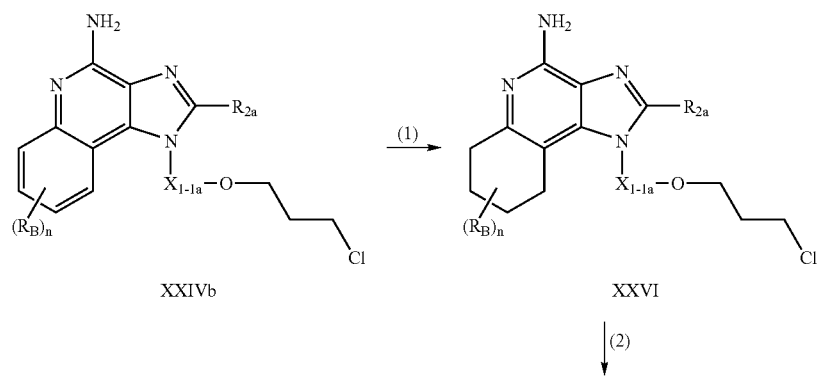

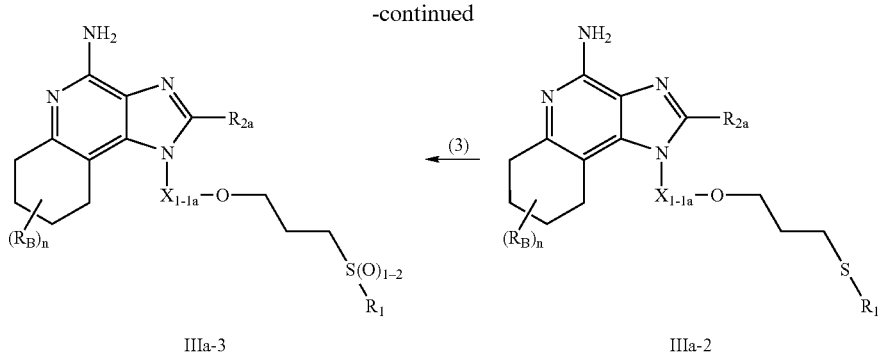

IIIa-3    IIIa-2

Compounds of the invention can be prepared according to Reaction Scheme VI where R, $R_1$, $R_2$, $X_{1-1}$, $X_{1-2}$, and m are as defined above. Reaction Scheme VI begins with a 4-chloro-3-nitro[1,5]naphthyridine of Formula XXIX. Compounds of Formula XXIX and their preparation are known; see for example U.S. Pat. No. 6,194,425 and the references cited therein. Steps (1) through (4) of Reaction Scheme VI can be carried out as described for the corresponding steps (1) through (4) of Reaction Scheme I to provide a 1H-imidazo[4,5-c][1,5]naphthyridine of Formula IVa-1, which is a subgenus of Formulas I, Ia, IV, and IVa. The product or a pharmaceutically acceptable salt thereof can be isolated using conventional methods.

Reaction Scheme VI

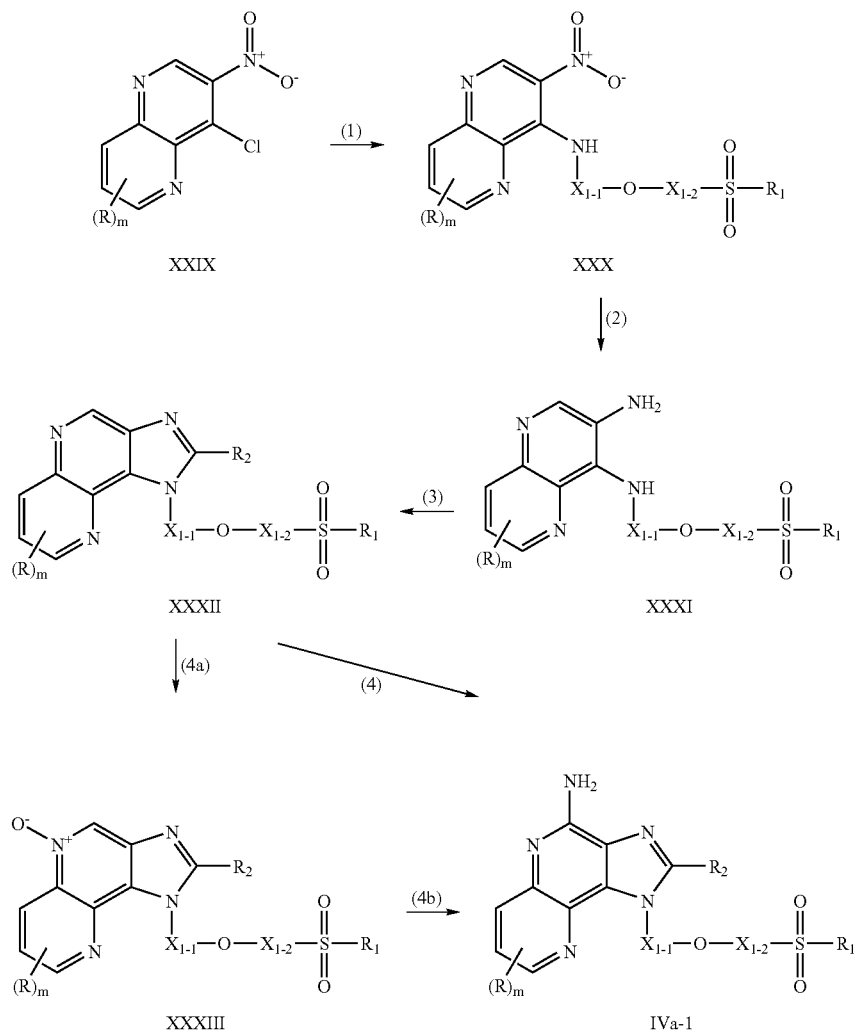

Compounds of the invention can be prepared according to Reaction Scheme VII where R, $R_1$, $R_2$, $X_{1-1}$, $X_{1-2}$, and m are as defined above and Ph is phenyl. Reaction Scheme VII begins with a 5-chloro-4-nitrotetrazolo[1,5-a][1,7]naphthyridine of Formula XXXIV. Compounds of Formula XXXIV can be prepared using the synthetic methods described in U.S. Pat. No. 6,194,425 and the references cited therein. Steps (1) through (3) of Reaction Scheme VII can be carried out as described for the corresponding steps (1) through (3) of Reaction Scheme VII to provide a 1H-tetrazolo[1,5-a]imidazo[4,5-c][1,7]naphthyridine of Formula XXXV.

In step (4) of Reaction Scheme VII, a 1H-tetrazolo[1,5-a]imidazo[4,5-c][1,7]naphthyridine of Formula XXXV is reacted with triphenylphosphine to form a N-triphenylphosphinyl intermediate of Formula XXXVI. The reaction can be carried out by combining a compound of Formula XXXV with triphenylphosphine under a nitrogen atmosphere in a suitable solvent such as toluene or 1,2-dichlorobenzene and heating at reflux.

In step (5) of Reaction Scheme VII, N-triphenylphosphinyl intermediate of Formula XXXVI is hydrolyzed to provide a 1H-imidazo[4,5-c][1,7]naphthyridine of Formula XXXVII, which is a subgenus of Formulas I and Ia. The hydrolysis can be carried out by general methods well known to those skilled in the art, for example, by heating in a lower alkanol in the presence of an acid. The product or a pharmaceutically acceptable salt thereof can be isolated using conventional methods.

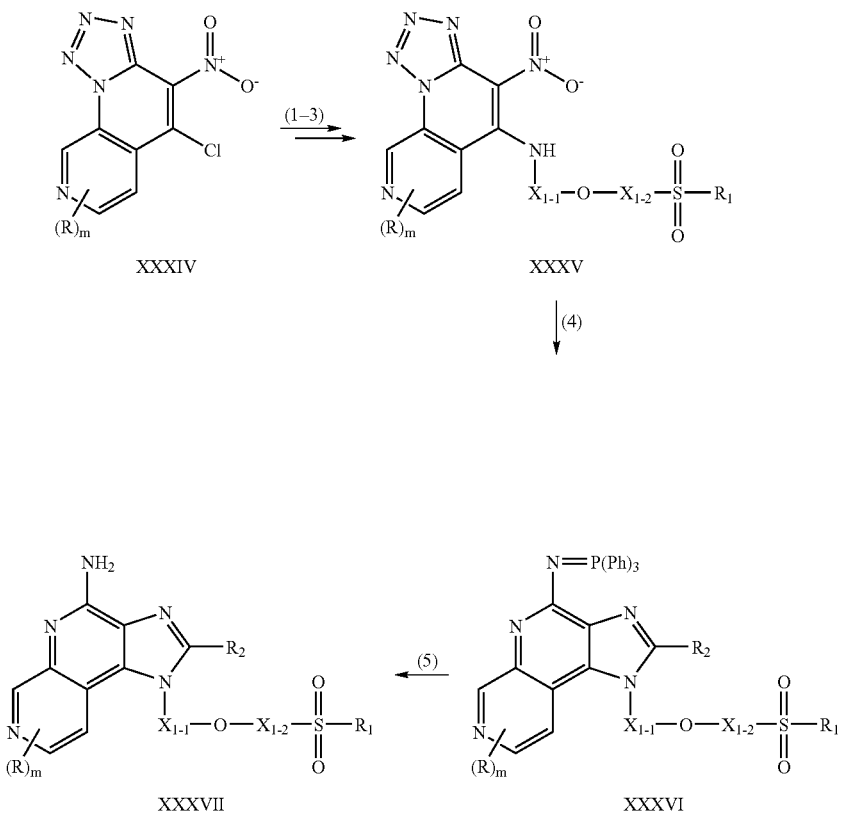

Reaction Scheme VII

Compounds of the invention can be prepared according to Reaction Scheme VIII where R, $R_1$, $R_2$, $X_{1-1}$, $X_{1-2}$, and m are as defined above, Ph is phenyl, and —Otf is a trifluoromethanesulfonate group. Reaction Scheme VIII begins with a 4-nitrotetrazolo[1,5-a][1,8]naphthyridine of Formula XXXVIII. Compounds of Formula XXXVIII can be prepared using the synthetic methods described in U.S. Pat. No. 6,194,425 and the references cited therein. Steps (1) through (5) of Reaction Scheme VIII can be carried out as described for the corresponding steps (1) through (5) of Reaction Scheme VII to provide a 1H-imidazo[4,5-c][1,8]naphthyridine of Formula XLI, which is a subgenus of Formulas I and Ia. The product or a pharmaceutically acceptable salt thereof can be isolated using conventional methods.

Reaction Scheme VIII

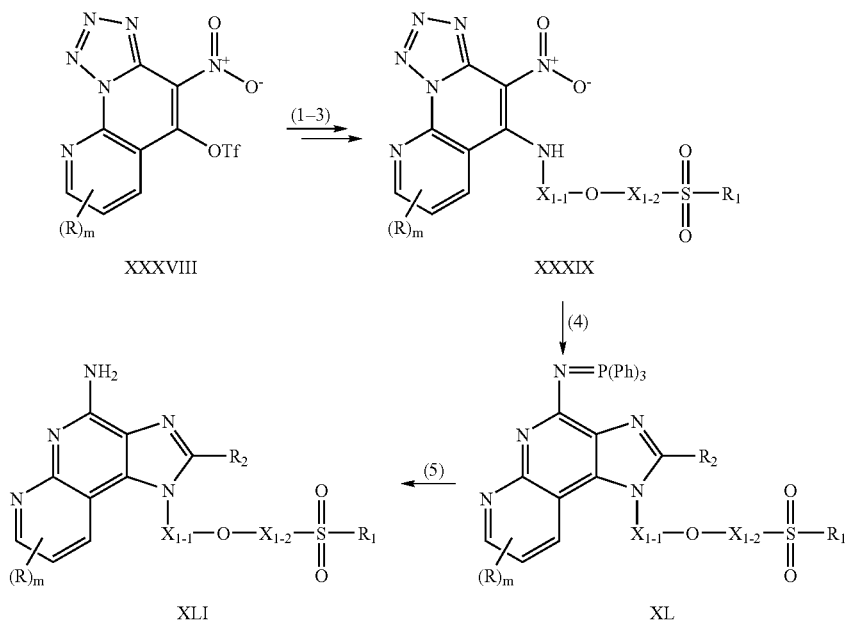

Compounds of the invention can also be prepared using variations of the synthetic routes shown in Reaction Schemes I through VIII. For example, the reduction method described in Reaction Scheme II for the preparation of tetrahydroquinolines can also be used to prepared tetrahydronaphthyridines and the synthetic route shown in Reaction Scheme IV for the preparation of quinolines can be used to prepare [1,5]naphthyridines by using a 4-chloro-3-nitro[1,5]naphthyridine in lieu of a 4-chloro-3-nitroquinoline. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the test set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomavirises, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, compounds or salts of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

Objects and advantages of this invention are further illustrated by the following examples, but the particular materials and amounts thereof recited in these examples, as well as other conditions and details, should not be construed to unduly limit this invention.

Example 1

2-Methyl-1-{2-[2-(methylsulfonyl)ethoxy]ethyl}-1H-imidazo[4,5-c]quinolin-4-amine

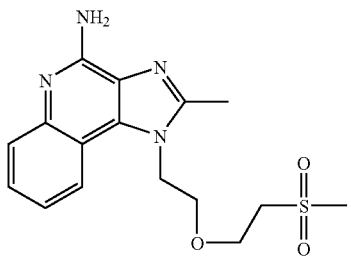

Part A

A suspension of 2-{2-[(tert-butoxycarbonyl)amino]ethoxy}ethyl methanesulfonate (28 g, 99 mmol) and sodium thiomethoxide (8.3 g, 119 mmol) in N,N-dimethylformamide (DMF, 200 mL) was heated to 80° C. and maintained at that temperature until analysis by thin layer chromatography (TLC) indicated that the starting material had been consumed. The reaction mixture was allowed to cool to ambient temperature and was then quenched with water (200 mL). The reaction mixture was extracted with diethyl ether (2×200 mL). The combined extracts were washed sequentially with saturated aqueous sodium bicarbonate (100 mL) and brine (100 mL), dried over anhydrous sodium sulfate, filtered, and then concentrated under reduced pressure to provide 22.5 g of tert-butyl 2-[2-(methylthio)ethoxy]ethylcarbamate as a light yellow oil.

Part B

A solution of the material from Part A in chloroform (478 mL) was placed in a cold water bath. Solid 3-chloroperoxybenzoic acid (45 g of ~60%) was added in portions over a period of 20 minutes. The reaction mixture was partitioned between chloroform (50 mL) and saturated aqueous sodium carbonate (100 mL). The organic layer was washed sequentially with saturated aqueous sodium carbonate (100 mL) and brine (100 mL), dried over anhydrous sodium sulfate, filtered, and then concentrated under reduced pressure to provide the crude product as a clear oil. The oil was purified by column chromatography (silica gel eluting sequentially with 1/1 ethyl acetate/hexanes and ethyl acetate) to provide 20.2 g of tert-butyl 2-[2-(methylsulfonyl)ethoxy]ethylcarbamate as a light yellow oil.

Part C

A solution of the material from Part B in methanol (22 mL) was chilled in an ice/water bath. Hydrochloric acid (94 mL of a 4M solution in dioxane) was added dropwise over a period of 22 minutes. The ice bath was removed and the reaction mixture was allowed to stir at ambient temperature for 45 minutes and then it was concentrated under reduced pressure. The residue was twice dissolved in methanol and then reconcentrated to provide 2-[2-(methylsulfonyl)ethoxy]ethaneamine hydrochloride as a clear oil.

Part D

Solid 4-chloro-3-nitroquinoline (14.2 g, 68.0 mmol) was added to a solution of the material from Part C (~75.6 mmol) in dichloromethane (226 mL) and triethylamine (28 mL). The reaction mixture was stirred at ambient temperature for 30 minutes and then additional 4-chloro-3-nitroquinoline (2 g) was added. After stirring at ambient temperature for 30 minutes the reaction mixture was concentrated under reduced pressure to provide a bright yellow solid. This material was suspended in water (400 mL) and then solid sodium carbonate was added until the pH reached ~10. The suspension was stirred for 1 hour. The solid was isolated by filtration and then washed with water to provide 17.9 g of N-{2-[2-(methylsulfonyl)ethoxy]ethyl}-3-nitroquinolin-4-amine as a bright yellow powder.

Part E

Solid Pt/C (0.9 g of 5%) was added to a suspension of N-{2-[2-(methylsulfonyl)ethoxy]ethyl}-3-nitroquinolin-4-amine (9 g, 26.5 mmol) in acetonitrile (133 mL) in a Parr vessel. The vessel was placed on a shaker and then pressurized with hydrogen to 50 psi (3.4×10$^5$ Pa). After 3 hours the reaction mixture was purged with nitrogen and then filtered through a layer of CELITE filter agent. The filter cake was washed with acetonitrile (200 mL) until the washes were clear. The filtrate was concentrated under reduced pressure to provide $N^4$-{2-[2-(methylsulfonyl)ethoxy]ethyl}quinoline-3,4-diamine as a yellow oil.

Part F

Trimethyl orthoacetate (1 g, 8.1 mmol) was added to a mixture of $N^4$-{2-[2-(methylsulfonyl)ethoxy]ethyl}quinoline-3,4-diamine (~2.3 g, ~7.4 mmol) and toluene (45 mL). Pyridine hydrochloride (0.25 g) was added and the reaction mixture was heated to reflux with the volatiles being collected in a Dean Stark trap. Pyridine was added to help solubilize the starting material. After 2 hours the reaction mixture was concentrated under reduced pressure to provide a dark oil. This material was purified by column chromatography (silica gel eluting sequentially with 95/5 dichloromethane/methanol and 9/1 dichloromethane/methanol) to provide 1.75 g of 2-methyl-1-{2-[2-(methylsulfonyl)ethoxy]ethyl}-1H-imidazo[4,5-c]quinoline as a white foam.

Part G

3-Chloroperoxybenzoic acid (1.5 g of ~60%, 5.3 mmol) was added in portions over a period of 8 minutes to a solution of the material from Part F (5.3 mmol) in chloroform (53 mL). The reaction mixture was stirred at ambient temperature for 20 minutes during which time a precipitate formed. The suspension was diluted with chloroform (100 mL) and saturated aqueous sodium carbonate (50 mL) and then filtered to provide 2-methyl-1-{2-[2-(methylsulfonyl)ethoxy]ethyl}-1H-imidazo[4,5-c]quinoline 5-oxide as a white solid. The crude wet material was carried on to the next step.

Part H

The material from Part G was suspended in dichloromethane (26 mL). Ammonium hydroxide (9 mL, 28% solution in water) was added. Para-toluenesulfonyl chloride (1.0 g, 5.3 mmol) was added. After stirring at ambient temperature for 30 minutes the reaction mixture was filtered. Analysis (H NMR) of the isolated solid showed a 2:1 mixture of desired product to N-oxide. The crude material was subjected to additional amination using the same reaction conditions. The product was isolated by filtration, washed with water, and dried at 65° C. for 2 hours to provide 0.7 g of 2-methyl-1-{2-[2-(methylsulfonyl)ethoxy]ethyl}-1H-imidazo[4,5-c]quinolin-4-amine as a white powder, mp 214-217° C. $^1$H NMR (300 MHz, DMSO-$d_6$) δ 8.04 (d, J=8.1 Hz, 1H), 7.57 (d, J=8.0 Hz, 1H), 7.41 (t, J=8.0 Hz, 1H), 7.22 (t, J=8.0 Hz, 1H), 6.46 (bs, 2H), 4.73 (t, J=5.1 Hz, 2H), 3.91 (t, J=5.1 Hz, 2H), 3.72 (t, J=5.6 Hz, 2H), 3.29 (t, J=5.6 Hz, 2H), 2.76 (s, 3H), 2.60 (s, 3H); MS (APCI) m/z 349 (M+H)$^+$; Anal. Cacld for C$_{16}$H$_{20}$N$_4$O$_3$S: C, 55.16; H, 5.79: N, 16.08. Found: C, 54.89; H, 5.69; N, 15.85.

Example 2

2-Butyl-1-{2-[2-(methylsulfonyl)ethoxy]ethyl}-1H-imidazo[4,5-c]quinolin-4-amine

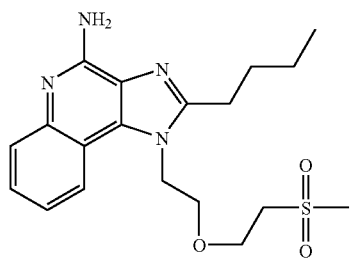

Part A

Trimethyl orthovalerate (1.3 g, 8.1 mmol) was added to a solution of N$^4$-{2-[2-(methylsulfonyl)ethoxy]ethyl}quinoline-3,4-diamine (~2.3 g, ~7.4 mmol) in acetonitrile (37 mL). Pyridine hydrochloride (~100 mg) was added and the reaction mixture was heated to reflux with the volatiles being collected in a Dean Stark trap. After 15 minutes analysis by TLC indicated that the starting material was consumed. The reaction mixture was cooled and then concentrated under reduced pressure to provide ~2.8 g of 2-butyl-1-{2-[2-(methylsulfonyl)ethoxy]ethyl}-1H-imidazo[4,5-c]quinoline as a greenish-yellow powder.

Part B

Solid 3-chloroperoxybenzoic acid (2.1 g of ~60%) was added in portions over a period of 3 minutes to a solution of 2-butyl-1-{2-[2-(methylsulfonyl)ethoxy]ethyl}-1H-imidazo[4,5-c]quinoline (2.7 g, 7.2 mmol) in chloroform (72 μL). The reaction mixture was stirred at ambient temperature for 30 minutes then additional 3-chloroperoxybenzoic acid (0.4 g) was added. The reaction mixture was stirred at ambient temperature for 15 minutes and then partitioned between dichloromethane (100 mL) and saturated aqueous sodium carbonate (50 mL). The organic layer was washed sequentially with saturated aqueous sodium carbonate (50 mL) and brine (50 mL), dried over anhydrous sodium sulfate, filtered, and then concentrated under reduced pressure to provide 2-butyl-1-{2-[2-(methylsulfonyl)ethoxy]ethyl}-1H-imidazo[4,5-c]quinoline 5-oxide as an orange foam.

Part C

Aqueous ammonium hydroxide (12 mL, 30% solution in water) was added to a rapidly stirred solution of the material from Part B in dichloromethane (36 mL). Para-toluenesulfonyl chloride (1.4 g, 7.2 mmol) was added. The reaction mixture was stirred at ambient temperature until analysis by TLC showed that the starting material had been consumed. The reaction mixture was partitioned between chloroform (100 mL) and saturated aqueous sodium carbonate (50 mL). The organic layer was washed sequentially with saturated aqueous sodium carbonate (50 mL) and brine (50 ml), dried over anhydrous sodium sulfate, filtered, and then concentrated under reduced pressure to provide a yellow solid. This material was purified by column chromatography (silica gel eluting sequentially with 95/5 dichloromethane/methanol and 9/1 dichloromethane/methanol) to provide 1.6 g of a white powder. The powder was recrystallized from acetonitrile. Peach needles were isolated by filtration, washed with acetonitrile, and dried under vacuum at 65° C. for 4 hours to provide 1.3 g of 2-butyl-1-{2-[2-(methylsulfonyl)ethoxy]ethyl}-1H-imidazo[4,5-c]quinolin-4-amine, mp 168-170° C. $^1$H NMR (300 MHz, DMSO-d$_6$) δ 8.04 (d, J=8.1 Hz, 1H), 7.60 (d, J=8.0 Hz, 1H), 7.41 (t, J=8.0 Hz, 1H), 7.23 (t, J=8.0 Hz, 1H), 6.42 (bs, 2H), 4.74 (t, J=5.1 Hz, 2H), 3.90 (t, J=5.1 Hz, 2H), 3.72 (t, J=5.6 Hz, 2H), 3.28 (t, J=5.6 Hz, 2H), 2.93 (t, J=7.6 Hz, 2H), 2.76 (s, 3H), 1.80 (pentet, J=7.6 Hz, 2H), 1.45 (sextet, J=7.6 Hz, 2H), 0.96 (t, J=7.6 Hz, 3H); MS (APCI) m/z 391 (M+H)$^+$; Anal. Cacld for C$_{19}$H$_{26}$N$_4$O$_3$S: C, 58.44; H, 6.71: N, 14.35. Found: C, 58.43; H, 6.84; N, 14.31.

Example 3

1-{2-[2-(Methylsulfonyl)ethoxy]ethyl}-1H-imidazo[4,5-c]quinolin-4-amine

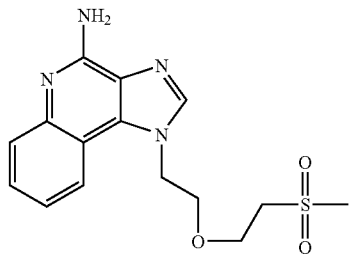

Part A

Triethyl orthoformate (2 mL, 12 mmol) was added to a stirred solution of N$^4$-{2-[2-(methylsulfonyl)ethoxy]ethyl}quinoline-3,4-diamine (3.1 g, 10 mmol) in acetonitrile (50 mL). Pyridine hydrochloride (0.3 g) was added and the reaction mixture was heated to reflux with the volatiles being collected in a Dean Stark trap. After 20 minutes analysis by TLC indicated that the starting material was consumed. The reaction mixture was concentrated under reduced pressure to provide a viscous oil. The oil was triturated with ethyl acetate. The resulting solid was isolated by filtration and washed with ethyl acetate to provide 2.17 g of 1-{2-[2-(methylsulfonyl)ethoxy]ethyl}-1H-imidazo[4,5-c]quinoline as an off-white powder.

Part B

3-Chloroperoxybenzoic acid (2.15 g of 60%, 7.47 mmol) was added over a period of 10 minutes to a suspension of the material from Part A (6.79 mmol) in chloroform (34 mL). After 20 minutes analysis by TLC indicated that the starting material had been consumed. Ammonium hydroxide (34 mL, 28% solution in water) was added. The resulting biphasic mixture was homogenized by stirring for several minutes. Para-toluenesulfonyl chloride (1.4 g, 7.5 mmol) was added in a single portion. The reaction mixture was stirred at ambient temperature for 15 minutes. The reaction mixture was poured into a separatory funnel and the layers were separated. The aqueous layer was extracted with chloroform. The combined organics were washed with brine (50 mL), dried over anhydrous sodium sulfate, filtered, and then concentrated under reduced pressure to provide an orange oil. The oil was purified by column chromatography (silica gel eluting with 95/5 dichloromethane/methanol) to provide a foam. This material was combined with ethyl acetate, heated at reflux, and then stirred at ambient temperature for 14 hours. The resulting crystalline white solid was isolated by filtration, washed with ethyl acetate, and dried under vacuum at 65° C. overnight to provide 0.4 g of 1-{2-[2-(methylsulfonyl)ethoxy]ethyl}-1H-imidazo[4,5-c]quinolin-4-amine, mp 145-148° C. $^1$H NMR (300 MHz, DMSO-d$_6$) δ 8.14 (s, 1H), 8.08 (d, J=8.1 Hz, 1H), 7.62 (d, J=8.0 Hz, 1H), 7.44 (t, J=8.0 Hz, 1H), 7.24 (t, J=8.0 Hz, 1H), 6.58 (bs, 2H), 4.82 (t, J=5.0 Hz, 2H), 3.93 (t, J=5.0 Hz, 2H), 3.77 (t, J=5.6 Hz, 2H), 3.30 (t, J=5.6 Hz, 2H), 2.80 (s, 3H); MS (APCI) m/z 335 (M+H)$^+$; Anal. Cacld for C$_{15}$H$_{18}$N$_4$O$_3$S. 0.25H$_2$O: C, 53.16; H, 5.50: N, 16.53. Found: C, 52.83; H, 5.36; N, 16.67.

Example 4

1-{2-[2-(Methylsulfonyl)ethoxy]ethyl}-2-propyl-1H-imidazo[4,5-c]quinolin-4-amine

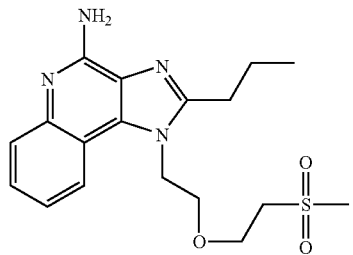

Part A

Triethyl orthobutyrate (2.2 mL, 14 mmol) was added to a stirred solution of N$^4$-{2-[2-(methylsulfonyl)ethoxy]ethyl}quinoline-3,4-diamine (3.6 g, 12 mmol) in acetonitrile (60 mL). Pyridine hydrochloride (0.3 g) was added and the reaction mixture was heated to reflux with the volatiles being collected in a Dean Stark trap. After 40 minutes analysis by TLC indicated that the starting material was consumed. The reaction mixture was concentrated under reduced pressure to provide 3.7 g of 1-{2-[2-(methylsulfonyl)ethoxy]ethyl}-2-propyl-1H-imidazo[4,5-c]quinoline as a white solid.

Part B

3-Chloroperoxybenzoic acid (3.24 g of 60%, 11.3 mmol) was added in portions to a solution of the material from Part A (10.2 mmol) in chloroform (51 mL) over a period of 8 minutes. After 20 minutes analysis by TLC indicated that the starting material was consumed. The reaction mixture was partitioned between chloroform (100 mL) and saturated aqueous sodium carbonate (100 mL). The aqueous layer was extracted with chloroform (50 mL). The combined organics were washed with brine (50 mL), dried over anhydrous sodium sulfate, filtered, and concentrated under reduced pressure to provide 1-{2-[2-(methylsulfonyl)ethoxy]ethyl}-2-propyl-1H-imidazo[4,5-c]quinoline 5-oxide as an orange foam.

Part C

Ammonium hydroxide (17 mL, 28% solution in water) was added to a solution of the material from Part B in dichloromethane (51 mL). The resulting biphasic mixture was stirred vigorously while para-toluenesulfonyl chloride (1.94 g, 10.2 mmol) was added in portions over a period of 3 minutes. After 10 minutes analysis by TLC indicated that all of the starting material had been consumed. The reaction mixture was partitioned between chloroform (100 mL) and saturated aqueous sodium carbonate (50 mL). The organic layer was washed sequentially with saturated aqueous sodium carbonate (50 mL) and with brine (50 mL), dried over anhydrous sodium sulfate, filtered, and concentrated under reduced pressure to provide crude product as an orange foam. This material was recrystallized sequentially from acetonitrile and ethanol and then purified by column chromatography (silica gel eluting with 95/5 dichloromethane/methanol) to provide 1.8 g of a white solid. This material was recrystalized from ethanol. The resulting white needles were isolated by filtration and washed with ethanol to provide 1.6 g of a white crystalline solid. This material was suspended in water (15 mL). Hydrochloric acid was added (0.7 mL of 12M solution in water). The solid went into solution but then precipitated back out of solution. The pH was adjusted to 12 by adding sodium hydroxide (20% solution in water). The solid was isolated by filtration, washed with water, and dried under vacuum at 65° C. overnight to provide 1.0 g of 1-{2-[2-(methylsulfonyl)ethoxy]ethyl}-2-propyl-1H-imidazo[4,5-c]quinolin-4-amine as a white powder, mp 150-152° C. $^1$H NMR (300 MHz, DMSO-d$_6$) δ 8.04 (d, J=8.1 Hz, 1H), 7.62 (d, J=8.1 Hz, 1H), 7.41 (t, J=8.1 Hz, 1H), 7.23 (t, J=8.1 Hz, 1H), 6.44 (bs, 2H), 4.74 (t, J=5.0 Hz, 2H), 3.90 (t, J=5.0 Hz, 2H), 3.72 (t, J=5.6 Hz, 2H), 3.28 (t, J=5.6 Hz, 2H), 2.92 (t, J=7.6 Hz, 2H), 2.77 (s, 3H), 1.84 (sextet, J=7.6 Hz, 2H), 1.03 (t, J=7.6 Hz, 3H); MS (APCI) m/z 377 (M+H)$^+$; Anal. Cacld for C$_{18}$H$_{24}$N$_4$O$_3$S: C, 57.43; H, 6.43: N, 14.88. Found: C, 57.37; H, 6.50; N, 14.85.

Example 5

2-Ethyl-1-{2-[2-(methylsulfonyl)ethoxy]ethyl}-1H-imidazo[4,5-c]quinolin-4-amine

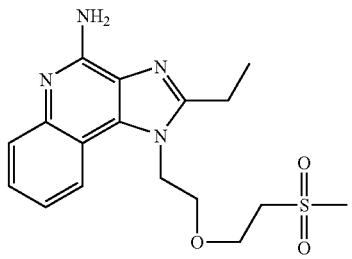

Part A

Triethyl orthopropionate (2.5 mL, 12 mmol) was added to a stirred solution of N$^4$-{2-[2-(methylsulfonyl)ethoxy]ethyl}quinoline-3,4-diamine (3.2 g, 10 mmol) in acetonitrile (50 mL). Pyridine hydrochloride (0.3 g) was added and the reaction mixture was heated to reflux with the volatiles being collected in a Dean Stark trap. After 40 minutes analysis by TLC indicated that the starting material was consumed. The reaction mixture was concentrated under reduced pressure to provide 3.2 g of 2-ethyl-1-{2-[2-(methylsulfonyl)ethoxy]ethyl}-1H-imidazo[4,5-c]quinoline as an oil which slowly solidified.

Part B

Using the method of Example 4 Part B, the material from Part A was oxidized to provide 2-ethyl-1-{2-[2-(methylsulfonyl)ethoxy]ethyl}-1H-imidazo[4,5-c]quinoline 5-Oxide as an orange solid.

Part C

Using the method of Example 4 Part C the material from Part B was aminated and purified to provide 0.8 g of 2-ethyl-1-{2-[2-(methylsulfonyl)ethoxy]ethyl}-1H-imidazo[4,5-c]quinolin-4-amine as a white powder, mp 160-163° C. $^1$H NMR (300 MHz, DMSO-d$_6$) δ 8.04 (d, J=8.1 Hz, 1H), 7.62 (d, J=8.1 Hz, 1H), 7.41 (t, J=8.1 Hz, 1H), 7.23 (t, J=8.1 Hz, 1H), 6.44 (bs, 2H), 4.73 (t, J=5.0 Hz, 2H), 3.90 (t, J=5.0

2H), 3.72 (t, J=5.6 Hz, 2H), 3.28 (t, J=5.6 Hz, 2H), 2.97 (q, J=7.5 Hz, 2H), 2.76 (s, 3H) 1.36 (t, J=7.5 Hz, 3H); MS (APCI) m/z 363 (M+1)+; Anal. Cacld for $C_{17}H_{22}N_4O_3S$: C, 56.33; H, 6.12: N, 15.46. Found: C, 56.16; H, 5.99; N, 15.37.

Example 6

2-(Ethoxymethyl)-1-{2-[2-(methylsulfonyl)ethoxy]ethyl}-1H-imidazo[4,5-c]quinolin-4-amine

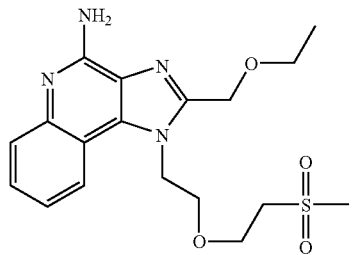

Part A

Ethoxyacetyl chloride (1.26 g, 10.6 mmol) was added dropwise to a stirred solution of $N^4$-{2-[2-(methylsulfonyl)ethoxy]ethyl}quinoline-3,4-diamine (3.0 g, 9.7 mmol) in acetonitrile (48 mL). A precipitate formed after the addition was complete. The reaction was stirred at ambient temperature over the weekend. The precipitate was isolated by filtration and washed with acetonitrile to provide 3.4 g of the hydrochloride salt of 2-ethoxy-N-[4-({2-[2-(methylsulfonyl)ethoxy]ethyl}amino)quinolin-3-yl]acetamide as a white powder.

Part B

A solution of the material from Part A (3.33 g, 8.42 mmol) in ethanol (42 mL) and triethylamine (3.5 mL, 25.3 mmol) was heated at reflux for 2 hours. Analysis by TLC showed that the starting material had been consumed. The reaction mixture was allowed to cool and then it was concentrated under reduced pressure. The residue was combined with water (50 mL) and then extracted with dichloromethane (2×100 mL). The combined extracts were washed with brine (50 mL), dried over anhydrous sodium sulfate, filtered, and concentrated under reduced pressure to provide crude product as a light yellow oil. This material was purified by column chromatography (silica gel eluting with 95/5 dichloromethane/methanol) to provide 2.6 g of 2-(ethoxymethyl)-1-{2-[2-(methylsulfonyl)ethoxy]ethyl}-1H-imidazo[4,5-c]quinoline as an oil which slowly solidified.

Part C

3-Chloroperoxybenzoic acid (2.2 g of 60%, 7.6 mmol) was added in portions to a solution of the material from Part B (6.9 mmol) in chloroform (34 mL) over a period of 8 minutes. After 20 minutes analysis by TLC indicated that the starting material was consumed. Ammonium hydroxide (34 mL, 30% solution in water) was added. The resulting biphasic mixture was stirred until both phases were clear and red. Solid para-toluenesulfonyl chloride (1.3 g, 6.6 mmol) was added in several portions. The reaction mixture was stirred at ambient temperature. After 10 minutes analysis by TLC indicated that the starting material was consumed. The reaction mixture was partitioned between dichloromethane (100 mL) and saturated aqueous sodium carbonate (50 mL). The organic layer was washed sequentially with saturated aqueous sodium carbonate (50 mL) and with brine (50 mL), dried over anhydrous sodium sulfate, filtered, and concentrated under reduced pressure to provide crude product. The crude product was purified by column chromatography (silica gel eluting with 95/5 dichloromethane/methanol) to provide a light brown foam. This material was dissolved in hot methanol (50 mL). The solution was treated with activated charcoal (1 g of DARCO) and then filtered though a layer of CELITE filter aid. The filter cake was rinsed with warm methanol and the filtrate was concentrated under reduced pressure to provide a white foam. This material was recrystallized from ethanol. The resulting solid was isolated by filtration, washed with ethanol, and dried under vacuum at 65° C. for 4 hours to provide 0.75 g of 2-(ethoxymethyl)-1-{2-[2-(methylsulfonyl)ethoxy]ethyl}-1H-imidazo[4,5-c]quinolin-4-amine as crystalline plates, mp 158-160° C. $^1H$ NMR (300 MHz, DMSO-$d_6$) δ 8.09 (d, J=8.7 Hz, 1H), 7.62 (d, J=8.7 Hz, 1H), 7.45 (t, J=8.1 Hz, 1H), 7.25 (t, J=8.1 Hz, 1H), 6.60 (bs, 2H), 4.85 (t, J=5.0 Hz, 2H), 4.80 (s, 2H), 3.92 (t, J=5.0 Hz, 2H), 3.75 (t, J=5.6 Hz, 2H), 3.56 (q, J=6.9 Hz, 2H), 3.30 (t, J=5.6 Hz, 2H), 2.77 (s, 3H) 1.17 (t, J=6.9 Hz, 3H); MS (APCI) m/z 393 (M+H)+; Anal. Cacld for $C_{18}H_{24}N_4O_4S$: C, 55.09; H, 6.16: N, 14.28. Found: C, 54.91; H, 6.04; N, 14.15.

Example 7

2-(2-Methoxyethyl)-1-{2-[2-(methylsulfonyl)ethoxy]ethyl}-1H-imidazo[4,5-c]quinolin-4-amine

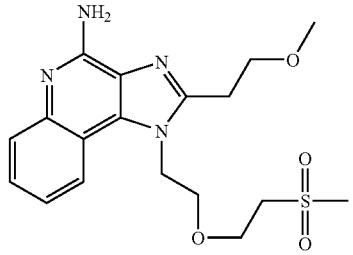

Part A

Using the method of Example 6 Part A, $N^4$-{2-[2-(methylsulfonyl)ethoxy]ethyl}quinoline-3,4-diamine (2.9 g, 9.3 mmol) was reacted with 3-methoxypropionyl chloride (1.26 g, 10.3 mmol) to provide 3.5 g of the hydrochloride salt of 3-methoxy-N-[4-({2-[2-(methylsulfonyl)ethoxy]ethyl}amino)quinolin-3-yl]propanamide.

Part B

Using the method of Example 6 Part B, except that the reaction mixture was heated at reflux for 10 hours, the material from Part A was cyclized to provide 2.0 g of 2-(methoxyethyl)-1-{2-[2-(methylsulfonyl)ethoxy]ethyl}-1H-imidazo[4,5-c]quinoline as an oil which slowly solidified.

Part C

Using the method of Example 6 Part C, the material from Part B was oxidized and then aminated. The crude material was purified by column chromatography (silica gel eluting with 95/5 dichloromethane/methanol) and then recrystallized from ethanol. The resulting solid was isolated by filtration, washed with ethanol, and dried under vacuum at 65° C. for 4 hours to provide 0.5 g of 2-(2-methoxyethyl)-1-{2-[2-(methylsulfonyl)ethoxy]ethyl}-1H-imidazo[4,5-c]quinolin-4-amine as orange needles, mp 142-144° C. $^1H$ NMR (300 MHz, DMSO-$d_6$) δ 8.06 (d, J=8.1 Hz, 1H), 7.62 (d, J=8.1 Hz, 1H), 7.42 (t, J=8.1 Hz, 1H), 7.23 (t, J=8.1 Hz, 1H), 6.47 (bs, 2H), 4.78 (t, J=5.1 Hz, 2H), 3.90 (t, J=5.1 Hz, 2H), 3.83 (t, J=6.9 Hz, 2H), 3.72 (t, J=5.6 Hz, 2H), 3.32-3.26 (m, 5H), 3.21

(t, J=6.9 Hz, 2H) 2.76 (s, 3H); MS (APCI) m/z 393 (M+H)+; Anal. Cacld for $C_{18}H_{24}N_4O_4S$: C, 55.09; H, 6.16: N, 14.28. Found: C, 54.96; H, 6.44; N, 14.10.

Example 8

2-Ethoxymethyl-1-{2-[2-(phenylsulfonyl)ethoxy]-2-methylpropyl}-1H-imidazo[4,5-c]quinolin-4-amine

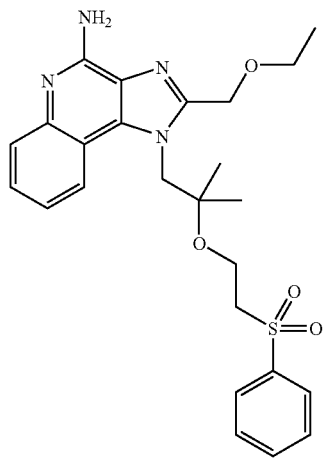

Part A

Solid Pt/C (0.7 g of 5%) was added to a suspension of N-(2-hydroxy-2-methylpropyl)-3-nitroquinolin-4-amine (7 g, 26.8 mmol) in acetonitrile (134 mL) in a Parr vessel. The vessel was placed on a shaker and then pressurized with hydrogen to 50 psi ($3.4 \times 10^5$ Pa). After 17 hours the reaction mixture was purged with nitrogen and then filtered through a layer of CELITE filter agent. The filter cake was washed with acetonitrile (200 mL) until the washes were clear. The filtrate was concentrated under reduced pressure to provide crude material as a yellow oil.

Part B

Ethoxyacetyl chloride (4 g, 30 mmol) was added dropwise to a stirred solution of the material from Part A in acetonitrile (134 mL). A precipitate formed after the addition was complete. The reaction was stirred at ambient temperature for 1 hour. The precipitate was isolated by filtration and washed with acetonitrile to provide crude product which contained both starting material and 2-ethoxy-N-{4-[(2-hydroxy-2-methylpropyl)amino]quinolin-3-yl}acetamide. This crude mixture was carried on to the next step without additional purification.

Part C

A warm solution of sodium hydroxide (1.3 g) in water (10 mL) was added dropwise to a suspension of the material from Part B in ethanol (29 mL). After the addition was completed the reaction mixture was heated to reflux. After 45 minutes analysis by TLC indicated that the amide intermediate had been consumed. The reaction mixture was cooled and then concentrated under reduced pressure. The residue was diluted with water (100 mL) and then extracted with dichloromethane (2×100 mL). The extracts were combined, washed with brine (100 mL), dried over anhydrous sodium sulfate, filtered, and concentrated under reduced pressure to provide crude product as a brown oil. This material was purified by column chromatography (silica gel eluting with 95/5 dichloromethane/methanol) to provide 4.5 g of 1-(2-ethoxymethyl-1H-imidazo[4,5-c]quinolin-1-yl)-2-methylpropan-2-ol as a colorless oil which slowly solidified.

Part D

Solid sodium hydride (30 mg of 60% dispersion in mineral oil, 0.72 mmol) was added to a stirred solution of 1-[2-(ethoxymethyl)-1H-imidazo[4,5-c]quinolin-1-yl]-2-methylpropan-2-ol (2.15 g, 7.2 mmol) and phenyl vinyl sulfone (2.42 g, 14.4 mmol) in anhydrous tetrahydrofuran (29 mL). The reaction mixture was stirred at ambient temperature for about 1 hour, and then it was quenched with water (50 mL) and extracted with ethyl acetate (3×50 mL). The combined extracts were washed with brine (50 mL), dried over anhydrous sodium sulfate, filtered, and concentrated under reduced pressure to provide crude product as an oil. This material was purified by column chromatography (silica gel eluting with 95/5 dichloromethane/methanol) to provide 0.95 g of 2-ethoxymethyl-1-{2-[2-(phenylsulfonyl)ethoxy]-2-methylpropyl}-1H-imidazo[4,5-c]quinoline as a colorless foam.

Part E

Using the method of Example 4 Part B, the material from Part D was oxidized to provide 2-ethoxymethyl-1-{2-[2-(phenylsulfonyl)ethoxy]-2-methylpropyl}-1H-imidazo[4,5-c]quinoline 5-oxide as an orange foam.

Part F

Using the method of Example 4 Part C, the material from Part E was aminated. The crude product was purified by column chromatography (silica gel eluting with 95/5 dichloromethane/methanol) followed by recrystallization from ethyl acetate. White, crystalline plates were isolated by filtration, washed with ethyl acetate, and dried under vacuum at 65° C. for 4 hours to provide 0.55 g of 2-ethoxymethyl-1-{2-[2-(phenylsulfonyl)ethoxy]-2-methylpropyl}-1H-imidazo[4,5-c]quinolin-4-amine, mp 187-189° C. $^1$H NMR (300 MHz, DMSO-$d_6$) δ 8.20 (d, J=8.1 Hz, 1H), 7.77-7.75 (m, 2H), 7.69-7.53 (m, 4H), 7.40 (t, J=8.1 Hz, 1H), 7.19 (t, J=8.1 Hz, 1H), 6.57 (bs, 2H), 4.77 (bs, 2H), 4.65 (bs, 2H), 3.53-3.47 (m, 4H), 3.34 (t, J=5.6 Hz, 2H), 1.12 (t, J=6.9 Hz, 3H), 1.07 (bs, 6H); MS (APCI) m/z 483 (M+H)+; Anal. Cacld for $C_{25}H_{30}N_4O_4S$: C, 62.22; H, 6.27: N, 11.61. Found: C, 62.18; H, 6.55; N, 11.50.

Example 9

2-Ethoxymethyl-1-{2-[2-(methylsulfonyl)ethoxy]-2-methylpropyl}-1H-imidazo[4,5-c]quinolin-4-amine

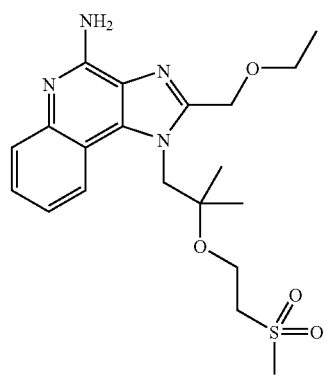

Part A

Using the general method of Example 8 Part D, 1-[2-(ethoxymethyl)-1H-imidazo[4,5-c]quinolin-1-yl]-2-methylpropan-2-ol (2.0 g, 6.7 mmol) was reacted with methyl vinyl sulfone (1.42 g, 13.4 mmol). The reaction mixture was quenched with water (50 mL) and extracted with ethyl acetate (3×50 mL). The combined extracts were washed with brine (50 mL), dried over anhydrous sodium sulfate, filtered, and concentrated under reduced pressure to provide crude product as an oil. This material was purified by column chromatography (silica gel eluting with 95/5 dichloromethane/methanol) to provide 1.75 g of 1-{2-[2-(methylsulfonyl)ethoxy]-2-methylpropyl}-2-ethoxymethyl-1H-imidazo[4,5-c]quinoline as a colorless foam.

Part B

Using the method of Example 4 Part B, the material from Part A was oxidized to provide 1-{2-[2-(methylsulfonyl)ethoxy]-2-methylpropyl}-2-ethoxymethyl-1H-imidazo[4,5-c]quinoline 5-oxide as an orange foam.

Part C

Using the method of Example 4 Part C, the material from Part B was aminated. The crude product was purified by column chromatography (silica gel eluting with 95/5 dichloromethane/methanol) followed by recrystallization from ethyl acetate. Colorless plates were isolated by filtration, washed with ethyl acetate, and dried under vacuum at 65° C. for 4 hours to provide 1.1 g of 2-ethoxymethyl-1-{2-[2-(methylsulfonyl)ethoxy]-2-methylpropyl}-1H-imidazo[4,5-c]quinolin-4-amine, mp 183-185° C. $^1$H NMR (300 MHz, DMSO-$d_6$) δ 8.30 (d, J=8.1 Hz, 1H), 7.60 (d, J=8.1 Hz, 1H), 7.42 (t, J=8.1 Hz, 1H), 7.23 (t, J=8.1 Hz, 1H), 6.57 (bs, 2H), 4.80 (bs, 4H), 3.63 (t, J=5.6 Hz, 2H), 3.53 (q, J=6.9 Hz, 2H), 3.10 (t, J=5.6 Hz, 2H), 2.65 (s, 3H) 1.23 (bs, 6H), 1.13 (t, J=6.9 Hz, 3H);

MS (APCI) m/z 421 (M+H)$^+$;

Anal. Cacld for $C_{20}H_{28}N_4O_4S$: C, 57.12; H, 6.71: N, 13.32. Found: C, 57.14; H, 6.56; N, 13.19.

Example 10

1-{2-[2-(Methylsulfonyl)ethoxy]ethyl}-2-methyl-6,7,8,9-tetrahydro-1H-imidazo[4,5-c]quinolin-4-amine

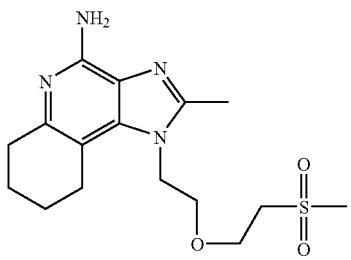

Solid platinum oxide (0.5) was added to a solution of 1-{2-[2-(methylsulfonyl)ethoxy]ethyl}-2-methyl-1H-imidazo[4,5-c]quinolin-4-amine (0.9 g, 2.6 mmol) in trifluoroacetic acid (7 mL) in a Parr vessel. The vessel was placed on a shaker and then pressurized with hydrogen to 50 psi (3.4× 10$^5$ Pa). Hydrogen was added periodically to maintain the pressure. After 55 hours the reaction mixture was purged with nitrogen and then filtered through a layer of CELITE filter agent. The filter cake was washed with dichloromethane (~200 mL). The filtrate was concentrated under reduced pressure to provide an oil. The oil was dissolved in water (50 mL). The pH of the solution was adjusted to pH 12 by the addition of aqueous 50% sodium hydroxide and then the solution was extracted with dichloromethane (2×100 mL). The combined extracts were washed with brine (100 mL), dried over anhydrous sodium sulfate, filtered, and concentrated under reduced pressure to provide crude product as a white foam. This material was recrystallized from ethyl acetate. The resulting off white plates were isolated by filtration, washed with ethyl acetate and dried under vacuum at 65° C. for 4 hours to provide 0.7 g of 1-{2-[2-(methylsulfonyl)ethoxy]ethyl}-2-methyl-6,7,8,9-tetrahydro-1H-imidazo[4,5-c]quinolin-4-amine, mp 173-175° C. $^1$H NMR (300 MHz, DMSO-$d_6$) δ 5.65 (bs, 2H), 4.40 (t, J=5.0 Hz, 2H), 3.73 (t, J=5.6 Hz, 2H), 3.32 (t, J=5.6 Hz, 2H), 2.91 (m, 2H), 2.78 (s, 3H) 2.65 (m, 2H), 2.47 (s, 3H), 1.75 (m, 4H); MS (APCI) m/z 353 (M+

Anal. Cacld for $C_{16}H_{24}N_4O_3S$: C, 54.52; H, 6.86: N, 15.90. Found: C, 54.41; H, 6.77; N, 15.70.

Example 11

1-{2-[2-(Methylsulfonyl)ethoxy]ethyl}-2-propyl-6,7,8,9-tetrahydro-1H-imidazo[4,5-c]quinolin-4-amine

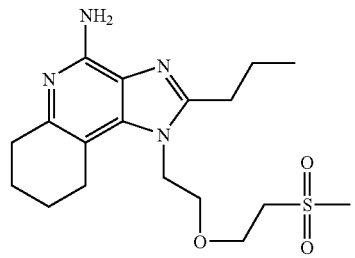

Using the method of Example 10, 1-{2-[2-(methylsulfonyl)ethoxy]ethyl}-2-propyl-1H-imidazo[4,5-c]quinolin-4-amine (1.1 g) was reduced and purified to provide 0.75 g of 1-{2-[2-(methylsulfonyl)ethoxy]ethyl}-2-propyl-6,7,8,9-tetrahydro-1H-imidazo[4,5-c]quinolin-4-amine as a white powder, mp 153-155° C. $^1$H NMR (300 MHz, DMSO-$d_6$) δ 5.63 (bs, 2H), 4.41 (t, J=5.6 Hz, 2H), 3.74-3.71 (m, 4H), 3.31 (m, 2H), 2.92 (m, 2H), 2.80-2.76 (m, 5H), 2.65 (m, 2H) 1.81-1.75 (m, 6H), 0.99 (t, J=7.5 Hz, 3H); MS (APCI) m/z 381 (M+H)$^+$;

Anal. Cacld for $C_{18}H_{28}N_4O_3S$: C, 56.82; H, 7.42: N, 14.72. Found: C, 56.60; H, 7.33; N, 14.67.

Example 12

2-Ethyl-1-{2-[2-(methylsulfonyl)ethoxy]ethyl}-6,7,8,9-tetrahydro-1H-imidazo[4,5-c]quinolin-4-amine

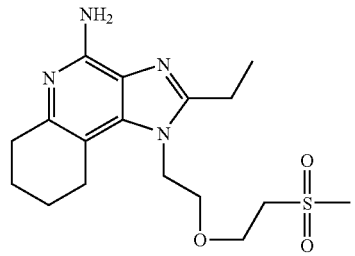

2-Ethyl-1-{2-[2-(methylsulfonyl)ethoxy]ethyl}-1H-imidazo[4,5-c]quinolin-4-amine (1.25 g) was reduced and purified using the method of Example 10, except that the crude material was purified by column chromatography (silica gel eluting with 95/5 dichloromethane/methanol) prior to the recrystallization from ethyl acetate, to provide 0.5 g of 2-ethyl-1-{2-[2-(methylsulfonyl)ethoxy]ethyl}-6,7,8,9-tetrahydro-1H-imidazo[4,5-c]quinolin-4-amine as a white granular solid, mp 146-148° C. $^1$H NMR (300 MHz, DMSO-$d_6$) δ 5.62 (bs, 2H), 4.40 (t, J=5.6 Hz, 2H), 3.74-3.70 (m, 4H), 3.31 (m, 2H), 2.92 (m, 2H), 2.83 (q, J=7.5 Hz, 2H), 2.78 (s, 3H) 2.65 (m, 2H), 1.75 (m, 4H), 1.30 (t, J=7.5 Hz, 3H);

MS (APCI) m/z 367 (M+H)$^+$; Anal. Cacld for $C_{17}H_{26}N_4O_3S$: C, 55.72; H, 7.15: N, 15.29. Found: C, 55.77; H, 7.14; N, 14.95.

Example 13

1-{2-[3-(Phenylsulfonyl)propoxy]ethyl}-2-propyl-1H-imidazo[4,5-c]quinolin-4-amine

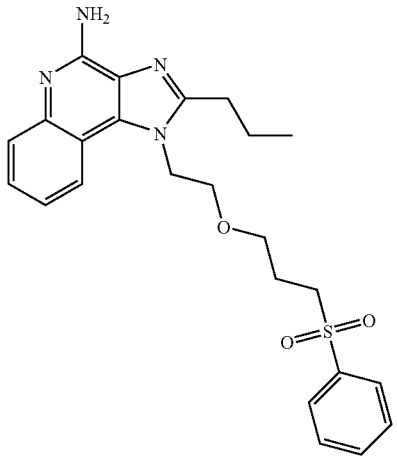

Part A

Sodium hydroxide (800 mL of 2M in water) was added to a solution of ethanol amine (100 6, 1.64 mole) in tetrahydrofuran (850 mL). The reaction mixture was placed in a 25° C. water bath and stirred rapidly. A solution of tert-butyl dicarbonate (358 g, 1.64 mole) in tetrahydrofuran (800 mL) was added dropwise over a period of 1 hour. The reaction mixture was stirred for a total of 4 hours at which time analysis by TLC indicated that all of the starting material had been consumed. The tetrahydrofuran was removed under reduced pressure to provide an aqueous slurry. The slurry was cooled in an ice bath. The pH was adjusted to pH 2 by the addition of sulfuric acid (1 L of 1M in water). The resulting solution was extracted with ethyl acetate (4×500 mL). The combined extracts were washed sequentially with water (3×500 mL) and brine (2×500 mL), dried over anhydrous sodium sulfate, filtered, and concentrated under reduced pressure to give a first lot of crude product. Analysis of the aqueous and brine washes indicated that they contained product so they were extracted with ethyl acetate. The combined extracts were dried over anhydrous sodium sulfate, filtered, and concentrated under reduced pressure to provide a second lot of crude product. The two lots were combined to provide 263.8 g of tert-butyl (2-hydroxyethyl)carbamate as a colorless oil.

Part B

Sodium hydroxide (1.50 L of 50% aqueous) was added to a solution of 243.8 g (1.514 mole) of material from Part A in dichloromethane (3 L). Benzyltrimethylammonium chloride (28.1 g, 0.151 mole) was added. The reaction mixture was placed in a water bath (25° C.) and stirred vigorously. Allyl bromide (144 mL, 1.66 mole) was added in a single portion. The reaction mixture was stirred for a total of 19 hours at which time analysis by TLC indicated that all of the starting material had been consumed. The reaction mixture was divided into two portions and each portion was worked up in the following manner. The reaction mixture was diluted with ice water (1 L). The phases were separated. The aqueous phase was extracted with dichloromethane (3×1 L). The combined organics were washed sequentially with water (3×1 L) and brine (2×1 L), dried over anhydrous sodium sulfate, filtered, and concentrated under reduced pressure. The two portions were combined to provide 269.6 g of tert-butyl [2-(allyloxy)ethyl]carbamate as a colorless oil.

Part C

Under a nitrogen atmosphere 9-borabicyclo[3.3.1]nonane (1.192 L of 0.5M in tetrahydrofuran, 0.596 mole) was added dropwise over a period of 1 hour at 9° C. to 100.0 g (0.497 mole) of the material from Part B. After 4 hours the reaction mixture was cooled to ~5° C. followed by the sequential addition of water (100 mL) and sodium hydroxide (250 mL of 3N). Hydrogen peroxide (142 mL of 30%, 1.39 mol) was added over a period of 1 hour. After a total reaction time of 15 hours analysis by TLC indicated that the reaction was complete. Sodium metabisulfite was added to neutralize the excess peroxide followed by the addition of water (500 mL). The reaction mixture was washed with hexanes (1 L) and then concentrated under reduced pressure to provide an oil. The oil was dried under vacuum at ambient temperature over the weekend to provide crude tert-butyl [2-(3-hydroxypropoxy) ethyl]carbamate as a white semi-solid.

Part D

The crude product from Part C was combined with hydrochloric acid (1.242 L of 4M in dioxane) and then stirred under a nitrogen atmosphere for ~42 hours. The reaction mixture was concentrated under reduced pressure, triturated with dichloromethane/methanol and then concentrated under reduced pressure to provide an oil. The oil was triturated with diethyl ether four times and then dried under vacuum to provide crude 3-(2-aminoethoxy)propan-1-ol hydrochloride.

Part E

Triethylamine (188 mL, 1.37 mole) was added to a slurry of the material from Part D in dichloromethane (1.3 L). Under a nitrogen atmosphere 4-chloro-3-nitroquinoline (81.6 g, 391 mmol) was added to the reaction mixture. After 1 hour analysis by high performance liquid chromatography (HPLC) indicated that the starting quinoline had been consumed. The reaction mixture was washed sequentially with aqueous sodium bicarbonate, water, and brine, dried over sodium sulfate, filtered, and then concentrated under reduced pressure to provide a sticky yellow solid. This material was purified by column chromatography (1.5 Kg of silica gel eluting with 98/2 dichloromethane/methanol) to provide 98.1 g of 3-{2-[(3-nitroquinolinyl)amino]ethoxy}propan-1-ol as a yellow solid.

Part F

Under a nitrogen atmosphere thionyl chloride (3.7 mL, 51 mmol) was added to a slurry of 10 g (34 mmol) of the material from Part E in dichloromethane (100 mL). The reaction mixture was heated at reflux for 2.5 hours and then stirred at ambient temperature overnight. Analysis by HPLC indicated that all of the starting material had been consumed. The reaction mixture was concentrated under reduced pressure and the residue was dissolved in water (200 mL). The solution was basified (pH~10-11) with solid potassium carbonate and then chilled in an ice bath for 40 minutes. The resulting precipitate was isolated by filtration, rinsed with ice cold water, and then dried under vacuum at 70° C. for several hours. This material was dissolved in dichloromethane/methanol and then concentrated under reduced pressure. This procedure was repeated twice with dichloromethane/methanol and then with diethyl ether to provide 11.2 g of N-[2-(3-chloropropoxy)ethyl]-3-nitroquinolin-4-amine as a dirty yellow solid.

Part G

A slurry of the material from Part F in toluene (75 mL) was added to a Parr vessel containing 5% platinum on carbon (0.50 g) and toluene (25 mL). The vessel was placed on a shaker and then pressurized with hydrogen to 50 psi ($3.4 \times 10^5$ Pa). After 16 hours analysis by TLC indicated that the reaction was not complete. Additional catalyst (0.50 g) was added and the reaction was pressurized with hydrogen to 50 psi ($3.4 \times 10^5$ Pa). After 4 hours analysis by TLC indicated that all of the starting material had been consumed. The reaction mixture was purged with nitrogen and then filtered. The filter cake was rinsed with a mixture of toluene and ethanol. The filtrate was concentrated under reduced pressure to provide 9.24 g of $N^4$-[2-(3-chloropropoxy)ethyl]quinoline-3,4-diamine as a gummy solid.

Part H

Trimethyl orthobutyrate (7.9 mL, 50 mmol) and pyridine hydrochloride (0.076 g, 0.66 mmol) were added to a solution of the material from Part G in toluene (100 mL). The reaction was refluxed under a nitrogen atmosphere for 19 hours at which time analysis by HPLC indicated that all of the starting material had been consumed. The reaction mixture was concentrated under reduced pressure to provide 10.5 g of crude 1-[2-(3-chloropropoxy)ethyl]-2-propyl-1H-imidazo[4,5-c]quinoline as a black oil.

Part I

3-Chloroperoxybenzoic acid (12.74 g of 75%, 55.4 mmol) was added in a single portion to a solution of the material from Part H in dichloromethane (100 mL). The reaction mixture was stirred at ambient temperature for 30 minutes at which time analysis by HPLC indicated that all of the starting material had been consumed. Ammonium hydroxide (50 mL of 27%) was added followed by the slow addition of tosyl chloride (6.64 g, 34.8 mmol). After the addition was complete the reaction mixture was stirred at ambient temperature for 30 minutes at which time analysis by HPLC indicated that all of the starting material had been consumed. The reaction mixture was diluted with dichloromethane, washed sequentially with aqueous potassium carbonate, water, and brine, dried over anhydrous sodium sulfate, filtered, and concentrated under reduced pressure to prove 8.5 g of crude product as a gray solid. This material was purified by column chromatography (93 g of silica gel eluting with ethyl acetate) to provide 4.5 g of product. This material was recrystallized from acetonitrile (20 mL) to provide 1.8 g of 1-[2-(3-chloropropoxy) ethyl]-2-propyl-1H-imidazo[4,5-c]quinolin-4-amine as a white crystalline powder, mp 131.0-132.0° C. $^1$H NMR (300 MHz, DMSO) δ 8.05 (d, J=8.2 Hz, 1H), 7.61 (d, J=8.3, 1H), 7.41 (t, J=8.1 Hz, 1H), 7.21 (t, J=8.1 Hz, 1H), 6.45 (s, 2H), 4.72 (t, J=5.1 Hz, 2H), 3.84 (t, J=5.1 Hz, 2H), 3.42 (t, J=6.6 Hz, 2H), 2.91 (t, J=7.5 Hz, 2H), 1.78-1.89 (m, 4H), 1.04 (t, J=7.4 Hz, 3H); MS (APCI) m/z 347 (M+H)$^+$; Anal. calcd for $C_{18}H_{23}ClN_4O$: C, 62.33; H, 6.68; N, 16.15. Found: C, 62.39; H, 6.58; N, 16.23.

Part J

Under a nitrogen atmosphere thiophenol (0.9 mL, 8.6 mmol) was added to a suspension of sodium hydride (0.19 g, 7.9 mmol) in DMF (25 mL). After hydrogen evolution had ceased, 1-[2-(3-chloropropoxy)ethyl]-2-propyl-1H-imidazo [4,5-c]quinolin-4-amine (2.50 g, 7.2 mmol, prepared by the methods of Parts A-I) was added. The reaction mixture was stirred at ambient temperature for 1.5 hours at which time analysis by HPLC indicated that all of the starting material had been consumed. The reaction mixture was poured into water (250 mL) with rapid stirring. Sodium carbonated (~0.5 g) was added to neutralize any excess thiolate and the pH was adjusted to ~14 with 50% sodium hydroxide. The resulting tan precipitate was isolated by filtration and then recrystallized from acetonitrile to provide 1.95 g of 1-{2-[3-(phenylthio)propoxy]ethyl}-2-propyl-1H-imidazo[4,5-c]quinolin-4-amine as a tan crystalline solid.

Part K

3-Chloroperoxybenzoic acid (2.35 g of 75%, 10.2 mmol) was added to a solution of the material from Part J (1.9 g, 4.6 mmol) in dichloromethane (15 mL). After 15 minutes analysis by HPLC indicated that all of the starting material had been consumed. The reaction mixture was diluted with dichloromethane (50 mL), washed sequentially with aqueous saturated potassium carbonate, water (3×50 mL), and brine (3×50 mL), dried over anhydrous sodium sulfate, filtered, and concentrated under reduced pressure to provide 1.44 g of a brown gummy solid. This material was triturated with ether to provide a solid which was combined with 0.82 g of material from another run and purified by column chromatography (50 g of silica gel eluting with 98/2 dichloromethane/methanol) to provide 1.1 g of 1-{2-[3-(phenylsulfonyl)propoxy]ethyl}-2-propyl-1H-imidazo[4,5-c]quinolin-4-amine as a white powder, mp 160.0-161.0° C. $^1$H NMR (300 MHz, DMSO) δ 8.03 (d, J=7.8 Hz, 1H), 7.69-7.76 (m, 3H), 7.59-7.64 (m, 3H), 7.41 (t, J=8.1 Hz, 1H), 7.21 (t, J=7.0 Hz, 1H), 6.47 (s, 2H), 4.68 (t, J=5.0 Hz, 2H), 3.76 (t, J=5.0 Hz, 2H), 3.32 (t, J=6.0 Hz, 2H), 3.08-3.13 (m, 2H), 2.86 (t, J=7.5 Hz, 2H), 1.81 (apparent hextet, J=7.6, 7.4, 7.3 Hz, 2H), 1.61-1.69 (m, 2H), 1.00 (t, J=7.4 Hz, 3H); MS (APCI) m/z 453 (M+H)$^+$; Anal. calcd for $C_{24}H_{28}N_4O_3S$: C, 63.69; H, 6.24; N, 12.38. Found: C, 63.51; H, 6.32; N, 12.28.

Example 14

1-(2-{3-[(1-Methylethyl)sulfonyl]propoxy}ethyl)-2-propyl-1H-imidazo[4,5-c]quinolin-4-amine

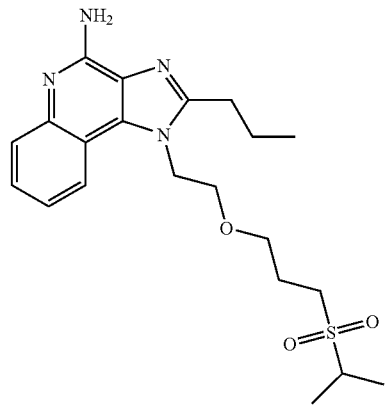

Part A

Nitrogen was bubbled through a solution of 1-[2-(3-chloropropoxy)ethyl]-2-propyl-1H-imidazo[4,5-c]quinolin-4-amine (2.50 g, 7.21 mmol) in DMF (25 mL) for 5 minutes.

Sodium 2-propanethiolate (0.85 g 8.65 mmol) was added and the reaction mixture was stirred under a nitrogen atmosphere at ambient temperature. After 16 hours analysis by HPLC indicated that 50% of the starting material had been consumed. Additional sodium 2-propanethiolate (0.6 g) was added followed by a second addition (0.25 g) 2.5 hours later. After a total of 21 hours the reaction mixture was poured into water (250 mL) with rapid stirring. The resulting tan precipitate was isolated by filtration to provide 2.34 g of 1-(2-{3-[(1-methylethyl)thio]propoxy}ethyl)-2-propyl-1H-imidazo[4,5-c]quinolin-4-amine.

Part B

3-Chloroperoxybenzoic acid (2.79 g of 75%, 12.1 mmol) was added to a solution of the material from Part A (2.34 g, 6.06 mmol) in dichloromethane (25 mL). After 15 minutes analysis by HPLC indicated that all of the starting material had been consumed. The reaction mixture was diluted with dichloromethane (50 mL), washed sequentially with aqueous saturated potassium carbonate, water (3×50 mL), and brine (2×50 mL), dried over anhydrous sodium sulfate, filtered, and concentrated under reduced pressure to provide crude product as a brown oil. This material was purified by column chromatography (300 g of silica gel eluting with 98/2 dichloromethane/methanol) followed by recrystallization from acetonitrile to provide 1.53 g of 1-(2-{3-[(1-methylethyl)sulfonyl]propoxy}ethyl)-2-propyl-1H-imidazo[4,5-c]quinolin-4-amine as a white crystalline solid, mp 176.0-177.0° C.
$^1$H NMR (300 MHz, DMSO) δ 8.07 (d, J=7.7 Hz, 1H), 7.61 (d, J=8.3, 1H), 7.41 (t, J=8.0 Hz, 1H), 7.22 (t, J=8.1 Hz, 1H), 6.44 (s, 2H), 4.73 (t, J=5.0 Hz, 2H), 3.84 (t, J=5.0 Hz, 2H), 3.40 (t, J=6.1 Hz, 2H), 3.10 (p, J=6.8, 6.8 Hz, 1H), 2.81-2.94 (m, 4H), 1.76-1.89 (m, 4H), 1.13 (d, J=6.8, 6H), 1.03 (t, J=7.3 Hz, 3H); MS (APCI) m/z 419 (M+H)$^+$; Anal. calcd for $C_{21}H_{30}N_4O_3S$: C, 60.26; H, 7.22; N, 13.39. Found: C, 60.13; H, 7.57; N, 13.39

Example 15

1-(2-{3-[(2-Methylphenyl)sulfonyl]propoxy}ethyl)-2-propyl-1H-imidazo[4,5-c]quinolin-4-amine

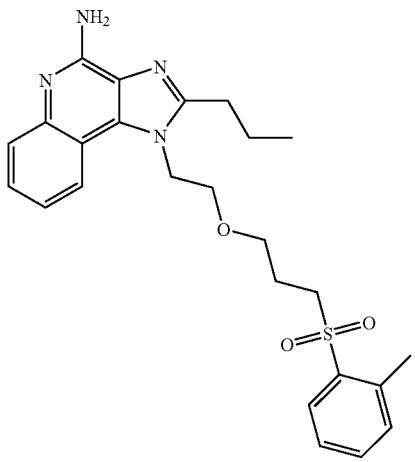

Part A

Under a nitrogen atmosphere sodium hydride (0.19 g, 7.9 mmol) was added to a solution of ortho-thiocresol in DMF (25 mL). After hydrogen evolution had ceased, 1-[2-(3-chloropropoxy)ethyl]-2-propyl-1H-imidazo[4,5-c]quinolin-4-amine (2.50 g, 7.2 mmol) was added. After 2 hours analysis by HPLC indicated that starting material remained. Ortho-thiocresol (0.5 mL) and sodium hydride (0.10 g) were added. The reaction was stirred for 1.7 days at which time analysis by HPLC indicated that all of the starting material had been consumed. The reaction mixture was poured into water (250 mL) with rapid stirring and the resulting mixture was extracted with dichloromethane (50 mL). The organic layer was washed sequentially with aqueous saturated potassium carbonate and brine, dried over anhydrous sodium sulfate, filtered, and concentrated under reduced pressure to provide 3.68 g of crude 1-(2-{3-[(2-methylphenyl)thio]propoxy}ethyl)-2-propyl-1H-imidazo[4,5-c]quinolin-4-amine as a brown gummy solid.

Part B

3-Chloroperoxybenzoic acid (3.32 g of 75%, 14.4 mmol) was added to a solution of the material from Part A in dichloromethane (25 mL). Additional 3-chloroperoxybenzoic acid (0.80 g and 0.20 g) was added at 1 hr and 2 hr respectively when analysis by HPLC indicated that starting material remained. Fifteen (15) minutes after the second addition the reaction mixture was diluted with 1N potassium hydroxide (50 mL). The organic layer was separated then washed sequentially with water (2×75 mL) and brine (2×50 mL), dried over anhydrous sodium sulfate, filtered, and concentrated under reduced pressure to provide 3.44 g of a brown oil. This material was purified by column chromatography (200 g of silica gel eluting with 98/2 dichloromethane/methanol) to provide 1.20 g of product. This material was recrystallized from acetonitrile (15 mL) and then triturated with dichloromethane/methanol to provide 0.58 g of 1-(2-{3-[(2-methylphenyl)sulfonyl]propoxy}ethyl)-2-propyl-1H-imidazo[4,5-c]quinolin-4-amine as a white powder, mp 159.0-160.0° C.
$^1$H NMR (300 MHz, CDCl3) δ 7.89 (t, J=7.8 Hz, 2H), 7.80 (d, J=7.80 Hz, 1H), 7.44-7.48 (m, 2H), 7.23-7.33 (m, 3H), 5.38 (s, 2H), 4.64 (t, J=5.5 Hz, 2H), 3.83 (t, J=5.5 Hz, 2H), 3.41 (t, J=5.9 Hz, 2H), 3.04 (t, J=7.6 Hz, 2H), 2.87 (t, J=7.7 Hz, 2H), 2.55 (s, 3H), 1.84-1.96 (m, 4H), 1.07 (t, J=7.4 Hz, 3H); MS (APCI) m/z 467 (M+H)$^+$; Anal. calcd for $C_{25}H_{30}N_4O_3S.0.1H_2O$: C, 64.11; H, 6.50; N, 11.96. Found: C, 63.93; H, 6.51; N, 11.91.

Example 16

2-Propyl-1-(2-{3-[(pyridin-2-yl)sulfonyl]propoxy}ethyl)-1H-imidazo[4,5-c]quinolin-4-amine

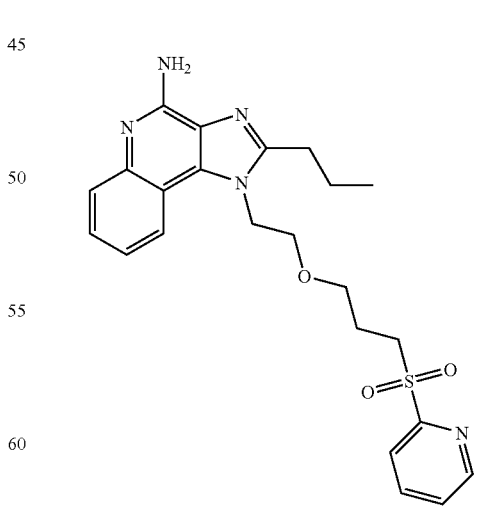

Part A

Under a nitrogen atmosphere 2-mercaptopyridine (1.23 g, 11.1 mmol) was added to a suspension of sodium hydride (0.41 g of 60%, 10 mmol) in DMF (30 mL). After hydrogen evolution had ceased, 1-[2-(3-chloropropoxy)ethyl]-2-propyl-1H-imidazo[4,5-c]quinolin-4-amine (3.20 g, 9.23 mmol) was added. After 2 hours analysis by HPLC indicated that starting material remained. 2-Mercaptopyridine (0.30 g) and sodium hydride (0.10 g) were added. After 3.5 hours the reaction mixture was poured into water with rapid stirring. The resulting brown solid was isolated by filtration and then triturated with diethyl ether to provide 3.71 g of 2-propyl-1-(2-{3-[(pyridin-2-yl)thio]propoxy}ethyl)-1H-imidazo[4,5-c]quinolin-4-amine as a solid.

Part B

3-Chloroperoxybenzoic acid (4.10 g of 75%, 17.6 mmol) was added to a solution of the material from Part A in dichloromethane (30 mL). After 15 minutes analysis by HPLC indicated that all of the starting material had been consumed. The reaction mixture was diluted with 1N potassium hydroxide (100 mL) and dichloromethane (50 mL) and stirred for 10 minutes. The organic layer was separated then washed sequentially with 1N potassium hydroxide (2×50 mL), water (1×50 mL) and brine (2×50 mL), dried over magnesium sulfate, filtered, and concentrated under reduced pressure to provide 3.61 g of a brown solid. This material was triturated with ethyl acetate containing a small amount of dichloromethane to provide 2.1 g of a brown solid. This material was purified by column chromatography (silica gel eluting sequentially with ethyl acetate, 95/5 ethyl acetate/methanol, and 9/1 ethyl acetate/methanol) to provide 1.2 g of 2-propyl-1-(2-{3-[(pyridine-2-yl)sulfonyl]propoxy}ethyl)-1H-imidazo[4,5-c]quinolin-4-amine as a white powder, mp 150.0-151.0° C. $^1$H NMR (300 MHz, DMSO) δ 8.72 (d, J=4.7 Hz, 1H), 8.13 (t, J=7.8 Hz, 1H), 7.97-8.01 (m, 2H), 7.71-7.73 (m, 1H), 7.58 (d, J=7.3 Hz, 1H), 7.37 (t, J=8.2 Hz, 1H), 7.17 (t, J=7.0 Hz, 1H), 6.38 (s, 2H), 4.67 (t, J=5.2 Hz, 2H), 3.76 (t, J=5.2 Hz, 2H), 3.28-3.38 (m, 4H), 2.86 (t, J=7.6 Hz, 2H), 1.82 (apparent hextet, J=7.6, 7.4, 7.3 Hz, 2H), 1.69-1.71 (m, 2H), 0.99 (t, J=7.4 Hz, 3H); MS (APCI) m/z 454 (M+H)$^+$; Anal. calcd for $C_{23}H_{27}N_5O_3S$: C, 60.91; H, 6.00; N, 15.44. Found: C, 60.59; H, 5.91; N, 15.32.

Example 17

1-{2-[3-(Methylthio)propoxy]ethyl}-2-propyl-1H-imidazo[4,5-c]quinolin-4-amine

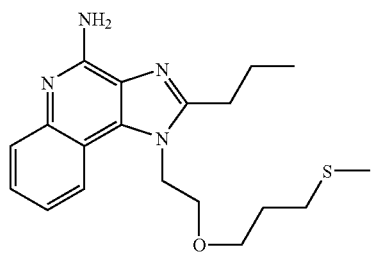

A suspension of sodium thiomethoxide (0.94 g of 95%, 13 mmol) and 1-[2-(3-chloropropoxy)ethyl]-2-propyl-1H-imidazo[4,5-c]quinolin-4-amine (3.7 g, 11 mmol) in DMF (53 mL) was heated at 80° C. for 2 hours. The reaction mixture was poured in water (400 mL) with rapid stirring. The mixture was stirred at ambient temperature for 1 hour and then chilled in an ice/water bath for 1 hour. The resulting precipitate was isolated by filtration, washed with cold water, and air dried to provide 3.5 g of product. A portion (0.85 g) was recrystallized from ethyl acetate to provide 1-{2-[3-(methylthio)propoxy]ethyl}-2-propyl-1H-imidazo[4,5-c]quinolin-4-amine as a white powder, mp 99-101° C. $^1$H NMR (300 MHz, DMSO-d$_6$) δ 8.06 (d, J=8.1 Hz, 1H), 7.60 (d, J=8.1 Hz, 1H), 7.40 (t, J=8.1 Hz, 1H), 7.21 (t, J=8.1 Hz, 1H), 6.42 (bs, 2H), 4.71 (t, J=5.0 Hz, 2H), 3.82 (t, J=5.0 Hz, 2H), 3.37 (t, J=6.2 Hz, 2H), 2.92 (t, J=7.5 Hz, 2H), 2.30 (t, J=7.5 Hz, 2H), 1.89 (s, 3H) 1.86 (sextet, J=7.5 Hz, 2H) 1.60 (pentet, J=7.5 Hz, 2H) 1.03 (t, J=7.5 Hz, 3H); MS (APCI) m/z 359 (M+H)$^+$; Anal. Cacld for $C_{19}H_{26}N_4OS.½H_2O$: C, 62.10; H, 7.40: N, 15.24. Found: C, 61.93; H, 7.16; N, 15.14.

Example 18

1-{2-[3-(ethylsulfinyl)propoxy]ethyl}-2-propyl-1H-imidazo[4,5-c]quinolin-4-amine

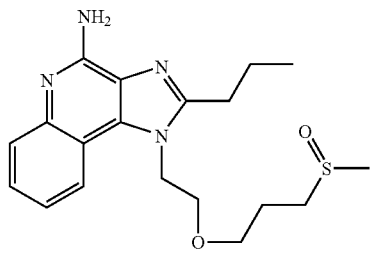

3-Chloroperoxybenzoic acid (0.62 g of ~77%, 2.8 mmol) was added in portions over a period of 5 minutes to a solution of 1-{2-[3-(methylthio)propoxy]ethyl}-2-propyl-1H-imidazo[4,5-c]quinolin-4-amine (1.0 g, 2.8 mmol) in chloroform (14 mL). After 20 minutes analysis by TLC showed that all of the starting material had been consumed. The reaction mixture was partitioned between dichloromethane (100 mL) and saturated aqueous sodium carbonate (50 mL). The organic layer was washed sequentially with saturated aqueous sodium carbonate (50 mL) and brine (50 mL), dried over anhydrous sodium sulfate, filtered, and concentrated under reduced pressure to provide a white foam. This material was purified by column chromatography (silica gel eluting with 95/5 dichloromethane/methanol) followed by recrystallization from ethyl acetate (60 mL) to provide 0.44 g of 1-{2-[3-(methylsulfinyl)propoxy]ethyl}-2-propyl-1H-imidazo[4,5-c]quinolin-4-amine as crystalline plates, mp 148-151° C. $^1$H NMR (300 MHz, DMSO-d$_6$) δ 8.07 (d, J=8.1 Hz, 1H), 7.60 (d, J=8.1 Hz, 1H), 7.40 (t, J=8.1 Hz, 1H), 7.22 (t, J=8.1 Hz, 1H), 6.43 (bs, 2H), 4.72 (t, J=5.0 Hz, 2H), 3.84 (t, J=5.0 Hz, 2H), 3.40 (t, J=6.2 Hz, 2H), 2.92 (t, J=7.6 Hz, 2H), 2.46 (m, 2H), 2.39 (s, 3H) 1.86 (sextet, J=7.6 Hz, 2H) 1.71 pentet, J=7.6 Hz, 2H) 1.04 (t, J=7.6 Hz, 3H); MS (APCI) m/z 375 (M+H)$^+$; Anal. Cacld for $C_{19}H_{26}N_4O_2S$: C, 60.94; H, 7.00: N, 14.96. Found: C, 60.73; H, 6.82; N, 14.85.

Example 19

1-{2-[3-(Methylsulfonyl)propoxy]ethyl}-2-propyl-1H-imidazo[4,5-c]quinolin-4-amine

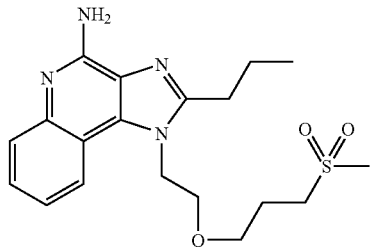

3-Chloroperoxybenzoic acid (2.2 g of ~77%, 7.6 mmol) was added in portions over a period of 9 minutes to a solution of 1-{2-[3-(methylthio)propoxy]ethyl}-2-propyl-1H-imidazo[4,5-c]quinolin-4-amine (1.37 g, 3.8 mmol) in chloro form (19 mL). After 15 minutes analysis by TLC showed that all of the starting material had been consumed. The reaction mixture was partitioned between dichloromethane (100 mL) and saturated aqueous sodium carbonate (50 mL). The organic layer was washed sequentially with saturated aqueous sodium carbonate (50 mL) and brine (50 mL), dried over anhydrous sodium sulfate, filtered, and concentrated under reduced pressure to provide a red oil. This material was purified by column chromatography (silica gel eluting with 95/5 dichloromethane/methanol) followed by recrystallization from ethyl acetate (60 mL) to provide 0.7 g of 1-{2-[3-(methylsulfonyl)propoxy]ethyl}-2-propyl-1H-imidazo[4,5-c]quinolin-4-amine as a beige powder, mp 149-151° C. $^1$H NMR (300 MHz, DMSO-d$_6$) δ 8.06 (d, J=8.1 Hz, 1H), 7.61 (d, J=8.1 Hz, 1H), 7.41 (t, J=8.1 Hz, 1H), 7.20 (t, J=8.1 Hz, 1H), 6.44 (bs, 2H), 4.73 (t, J=5.0 Hz, 2H), 3.84 (t, J=5.0 Hz, 2H), 3.41 (t, J=6.2 Hz, 2H), 2.96-2.89 (m, 4H), 2.86 (s, 3H) 1.90-1.77 (m, 4H) 1.04 (t, J=7.5 Hz, 3H); MS (APCI) m/z 391 (M+H)$^+$; Anal. Cacld for C$_{19}$H$_{26}$N$_4$O$_3$S: C, 58.44; H, 6.71: N, 14.35. Found: C, 58.40; H, 7.02; N, 14.31.

Example 20

1-{2-[3-(Decane-1-sulfonyl)propoxy]ethyl}-2-propyl-1H-imidazo[4,5-c]quinolin-4-amine

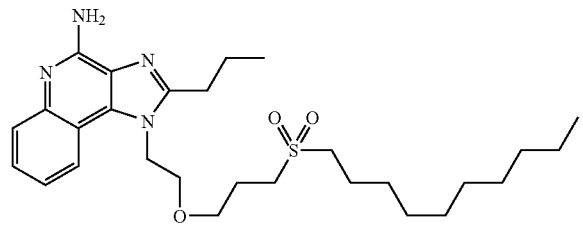

Part A

Sodium hydride (0.28 g of ~60%, 6.92 mmol) was added in portions to a solution of 1-decanethiol (1.2 g, 6.9 mmol) in DMF (29 mL). The reaction mixture was stirred at ambient temperature and then 1-[2-(3-chloropropoxy)ethyl]-2-propyl-1H-imidazo[4,5-c]quinolin-4-amine (2.0 g, 5.8 mmol) was added in portions. The reaction mixture was stirred at ambient temperature for 90 hours and then poured into water (200 mL) with rapid stirring. The resulting mixture was extracted with dichloromethane (2×100 mL). The combined extracts were concentrated under reduced pressure to provide crude product as a yellow oil. The oil was purified by column chromatography (silica gel eluting with 95/5 dichloromethane/methanol) to provide 1.55 g of 1-{2-[3-(decane-1-thio)propoxy]ethyl}-2-propyl-1H-imidazo[4,5-c]quinolin-4-amine as a clear oil.

Part B

The material from Part B was oxidized using the method of Example 19. The crude product was purified by column chromatography (silica gel eluting with 95/5 dichloromethane/methanol) to provide 1.3 g of a dark brown oil. The oil was dissolved in methanol (100 mL). The solution was heated gently then combined with activated charcoal (1 g of DARCO) and stirred for 10 minutes. The mixture was filtered through a layer of CELITE filter aid and the filter cake was washed with methanol. The filtrate was concentrated under reduced pressure to provide a colorless oil. The oil was triturated with diethyl ether to provide a solid. The solid was isolated by filtration, washed with diethyl ether, and dried under vacuum at ambient temperature to provide 0.7 g of 1-{2-[3-(decane-1-sulfonyl)propoxy]ethyl}-2-propyl-1H-imidazo[4,5-c]quinolin-4-amine as a white powder, mp 84-86° C. $^1$H NMR (300 MHz, DMSO-d$_6$) δ 8.06 (d, J=8.7 Hz, 1H), 7.61 (d, J=8.1 Hz, 1H), 7.41 (t, J=8.1 Hz, 1H), 7.23 (t, J=8.1 Hz, 1H), 6.47 (bs, 2H), 4.73 (t, J=5.0 Hz, 2H), 3.83 (t, J=5.0 Hz, 2H), 3.41 (t, J=6.2 Hz, 2H), 2.96-2.89 (m, 6H), 1.90-1.75 (m, 4H) 1.59-1.54 (m, 2H), 1.32-1.24 (m, 14H), 1.03 (t, J=7.5 Hz, 3H), 0.88-0.83 (m, 3H); MS (APCI) m/z 517 (M+H)$^+$; Anal. Cacld for C$_{28}$H$_{44}$N$_4$O$_3$S.½H$_2$O: C, 63.97; H, 8.63: N, 10.66. Found: C, 64.04; H, 8.64; N, 10.57.

Example 21

2-Methyl-1-{2-methyl-2-[2-(methylsulfonyl)ethoxy]propyl}-1H-imidazo[4,5-c]quinolin-4-amine

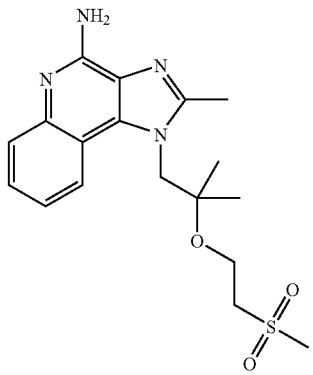

Part A

Sodium hydride (60% dispersion in mineral oil, 41 mg, 1.04 mmol) was added to a stirred solution of 1-(4-chloro-2-methyl-1H-imidazo[4,5-c]quinolin-1-yl)-2-methylpropan-2-ol (prepared as described in U.S. Pat. No. 5,266,575 Comparative Example C1, 3.00 g, 10.4 mmol) and methyl vinyl sulfone (2.20 g, 20.7 mmol) in tetrahydrofuran (41 mL). The reaction mixture was stirred at room temperature for 17 hours. Water (100 mL) was added and the mixture was extracted with ethyl acetate (3×50 mL). The organic layers were combined, washed with brine, dried over sodium sulfate, filtered, and concentrated under reduced pressure to afford an oil that was purified by flash chromatography (silica gel, eluted with ethyl acetate) to yield 1.8 g of 4-chloro-2-methyl-1-{2-methyl-2-[2-(methylsulfonyl)ethoxy]propyl}-1H-imidazo[4,5-c]quinoline as a white solid.

Part B

A suspension of 4-chloro-2-methyl-1-{2-methyl-2-[2-(methylsulfonyl)ethoxy]propyl}-1H-imidazo[4,5-c]quinoline (1.80 g, 4.55 mmol) in a solution of ammonia in methanol (7 M, 18 mL) in a high pressure vessel was heated at 150° C. for 14 hours. The vessel was allowed to cool to room temperature. A solid was isolated by filtration, washed with methanol, and purified by flash chromatography (silica gel, eluted with 10% methanol in dichloromethane) to provide a white solid. The solid was stirred in water (100 mL) for 1 hour, isolated by filtration, washed with water, and dried to yield 0.84 g of 2-methyl-1-{2-methyl-2-[2-(methylsulfonyl)ethoxy]propyl}-1H-imidazo[4,5-c]quinolin-4-amine as a white powder, mp 253-255° C.

$^1$H NMR (300 MHz, DMSO-d$_6$) δ 8.27 (d, J=8.1 Hz, 1H), 7.58 (d, J=8.1 Hz, 1H), 7.39 (t, J=8.1 Hz, 1H), 7.21 (t, J=8.1 Hz, 1H), 6.44 (bs, 2H), 4.66 (bs, 2H), 3.63 (t, J=5.6 Hz, 2H), 3.05 (t, J=5.6 Hz, 2H), 2.64 (s, 3H), 2.59 (s, 3H), 1.25 (bs,

6H); MS (APCI) m/z 377 (M+H)+; Anal. Cacld for $C_{18}H_{24}N_4O_3S$: C, 57.43; H, 6.43: N, 14.88. Found: C, 57.32; H, 6.47; N, 14.75.

Example 22

1-{2-Methyl-2-[2-(methylsulfonyl)ethoxy]propyl}-2-propyl-1H-imidazo[4,5-c]quinolin-4-amine

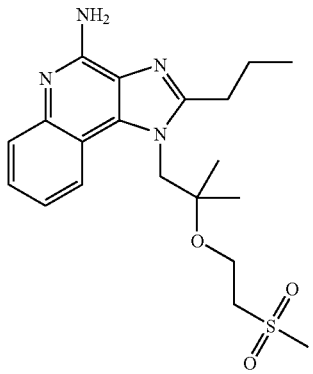

Part A

Trimethyl orthobutyrate (1.90 g, 12.7 mmol) and pyridine hydrochloride (0.13 g, 1.2 mmol) were added to a suspension of 1-[(3-aminoquinolin-4-yl)amino]-2-methylpropan-2-ol (prepared as described in Part A of Example 8, approximately 2.7 g, 11.5 mmol) in acetonitrile (60 mL). The reaction mixture was heated at reflux for 45 minutes with a Dean Stark trap, then was allowed to cool to room temperature and was concentrated under reduced pressure. The crude product was subjected to flash chromatography (silica gel, eluted with 5% methanol in dichloromethane) to yield a mixture of compounds that were combined and resubjected to the reaction conditions. The mixture was allowed to cool to room temperature and was concentrated under reduced pressure to afford 1-(2-propyl-1H-imidazo[4,5-c]quinolin-1-yl)-2-methylpropan-2-ol as a white solid that was used in the next step without purification.

Part B

Sodium metal (0.03 g, 1.3 mmol) was added to a solution of the material from Part A (1.7 g, 6.0 mmol) in tetrahydrofuran (24 mL). The reaction mixture was sonicated for 1 hour, then was heated at reflux for 2 hours. The reaction mixture was allowed to cool to room temperature and methyl vinyl sulfone (1.3 g, 12 mmol) was added dropwise. The reaction mixture was stirred at room temperature for 17 hours, then water (50 mL) was added. The mixture was extracted with ethyl acetate (3×50 mL). The organic layers were combined, washed with brine (50 mL), dried over sodium sulfate, filtered, and concentrated. The crude product was purified by flash chromatography (silica gel, eluted with 5% methanol in dichloromethane) to yield 1.3 g of 1-{2-methyl-2-[2-(methylsulfonyl)ethoxy]propyl}-2-propyl-1H-imidazo[4,5-c]quinoline as an off-white powder.

Part C

Using the method of Example 4 Part B, the material from Part B was oxidized to provide 1-{2-methyl-2-[2-(methylsulfonyl)ethoxy]propyl}-2-propyl-1H-imidazo[4,5-c]quinoline 5-oxide as a pale orange oil.

Part D

Using the method of Example 4 Part C, the material from Part C was aminated. The crude product was recrystallized from acetonitrile. The tan crystals were isolated by filtration, washed with acetonitrile, and dried under vacuum at 65° C. to afford 1.0 g of 1-{2-methyl-2-[2-(methylsulfonyl)ethoxy]propyl}-2-propyl-1H-imidazo[4,5-c]quinolin-4-amine as tan, crystalline plates, mp 203-206° C.

$^1$H NMR (300 MHz, DMSO-$d_6$) δ 8.28 (d, J=8.1 Hz, 1H), 7.58 (d, J=8.1 Hz, 1H), 7.39 (t, J=8.1 Hz, 1H), 7.21 (t, J=8.1 Hz, 1H), 6.39 (bs, 2H), 4.76-4.55 (bs, 2H), 3.61 (t, J=5.6 Hz, 2H), 2.98 (t, J=5.6 Hz, 2H), 2.56 (s, 3H), 1.82 (sextet, J=7.5 Hz, 2H), 1.23 (bs, 6H), 1.00 (t, J=7.5 Hz, 3H);

MS (APCI) m/z 405 (M+H)+;

Anal. Cacld for $C_{20}H_{28}N_4O_3S$: C, 59.38; H, 6.98: N, 13.85. Found: C, 59.38; H, 6.91; N, 13.82.

Example 23

2-(Ethoxymethyl)-1-({1-[2-(methylsulfonyl)ethoxy]cyclopentyl}methyl)-1H-imidazo[4,5-c]quinolin-4-amine

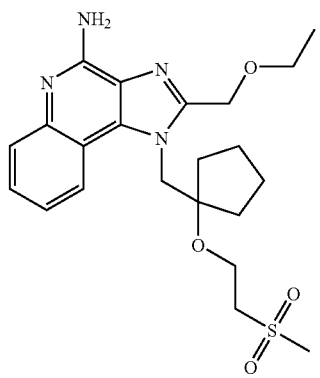

Part A

To a solution of cyclopentanone (40.0 mL, 452 mmol) in nitromethane (36 mL) and ethanol (14 mL) was added a solution of sodium ethoxide in ethanol (2.67 M, 8.5 mL, 23 mmol). The solution was stirred for 5 days at room temperature. Water (400 mL) was added and the mixture was extracted with ethyl acetate (2×350 mL). The combined organic extracts were washed with water (2×200) and brine (200 mL), dried over MgSO$_4$, filtered, and concentrated. The starting materials and solvent were removed from the product by distillation under reduced pressure to yield 8.3 g of 1-(nitromethyl)cyclopentanol as a yellow liquid.

Part B

A mixture of 1-(nitromethyl)cyclopentanol (8.3 g, 57.2 mmol) and 20% palladium hydroxide on carbon (0.6 g) in ethanol (150 mL) was hydrogenated at 35 psi (2.4×10$^5$ Pa) hydrogen pressure on a Parr apparatus for 1 day. After workup, the reaction was not complete and was subjected to the reaction conditions again for 8 days with fresh catalyst. The mixture was filtered through CELITE filter agent and the filtrate was concentrated to yield an oil that contained a 13:1 ratio of the desired amine product, 1-(aminomethyl)cyclopentanol, to the corresponding hydroxylamine. The oil was concentrated from toluene to remove the ethanol and used in the next experiment without further purification.

Part C

To a solution of 1-(aminomethyl)cyclopentanol (approximately 55.2 mmol, prepared as described above) in dichloromethane (280 mL) was added triethylamine (7.76 mL, 55.7 mmol) and 4-chloro-3-nitroquinoline (9.22 g, 44.3 mmol). The mixture was allowed to stand at room temperature over the weekend. A solid formed that was isolated by filtration. Two more crops of solid were isolated from the mother liquor. The yellow solid was stirred in water and filtered. The solid was washed with water multiple times and was dried under vacuum with heat to give 8.29 g of 1-{[(3-nitroquinolin-4-yl)amino]methyl}cyclopentanol as yellow crystals.

Part D

A mixture of 1-{[(3-nitroquinolin-4-yl)amino]methyl}cyclopentanol (8.26 g, 28.8 mmol) and 5% platinum on carbon (0.9 g) in ethanol (200 mL) was hydrogenated on a Parr apparatus overnight. The mixture was filtered through CELITE filter agent and the filtrate was concentrated. The product 1-{[(3-aminoquinolin-4-yl)amino]methyl}-1-cyclopentanol was concentrated from toluene and dichloromethane to remove residual ethanol, then used immediately in the next step.

Part E

To a solution of 1-{[(3-aminoquinolin-4-yl)amino]methyl}cyclopentanol (approximately 28.8 mmol) in dichloromethane (200 mL) at 0° C. was added triethylamine (4.41 mL, 31.6 mmol) and ethoxyacetyl chloride (88% purity, 3.96 g, 30.2 mmol). After 3 hours at room temperature, the solution was concentrated and ethanol (260 mL) and triethylamine (14 mL) were added. The resulting solution was heated at reflux for 18 hours and then concentrated under reduced pressure. The residue was partitioned between dichloromethane and water. The organic layer was washed with brine twice, dried over MgSO$_4$, filtered, and concentrated to yield an oil that formed a white solid when acetonitrile was added. The mixture was sonicated briefly and filtered. The white powder was dried under vacuum to provide 4.55 g of 1-{[2-(ethoxymethyl)-1H-imidazo[4,5-c]quinolin-1-yl]methyl}cyclopentanol.

Part F

Sodium hydride (60% dispersion in oil, 36 mg, 0.8 mmol) was added to a stirred solution of 1-{[2-(ethoxymethyl)-1H-imidazo[4,5-c]quinolin-1-yl]methyl}cyclopentanol (1.45 g, 4.50 mmol) and methyl vinyl sulfone (0.95 g, 8.9 mmol) in tetrahydrofuran (18 mL). The reaction mixture was stirred at room temperature for 1 hour and additional methyl vinyl sulfone (0.47 g) was added. Water (50 mL) was added and the mixture was extracted with ethyl acetate (3×50 mL). The organic layers were combined, washed with brine, dried over sodium sulfate, filtered, and concentrated under reduced pressure to afford an oil that was purified by flash chromatography (silica gel, eluted with 5% methanol in dichloromethane) to provide 1.2 g of 2-(ethoxymethyl)-1-({1-[2-(methylsulfonyl)ethoxy]cyclopentyl}methyl)-1H-imidazo[4,5-c]quinoline as a colorless oil.

Part G

Using the method of Example 4 Part B, the material from Part F was oxidized to provide 2-(ethoxymethyl)-1-({1-[2-(methylsulfonyl)ethoxy]cyclopentyl}methyl)-1H-imidazo[4,5-c]quinoline 5-oxide as a pale orange oil, which was used in the next step without purification.

Part H

Using the method of Example 4 Part C, the material from Part G was aminated. The crude product was purified by flash chromatography (silica gel, 5% methanol in dichloromethane) to provide a foam that was crystallized from ethyl acetate to yield 0.60 g of 2-(ethoxymethyl)-1-({1-[2-(methylsulfonyl)ethoxy]cyclopentyl}methyl)-1H-imidazo[4,5-c]quinolin-4-amine as white, crystalline plates, mp 163-165° C.

$^1$H NMR (300 MHz, DMSO-d$_6$) δ 8.24 (d, J=8.1 Hz, 1H), 7.61 (d, J=8.1 Hz, 1H), 7.44 (t, J=8.1 Hz, 1H), 7.25 (t, J=8.1 Hz, 1H), 6.60 (bs, 2H), 4.94 (s, 2H), 4.83 (s, 2H), 3.62 (t, J=5.6 Hz, 2H), 3.54 (q, J=6.9 Hz, 2H), 3.14 (t, J=5.6 Hz, 2H), 2.81 (s, 3H) 1.85 (m, 2H), 1.59-1.57 (m, 6H), 1.15 (t, J=6.9 Hz, 3H);

MS (APCI) m/z 447 (M+H)$^+$;

Anal. Cacld for C$_{22}$H$_{30}$N$_4$O$_4$S: C, 59.17; H, 6.77: N, 12.55. Found: C, 59.07; H, 6.84; N, 12.32.

Example 24

2-(Ethoxymethyl)-1-({1-[2-(methylsulfonyl)ethoxy]cyclohexyl}methyl)-1H-imidazo[4,5-c]quinolin-4-amine

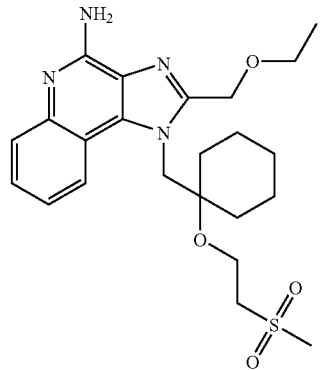

Part A

To a mixture of 4-chloro-3-nitroquinoline (6.30 g, 30.2 mmol) in dichloromethane (100 mL) at 0° C. was added triethylamine (0.1 mL). To the resulting solution was added 1-aminomethyl-1-cyclohexanol hydrochloride (5.00 g, 30.2 mmol), then triethylamine (4.1 mL) and tetrahydrofuran (20 mL). The mixture was allowed to warm to room temperature and more triethylamine (4.2 mL) was added. The yellow mixture was stirred overnight, then was concentrated to about half the volume and heated at reflux for 1 hour. The mixture was concentrated under reduced pressure and the resulting solid was partitioned between 1 M aqueous NaOH (100 mL) and CH$_2$Cl$_2$ (200 mL). The organic layer was washed with water (2×50 mL) and brine (50 mL), dried over MgSO$_4$, filtered, and concentrated to provide a yellow solid that was crystallized from hot isopropanol to yield yellow crystals (9.04 g). $^1$H NMR analysis of the yellow crystals showed a 1:1.4 mixture of isopropyl alcohol to 1-{[(3-nitroquinolin-4-yl)amino]methyl}cyclohexanol. Based on the $^1$H NMR result, the mass of the 1-{[(3-nitroquinolin-4-yl)amino]methyl}cyclohexanol in the mixture was calculated (7.88 g). The product (87% pure) was used without further purification in the next step.

Part B

A mixture of the 1-{[(3-nitroquinolin-4-yl)amino]methyl}cyclohexanol prepared above (87% purity, 7.00 g, 20.3 mmol) and 5% platinum on carbon (0.60 g) in toluene (160 mL) and ethanol (20 mL) was hydrogenated at 20-30 psi (1.4×10$^5$ to 2.1×10$^5$ Pa) on a Parr apparatus for 2 hours. The mixture was filtered through CELITE filter agent, which was rinsed with toluene. The filtrate was concentrated to an oil and the oil was concentrated twice from toluene. To the oil was added CH$_2$Cl$_2$ (200 mL). The resulting solution was cooled in an ice bath and triethylamine (3.11 mL, 22.3 mmol) was added followed by dropwise addition of ethoxyacetyl chloride (88% purity, 2.96 g, 21.3 mmol). The solution was allowed to warm to room temperature and stir for 1 hour, during which time a precipitate formed. The reaction mixture was concentrated to a yellow foam to which ethanol (200 mL) and triethylamine (11 mL) were added. The resulting solution was heated at reflux for 13 hours. The solution was concentrated to a yellow solid, which was dissolved in $CH_2Cl_2$ (150 mL) and washed with water (50 mL) and brine (75 mL). The organic layer was dried over $MgSO_4$, filtered, and concentrated to a solid that was crystallized from $CHCl_3/CH_2Cl_2$ to yield 1.94 g of 1-{[2-(ethoxymethyl)-1H-imidazo[4,5-c]quinolin-1-yl]methyl}cyclohexanol as pale orange crystals after drying.

Part C

Sodium hydride (60% dispersion in oil, 25 mg, 0.62 mmol) followed by methyl vinyl sulfone (1.30 g, 12.4 mmol) were added to a stirred solution of 1-{[2-(ethoxymethyl)-1H-imidazo[4,5-c]quinolin-1-yl]methyl}cyclohexanol (2.1 g, 6.2 mmol) in tetrahydrofuran (25 mL). The reaction mixture was heated at reflux for 2 hours and additional methyl vinyl sulfone (1 equivalent) and sodium hydride (60% dispersion in oil, spatula tip full) were added. The mixture was allowed to stir overnight at room temperature. Water (50 mL) was added and a precipitate formed that was removed by filtration. The filtrate was extracted with dichloromethane (2×50 mL). The organic layers were combined, washed with brine, dried over sodium sulfate, filtered, and concentrated under reduced pressure to afford an oil that was purified by flash chromatography (silica gel, eluted with 5% methanol in dichloromethane) to provide 0.45 g of 2-(ethoxymethyl)-1-({1-[2-(methylsulfonyl)ethoxy]cyclohexyl}methyl)-1H-imidazo[4,5-c]quinoline as a colorless oil.

Part D

Using the method of Example 4 Part B, the material from Part C was oxidized to provide 2-(ethoxymethyl)-1-({1-[2-(methylsulfonyl)ethoxy]cyclohexyl}methyl)-1H-imidazo[4,5-c]quinoline 5-oxide as an orange oil, which was used in the next step without purification.

Part E

Using the method of Example 4 Part C, the material from Part D was aminated. The crude product was purified by flash chromatography (silica gel, 5% methanol in dichloromethane) to provide a foam that was crystallized from ethyl acetate to provide 0.25 g of 2-(ethoxymethyl)-1-({1-[2-(methylsulfonyl)ethoxy]cyclohexyl}methyl)-1H-imidazo[4,5-c]quinolin-4-amine as colorless plates, mp 159-161° C.

$^1$H NMR (300 MHz, DMSO-$d_6$) δ 8.27 (d, J=8.1 Hz, 1H), 7.61 (d, J=8.1 Hz, 1H), 7.44 (t, J=8.1 Hz, 1H), 7.27 (t, J=8.1 Hz, 1H), 6.61 (bs, 2H), 4.83 (s, 2H), 4.81 (s, 2H), 3.67 (t, J=5.6 Hz, 2H), 3.55 (q, J=6.9 Hz, 2H), 3.18 (t, J=5.6 Hz, 2H), 2.90 (s, 3H) 1.77-1.74 (m, 2M), 1.52-1.38 (m, 7H), 1.16 (t, J=6.9 Hz, 3H), 1.10 (m, 1H);

MS (APCI) m/z 461 (M+H);

Anal. Cacld for $C_{23}H_{32}N_4O_4S$: C, 59.98; H, 7.00: N, 12.16. Found: C, 59.98; H, 7.07; N, 12.07.

Example 25

2-Hexyl-1-{2-[2-(methylsulfonyl)ethoxy]ethyl}-1H-imidazo[4,5-c]quinolin-4-amine

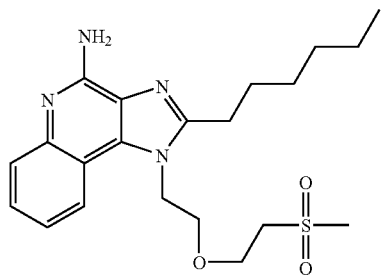

Part A

Heptanoyl chloride (1 mL, 6.5 mmol) was added dropwise to a solution of $N^4$-{2-[2-(methylsulfonyl)ethoxy]ethyl}quinoline-3,4-diamine (prepared as described in Parts A-E of Example 1, approximately 1.8 g, approximately 5.9 mmol) in acetonitrile (30 mL). The reaction mixture was allowed to stir for 1 hour at room temperature, then was concentrated under reduced pressure to yield N-[4-({2-[2-(methylsulfonyl)ethoxy]ethyl}amino)quinoline-3-yl]heptanamide hydrochloride as an orange foam that was used without purification.

Part B

The material from Part A was combined with ethanol (20 mL) and triethylamine (2.5 mL) to yield a solution that was heated at reflux for 10 hours. The solution was allowed to cool to room temperature, then was concentrated under reduced pressure to afford a brown solid. The solid was purified by flash chromatography (silica gel, 5% methanol in dichloromethane) to provide 2.15 g of 2-hexyl-1-{2-[2-(methylsulfonyl)ethoxy]ethyl}-1H-imidazo[4,5-c]quinoline as an off-white solid.

Part C

Using the method of Example 4 Part B, the material from Part B was oxidized to provide 2-hexyl-1-{2-[2-(methylsulfonyl)ethoxy]ethyl}-1H-imidazo[4,5-c]quinoline 5-oxide as an orange solid, which was used in the next step without purification.

Part D

Using the method of Example 4 Part C, the material from Part C was aminated. The crude product was purified by flash chromatography (silica gel, 5% methanol in dichloromethane) to provide a powder that was crystallized from acetonitrile to provide 1.3 g of 2-hexyl-1-{2-[2-(methylsulfonyl)ethoxy]ethyl}-1H-imidazo[4,5-c]quinolin amine as crystalline plates, mp 158-160° C.

$^1$H NMR (300 MHz, DMSO-$d_6$) δ 8.04 (d, J=8.1 Hz, 1H), 7.61 (d, J=8.0 Hz, 1H), 7.41 (t, J=8.0 Hz, 1H), 7.23 (t, J=8.0 Hz, 1H), 6.43 (bs, 2H), 4.73 (t, J=5.6 Hz, 2H), 3.89 (t, J=5.6 Hz, 2H), 3.72 (t, J=5.6 Hz, 2H), 3.27 (t, J=5.6 Hz, 2H), 2.93 (t, J=7.5 Hz, 2H), 2.76 (s, 3H), 1.81 (pentet, J=7.5 Hz, 2H), 1.45-1.39 (m, 2H), 1.36-1.31 (m, 4H), 0.89 (t, J=7.5 Hz, 3H);

MS (APCI) m/z 419 (M+H)$^+$;

Anal. Cacld for $C_{21}H_{30}N_4O_3S$: C, 60.26; H, 7.22: N, 13.39. Found: C, 60.33; H, 7.19; N, 13.38.

Example 26

2-(Ethoxymethyl)-1-({1-[2-(methylsulfonyl)ethoxy]cyclobutyl}methyl)-1H-imidazo[4,5-c]quinolin-4-amine

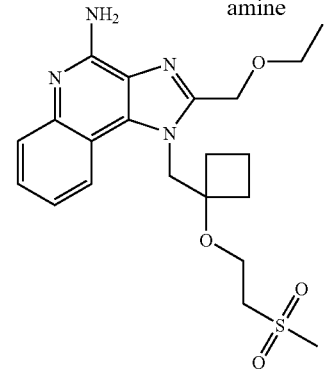

Part A

To a solution of cyclobutanone (10.0 g, 143 mmol) and nitromethane (12 mL) in ethanol (10 mL) was added sodium ethoxide in ethanol (2.67 M, 2.7 mL, 7.2 mmol). The mixture was stirred for 6 days at room temperature. Water was added and the mixture was extracted with ethyl acetate (3×). The organic phases were combined, washed with water and brine, dried over $Na_2SO_4$, filtered, and concentrated. The volatiles were removed by distillation under vacuum to provide 8.51 g of 1-(nitromethyl)cyclobutanol as a yellow liquid.

Part B

A mixture of 1-(nitromethyl)cyclobutanol (8.2 g, 62.5 mmol) and 20% palladium hydroxide on carbon (1.0 g) in ethanol (200 mL) was hydrogenated at 40 psi ($2.8 \times 10^5$ Pa) on a Parr apparatus for 6 days. More 20% palladium hydroxide on carbon (1.2 g) was added and the mixture was hydrogenated at 40 psi ($2.8 \times 10^5$ Pa) for an additional 5 days. The mixture was filtered through CELITE filter agent, which was rinsed with ethanol. The filtrate was concentrated to an oil that was concentrated from dichloromethane and chloroform to remove residual ethanol. 1-(Aminomethyl)cyclobutanol was obtained as an off white solid (6.15 g) that was used without further purification in the next step.

Part C

To a solution of 1-(aminomethyl)cyclobutanol (62.5 mmol) in dichloromethane (312 mL) was added triethylamine (8.71 mL, 62.5 mmol) and 4-chloro-3-nitroquinoline (13.04 g, 62.5 mmol). More triethylamine (3 mL) was added almost immediately. The reaction was stirred under $N_2$ for 10 days at room temperature, then was diluted with dichloromethane and washed with 1 M aqueous NaOH. A solid formed and was isolated by filtration. The organic layer was washed with water and brine, dried over $Na_2SO_4$, filtered, and concentrated under reduced pressure to yield a solid that was crystallized from 2-propanol. The resulting crystals were combined with the solid that was isolated from the extraction and the mixture was triturated with hot 2-propanol. The solid was isolated by filtration, washed with diethyl ether, and air dried to yield 12.83 g of 1-{[(3-nitroquinolin-4-yl)amino]methyl}cyclobutanol as yellow crystals.

Part D

A mixture of 1-{[(3-nitroquinolin-4-yl)amino]methyl}cyclobutanol (6.32 g, 23.1 mmol) and 20% palladium hydroxide on carbon (0.60 g) in ethanol (100 mL) was hydrogenated overnight on a Parr apparatus at 40 psi ($2.8 \times 10^5$ Pa). The mixture was filtered through CELITE filter agent, which was rinsed several times with ethanol, and the filtrate was concentrated to provide 5.66 g of 1-{[(3-aminoquinolin-4-yl)amino]methyl}cyclobutanol as a pale yellow solid. The solid was concentrated from toluene and chloroform to remove ethanol before using directly in the next reaction.

Part E

To a mixture of 1-{[(3-aminoquinolin-4-yl)amino]methyl}cyclobutanol (23.1 mmol, prepared as described in Part D) in dichloromethane (154 mL) and triethylamine (3.54 mL, 25.4 mmol) at 0° C. was added chloroform (100 mL). The mixture was allowed to warm to room temperature and approximately two thirds of the starting material dissolved. To the mixture was slowly added ethoxyacetyl chloride (88% purity, 3.1 g, 24.3 mmol). The solution was stirred at room temperature for 2 hours. More triethylamine (2 mL) and ethoxyacetyl chloride (88% purity, 1.0 g) were added. After an additional 16 hours, the reaction solution was concentrated under reduced pressure. To the residue was added ethanol (190 mL) and triethylamine (13 mL). The resulting solution was heated at reflux for 20 hours and then was concentrated under reduced pressure to yield a yellow solid. The solid was partitioned between dichloromethane (400 mL) and water (100 mL). The organic layer was washed with water (100 mL) and brine (100 mL), dried over $MgSO_4$, filtered, and concentrated under reduced pressure. The crude product was crystallized from acetonitrile and the crystals were isolated by filtration to provide 4.52 g of 1-{[2-(ethoxymethyl)-1H-imidazo[4,5-c]quinolin-1-yl]methyl}cyclobutanol.

Part F 1,8-Diazabicyclo[5.4.0]undec-7-ene (0.10 mL, 0.74 mmol) followed by methyl vinyl sulfone (1.60 g, 14.8 mmol) were added to a stirred solution of 1-{[2-(ethoxymethyl)-1H-imidazo[4,5-c]quinolin-1-yl]methyl}cyclobutanol (2.30 g, 7.39 mmol) in tetrahydrofuran (30 mL). The reaction mixture was stirred at room temperature for 1 hour and a small amount of sodium hydride (60% dispersion in mineral oil) was added. Water (50 mL) was added and the mixture was extracted with ethyl acetate (3×50 mL). The organic layers were combined, washed with brine, dried over sodium sulfate, filtered, and concentrated under reduced pressure to afford an oil that was purified by flash chromatography (silica gel, eluted with 5% methanol in dichloromethane) to provide 2.0 g of 2-(ethoxymethyl)-1-({1-[2-(methylsulfonyl)ethoxy]cyclobutyl}methyl)-1H-imidazo[4,5-c]quinoline as an oil.

Part G

Using the method of Example 4 Part B, the material from Part F was oxidized to provide 2-(ethoxymethyl)-1-({1-[2-(methylsulfonyl)ethoxy]cyclobutyl}methyl)-1H-imidazo[4,5-c]quinoline 5-oxide as an orange solid, which was used in the next step without purification.

Part H

Using the method of Example 4 Part C, the material from Part G was aminated. The crude product was purified by flash chromatography (silica gel, 5% methanol in dichloromethane) to provide a foam that was crystallized from acetonitrile/ethanol to provide 1.2 g of 2-(ethoxymethyl)-1-({1-[2-(methylsulfonyl)ethoxy]cyclobutyl}methyl)-1H-imidazo[4,5-c]quinolin-4-amine as off-white, crystalline plates, mp 221-223° C.

$^1$H NMR (300 MHz, DMSO-$d_6$) δ 8.31 (d, J=8.1 Hz, 1H), 7.60 (d, J=8.1 Hz, 1H), 7.43 (t, J=8.1 Hz, 1H), 7.24 (t, J=8.1 Hz, 1H), 6.58 (bs, 2H), 4.95 (s, 2H), 4.85 (s, 2H), 3.77 (t, J=5.6 Hz, 2H), 3.53 (q, J=6.9 Hz, 2H), 3.22 (t, J=5.6 Hz, 2H), 2.78 (s, 3H) 2.31-2.24 (m, 2H), 1.97-1.92 (m, 2H), 1.77-1.70 (m, 2H), 1.14 (t, J=6.9 Hz, 3H);

MS (APCI) m/z 433 (M+H)$^+$;

Anal. Calcd for $C_{21}H_{28}N_4O_4S$: C, 58.31; H, 6.52: N, 12.95. Found: C, 58.13; H, 6.84; N, 12.85.

Example 27

2-(Ethoxymethyl)-1-({1-[2-(methylsulfonyl)ethoxy]cyclobutyl}methyl)-6,7,8,9-tetrahydro-1H-imidazo[4,5-c]quinolin-4-amine

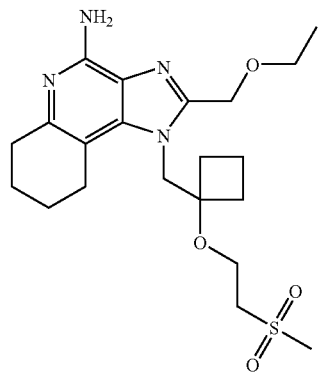

A mixture of 2-(ethoxymethyl)-1-({1-[2-(methylsulfonyl)ethoxy]cyclobutyl}methyl)-1H-imidazo[4,5-c]quinolin-4-amine (prepared as described in Example 26, 0.500 g, 1.16 mmol) and platinum(IV) oxide (0.5 g) in trifluoroacetic acid (5 mL) was hydrogenated on a Parr apparatus at 50 psi (3.5× $10^5$ Pa) hydrogen pressure for 1 day. The mixture was filtered through CELITE filter agent, which was washed afterwards with dichloromethane. The filtrate was concentrated under reduced pressure to afford an oil that was suspended in water (20 mL) and adjusted to pH 13 with 50% aqueous sodium hydroxide. A white solid formed that was isolated by filtration, washed with water, and recrystallized from acetonitrile. The crystals were isolated and dried under vacuum at 65° C. to afford 0.35 g of 2-(ethoxymethyl)-1-({1-[2-(methylsulfonyl)ethoxy]cyclobutyl}methyl)-6,7,8,9-tetrahydro-1H-imidazo[4,5-c]quinolin-4-amine as a white powder, mp 186-188° C.

$^1$H NMR (300 MHz, DMSO-$d_6$) δ 5.84 (bs, 2H), 4.72 (bs, 2H), 4.56 (bs, 2H), 3.72 (t, J=5.6 Hz, 2H), 3.48 (q, J=6.9 Hz, 2H), 3.29 (t, J=5.6 Hz, 2H), 2.94 (m, 2H), 2.81 (s, 3H) 2.67 (m, 2H), 2.25-2.19 (m, 2H), 1.88-1.80 (m, 3H), 1.75 (m, 4H), 1.54-1.51 (m, 1H), 1.11 (t, J=6.9 Hz, 3H);

MS (APCI) m/z 437 (M+H)$^+$;

Anal. Cacld for $C_{21}H_{32}N_4O_4S$: C, 57.77; H, 7.39: N, 12.83. Found: C, 57.65; H, 7.56; N, 13.06.

Example 28

2-(Ethoxymethyl)-1-{2-methyl-2-[2-(methylsulfonyl)ethoxy]propyl}-6,7,8,9-tetrahydro-1H-imidazo[4,5-c]quinolin-4-amine

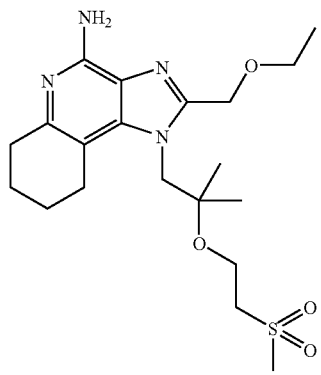

A mixture of 2-(ethoxymethyl)-1-{2-methyl-2-[2-(methylsulfonyl)ethoxy]propyl}-1H-imidazo[4,5-c]quinolin-4-amine (prepared as described in Example 9, 1.70 g, 4.04 mmol) and platinum(IV) oxide (1.0 g) in trifluoroacetic acid (20 mL) was hydrogenated on a Parr apparatus at 50 psi (3.5×$10^5$ Pa) hydrogen pressure for 40 hours. The mixture was filtered through CELITE filter agent, which was washed afterwards with dichloromethane. The filtrate was concentrated under reduced pressure to afford an oil that was suspended in water (20 mL) and adjusted to pH 13 with 50% aqueous sodium hydroxide. The mixture was extracted with dichloromethane (3×50 mL). The organic layers were combined, dried over sodium sulfate, filtered, and concentrated under reduced pressure to yield a white solid. The solid was recrystallized from toluene to afford 1.3 g of 2-(ethoxymethyl)-1-{2-methyl-2-[2-(methylsulfonyl)ethoxy]propyl}-6,7,8,9-tetrahydro-1H-imidazo[4,5-c]quinolin-4-amine as a white, fluffy powder, mp 150-153° C.

$^1$H NMR (300 MHz, DMSO-$d_6$) δ 5.80 (bs, 2H), 4.75 (bs, 2H), 4.42 (bs, 2H), 3.62 (t, J=5.6 Hz, 2H), 3.45 (q, J=6.9 Hz, 2H), 3.21 (t, J=5.6 Hz, 2H), 2.91 (m, 2H), 2.68 (m, 5H), 1.75 (m, 4H), 1.13-1.08 (m, 9H);

MS (APCI) m/z 425 (M+H)$^+$;

Anal. Cacld for $C_{20}H_{32}N_4O_4S.0.25H_2O$: C, 55.99; H, 7.63: N, 13.06. Found: C, 56.04; H, 7.86; N, 13.07.

Example 29

1-{2-Methyl-2-[2-(methylsulfonyl)ethoxy]propyl}-1H-imidazo[4,5-c]quinolin-4-amine

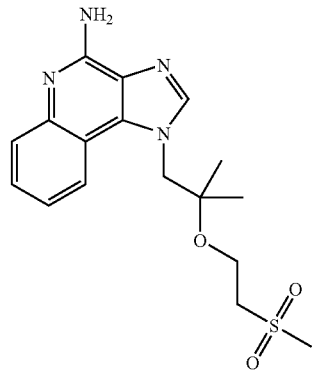

Part A

Sodium hydride (60% dispersion in mineral oil, 58 mg, 1.45 mmol) was added to a stirred solution of 1-(4-chloro-1H-imidazo[4,5-c]quinolin-1-yl)-2-methylpropan-2-ol (described in U.S. Pat. No. 4,689,338 Example 189, Part D, 4.00 g, 14.5 mmol) in tetrahydrofuran (58 mL). After 5 minutes, methyl vinyl sulfone (3.10 g, 29.0 mmol) was added dropwise. The reaction mixture was stirred at room temperature for 17 hours. The volatiles were removed under reduced pressure and the resulting oil was purified by flash chromatography (silica gel, eluted with 5% methanol in dichloromethane) to yield 4.3 g of 4-chloro-1-{2-methyl-2-[2-(methylsulfonyl)ethoxy]propyl}-1H-imidazo[4,5-c]quinoline as a foam.

Part B

A suspension of 4-chloro-1-{2-methyl-2-[2-(methylsulfonyl)ethoxy]propyl}-1H-imidazo[4,5-c]quinoline (4.30 g, 11.3 mmol) in a solution of ammonia in methanol (7 M, 43 mL) in a high pressure vessel was heated at 150° C. for 12 hours. The vessel was allowed to cool to room temperature. The mixture was concentrated under reduced pressure to afford a solid that was slurried in water (50 mL), saturated aqueous sodium carbonate, and methanol. The solid was isolated by filtration, washed with water, and purified by flash chromatography (silica gel, eluted with 10% methanol in dichloromethane) to provide a white solid. The solid was heated in methanol (200 mL) at reflux, isolated by filtration, washed with methanol, and dried to yield 2.2 g of 1-{2-methyl-2-[2-(methylsulfonyl)ethoxy]propyl}-1H-imidazo[4,5-c]quinolin-4-amine as a white powder, mp 261-264° C.

$^1$H NMR (300 MHz, DMSO-$d_6$) δ 8.30 (d, J=8.1 Hz, 1H), 8.12 (s, 1H), 7.61 (d, J=8.1 Hz, 1H), 7.43 (t, J=8.1 Hz, 1H), 7.23 (t, J=8.1 Hz, 1H), 6.54 (bs, 2H), 4.68 (bs, 2H), 3.71 (t, J=5.6 Hz, 2H), 3.15 (t, J=5.6 Hz, 2H), 2.71 (s, 3H), 1.22 (bs, 6H); MS (APCI) m/z 363 (M+H)$^+$;

Anal. Cacld for $C_{17}H_{22}N_4O_3S.0.25H_2O$: C, 55.64; H, 6.18: N, 15.27. Found: C, 55.69; H, 6.20; N, 15.04.

Example 30

2-Methyl-1-{2-methyl-2-[2-(methylsulfonyl)ethoxy]propyl}-6,7,8,9-tetrahydro-1H-imidazo[4,5-c]quinolin-4-amine

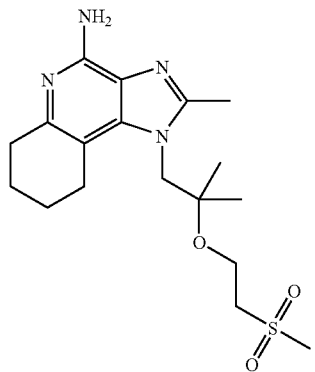

A mixture of 2-methyl-1-{2-methyl-2-[2-(methylsulfonyl)ethoxy]propyl}-1H-imidazo[4,5-c]quinolin-4-amine (prepared as described in Example 21, 1.70 g, 4.52 mmol) and platinum(IV) oxide (1.0 g) in trifluoroacetic acid (23 mL) was hydrogenated on a Parr apparatus at 50 psi ($3.5 \times 10^5$ Pa) hydrogen pressure for 20 hours. The mixture was filtered through CELITE filter agent, which was washed afterwards with dichloromethane. The filtrate was concentrated under reduced pressure to afford an oil that was suspended in water (50 mL) and adjusted to pH 12 with 50% aqueous sodium hydroxide. A white solid formed that was isolated by filtration, washed with water, and recrystallized from ethanol. The crystals were isolated and dried under vacuum at 65° C. to afford 1.10 g of 2-methyl-1-{2-methyl-2-[2-(methylsulfonyl)ethoxy]propyl}-6,7,8,9-tetrahydro-1H-imidazo[4,5-c]quinolin-4-amine as white crystals, mp 226-229° C.

$^1$H NMR (300 MHz, DMSO-$d_6$) δ 5.64 (bs, 2H), 4.30 (bs, 2H), 3.62 (t, J=5.6 Hz, 2H), 3.18 (t, J=5.6 Hz, 2H), 2.92 (m, 2H), 2.65 (m, 2H), 2.63 (s, 3H), 2.51 (s, 3H), 1.74 (m, 4H), 1.13 (bs, 6H); MS (APCI) m/z 381 (M+H)$^+$;

Anal. Calcd for $C_{18}H_{28}N_4O_3S$: C, 56.82; H, 7.42: N, 14.72. Found: C, 56.81; H, 7.63; N, 14.69.

Example 31

1-{2-Methyl-2-[2-(methylsulfonyl)ethoxy]propyl}-6,7,8,9-tetrahydro-1H-imidazo[4,5-c]quinolin-4-amine

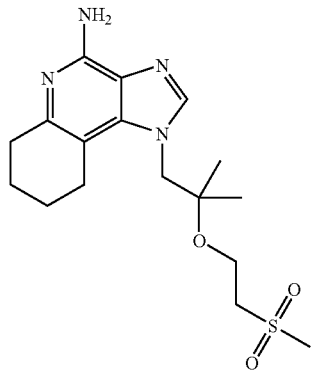

A mixture of 1-{2-methyl-2-[2-(methylsulfonyl)ethoxy]propyl}-1H-imidazo[4,5-c]quinolin-4-amine (prepared as described in Example 29, 1.00 g, 2.76 mmol) and platinum (IV) oxide (0.5 g) in trifluoroacetic acid (14 mL) was hydrogenated on a Parr apparatus at 50 psi ($3.5 \times 10^5$ Pa) hydrogen pressure for 20 hours. The mixture was filtered through CELITE filter agent, which was washed afterwards with dichloromethane. The filtrate was concentrated under reduced pressure to afford an oil that was suspended in water (50 mL) and adjusted to pH 13 with 50% aqueous sodium hydroxide. A white solid formed that was isolated by filtration, washed with water, and dried under vacuum at 65° C. to afford 1.10 g of 1-{2-methyl-2-[2-(methylsulfonyl)ethoxy]propyl}-6,7,8,9-tetrahydro-1H-imidazo[4,5-c]quinolin-4-amine as a white powder, mp 219-223° C.

$^1$H NMR (300 MHz, DMSO-$d_6$) δ 7.90 (s, 1H), 5.76 (bs, 2H), 4.31 (bs, 2H), 3.70 (t, J=5.6 Hz, 2H), 3.27 (t, J=5.6 Hz, 2H), 2.93 (m, 2H), 2.76 (s, 3H), 2.66 (m, 2H), 1.75 (m, 4H), 1.12 (bs, 6H);

MS (APCI) m/z 367 (M+H)$^+$;

Anal. Calcd for $C_{17}H_{26}N_4O_3S$: C, 55.72; H, 7.15: N, 15.29. Found: C, 55.49; H, 7.32; N, 15.16.

Example 32

2-Butyl-1-{2-methyl-2-[2-(methylsulfonyl)ethoxy]propyl}-1H-imidazo[4,5-c]quinolin-4-amine

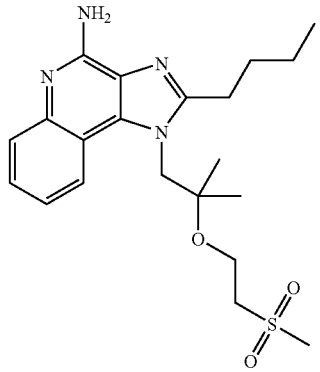

Part A

Trimethyl orthovalerate (3.6 mL, 21 mmol) and pyridine hydrochloride (0.22 g, 1.9 mmol) were added to a solution of 1-[(3-aminoquinolin-4-yl)amino]-2-methylpropan-2-ol (prepared as described in Part A of Example 8, approximately 4.4 g, 19 mmol) in acetonitrile (96 mL). The reaction mixture was heated at reflux for 1 hour, then was allowed to cool to room temperature and was concentrated under reduced pressure. The crude product was purified by flash chromatography (silica gel, eluted with 5% methanol in dichloromethane) to yield 4.1 g of 1-(2-butyl-1H-imidazo[4,5-c]quinolin-1-yl)-2-methylpropan-2-ol as a white foam.

Part B

Sodium hydride (60% dispersion in oil, 55 mg, 1.38 mmol) was added to a stirred solution of 1-(2-butyl-1H-imidazo[4,5-c]quinolin-1-yl)-2-methylpropan-2-ol (4.10 g, 13.8 mmol) in tetrahydrofuran (55 mL). After 5 minutes, methyl vinyl sulfone (2.90 g, 27.6 mmol) was added dropwise. The reaction mixture was stirred at room temperature for 1 hour. Water (50 mL) and a small amount of brine were added and the mixture was extracted with ethyl acetate (2×50 mL). The organic layers were combined, washed with brine, dried over sodium sulfate, filtered, and concentrated under reduced pressure to afford a solid that was purified by flash chromatography (silica gel, eluted with 5% methanol in dichloromethane) to provide 2.7 g of 2-butyl-1-{2-methyl-2-[2-(methylsulfonyl)ethoxy]propyl}-1H-imidazo[4,5-c]quinoline as a white solid.

Part C

Using the method of Example 4 Part B, the material from Part B was oxidized to provide 2-butyl-1-{2-methyl-2-[2-(methylsulfonyl)ethoxy]propyl}-1H-imidazo[4,5-c]quinoline 5-oxide as an orange solid, which was used in the next step without purification.

Part D

Using the method of Example 4 Part C, the material from Part C was aminated. The crude product was purified by flash chromatography (silica gel, eluted with 5% methanol in dichloromethane) to provide 2.2 g of 2-butyl-1-{2-methyl-2-[2-(methylsulfonyl)ethoxy]propyl}-1H-imidazo[4,5-c]quinolin-4-amine as a white foam. A portion of the material (1.2 g) was crystallized from acetonitrile to provide 2-butyl-1-{2-methyl-2-[2-(methylsulfonyl)ethoxy]propyl}-1H-imidazo[4,5-c]quinolin-4-amine as tan needles, mp 196-198° C.

$^1$H NMR (300 MHz, DMSO-$d_6$) δ 8.28 (d, J=8.1 Hz, 1H), 7.58 (d, J=8.1 Hz, 1H), 7.39 (t, J=8.1 Hz, 1H), 7.21 (t, J=8.1 Hz, 1H), 6.40 (bs, 2H), 4.68 (bs, 4H), 3.61 (t, J=5.6 Hz, 2H), 3.02-2.97 (m, 4H), 2.56 (s, 3H) 1.79 (pentet, J=7.5 Hz, 2H), 1.43 (sextet, J=7.5 Hz, 2H), 1.23 (bs, 6H), 0.94 (t, J=7.5 Hz, 3H);

MS (APCI) m/z 419 (M+H)$^+$;

Anal. Cacld for $C_{21}H_{30}N_4O_3S$: C, 60.26; H, 7.22: N, 13.39. Found: C, 60.04; H, 7.48; N, 13.45.

Example 33

2-Butyl-1-{2-methyl-2-[2-(methylsulfonyl)ethoxy]propyl}-6,7,8,9-tetrahydro-1H-imidazo[4,5-c]quinolin-4-amine

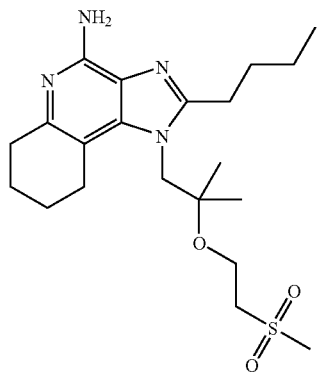

2-Butyl-1-{2-methyl-2-[2-(methylsulfonyl)ethoxy]propyl}-1H-imidazo[4,5-c]quinolin-4-amine (prepared as described in Example 32, 1.05 g, 2.51 mmol) was hydrogenated using the method described in Example 31. After the workup, the white solid was recrystallized from ethyl acetate. The crystals were isolated by filtration and dried under vacuum at 65° C. to afford 0.5 g of 2-butyl-1-{2-methyl-2-[2-(methylsulfonyl)ethoxy]propyl}-6,7,8,9-tetrahydro-1H-imidazo[4,5-c]quinolin-4-amine as a white powder, mp 146-148° C.

$^1$H NMR (300 MHz, DMSO-$d_6$) δ 5.65 (bs, 2H), 4.30 (bs, 2H), 3.60, (t, J=5.6 Hz, 2H), 3.13 (t, J=5.6 Hz, 2H), 2.92 (m, 2H), 2.87 (t, J=7.5 Hz, 2H), 2.66 (m, 2H) 2.58 (s, 3H), 1.74-1.68 (m, 6H), 1.37 (sextet, J=7.5 Hz, 2H), 1.11 (bs, 6H), 0.91 (t, J=7.5 Hz, 3H);

MS (APCI) m/z 423 (M+H);

Anal. Cacld for $C_{21}H_{34}N_4O_3S$: C, 59.69; H, 8.11: N, 13.26. Found: C, 59.53; H, 8.30; N, 13.05.

Example 34

2-(Ethoxymethyl)-1-({1-[2-(methylsulfonyl)ethoxy]cyclopropyl}methyl)-1H-imidazo[4,5-c]quinolin-4-amine

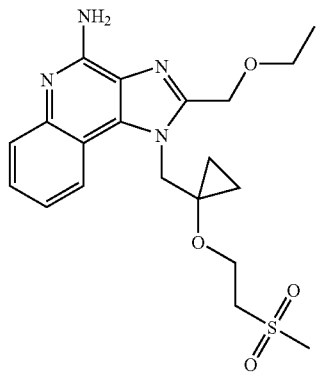

Part A

To a 0° C. mixture of 1-(aminomethyl)cyclopropanol (approximately 36.7 mmol, prepared as described by Lysenko, I. L. and Kulinkovich, O. G. *Russ. i J. Org Chem.* 2001, 17, 1238-1243) and triethylamine (6.30 mL, 45.4 mmol) in dichloromethane (120 mL) was added a solution of 4-chloro-3-nitroquinoline (7.28 g, 34.9 mmol) in dichloromethane (30 mL). The suspension was stirred at room temperature over the weekend. The dichloromethane was removed under reduced pressure and the residue was suspended in water (150 mL) and stirred at room temperature for 3 hours. A solid was isolated by filtration and dried in a vacuum oven to afford 8.99 g of 1-{[(3-nitroquinolin-4-yl)amino]methyl}cyclopropanol as a yellow solid.

Part B

A mixture of 1-{[(3-nitroquinolin-4-yl)amino]methyl}cyclopropanol (3.50 g, 13.5 mmol) and 5% platinum on carbon (350 mg) in ethyl acetate (70 mL) and methanol (7 mL) was hydrogenated under 35 psi (2.4×10$^5$ Pa) on a Parr apparatus for 3 hours. The mixture was filtered through CELITE filter agent, which was rinsed with ethyl acetate. The filtrate was concentrated under reduced pressure to yield 1-{[(3-aminoquinolin-4-yl)amino]methyl}cyclopropanol 1-{[(3-nitroquinolin-yl)amino]methyl}cyclopropanol an orange oil that was used immediately in the next step.

Part C

To a solution of the material from Part B in dichloromethane (60 mL) at 0° C. was added ethoxyacetyl chloride (1.5 mL, 14.9 mmol). The reaction mixture was stirred for 1 hour at 0° C., then was concentrated under reduced pressure. The resulting 2-ethoxy-N-(4-{[(1-hydroxycyclopropyl)methyl]amino}quinolin-3-yl)acetamide was used in the next step without purification.

Part D

The material from Part C was dissolved in ethanol (50 mL) and triethylamine (5.5 mL) was added. The reaction mixture was stirred at 60° C. for 5 hours. The reaction mixture was allowed to cool to room temperature and was concentrated under reduced pressure. The residue was dissolved in dichloromethane (70 mL) and washed with saturated aqueous sodium bicarbonate (50 mL). The aqueous layer was back-extracted with dichloromethane (25 mL). The combined organic layers were dried over magnesium sulfate, filtered, and concentrated under reduced pressure to yield an oil. The oil was triturated with acetonitrile. A solid formed that was isolated by filtration to yield 2.54 g of 1-{[2-(ethoxymethyl)-1H-imidazo[4,5-c]quinolin-1-yl]methyl}cyclopropanol as a tan solid.

Part E

A heterogeneous mixture of 1-{[2-(ethoxymethyl)-1H-imidazo[4,5-c]quinolin-1-yl]methyl}cyclopropanol (0.76 g, 2.6 mmol) and methyl vinyl sulfone (0.54 g, 5.11 mmol) in DMF (10 mL) was heated until a solution formed. Sodium hydride (60% dispersion in oil, 10 mg, 0.26 mmol) was added and the reaction mixture was stirred at room temperature for 1 hour. Water (50 mL) and a small amount of brine were added and the mixture was extracted with ethyl acetate (3×50 mL). The organic layers were combined, washed with brine, dried over sodium sulfate, filtered, and concentrated under reduced pressure to afford an oil that was purified by flash chromatography (silica gel, eluted with 5% methanol in dichloromethane) to provide 0.75 g of 2-(ethoxymethyl)-1-({1-[2-(methylsulfonyl)ethoxy]cyclopropyl}methyl)-1H-imidazo[4,5-c]quinoline as a tan oil.

Part F

Using the method of Example 4 Part B, the material from Part E was oxidized to provide 2-(ethoxymethyl)-1-({1-[2-(methylsulfonyl)ethoxy]cyclopropyl}methyl)-1H-imidazo[4,5-c]quinoline 5-oxide as an orange solid, which was used in the next step without purification.

Part G

Using the method of Example 4 Part C, the material from Part F was aminated. The crude product was purified by flash chromatography (silica gel, eluted with 5% methanol in dichloromethane) to provide 0.66 g of 2-(ethoxymethyl)-1-({1-[2-(methylsulfonyl)ethoxy]cyclopropyl}methyl)-1H-imidazo[4,5-c]quinolin-4-amine as a white foam, which was crystallized from ethyl acetate to afford 0.36 g of tan crystals, mp 169-171° C.

$^1$H NMR (300 MHz, DMSO-$d_6$) δ 8.19 (d, J=8.1 Hz, 1H), 7.62 (d, J=8.1 Hz, 1H), 7.45 (t, J=8.1 Hz, 1H), 7.26 (t, J=8.1 Hz, 1H), 6.63 (bs, 2H), 5.10 (bs, 2H), 4.79 (bs, 2H), 3.86 (t, J=5.6 Hz, 2H), 3.59 (q, J=6.9 Hz, 2H), 3.30 (t, J=5.6 Hz, 2H), 2.92 (s, 3H), 1.18 (t, J=6.9 Hz, 3H), 0.87 (m, 2H), 0.54 (m, 2H);

MS (APCI) m/z 419 (M+H)$^+$;

Anal. Calcd for $C_{20}H_{26}N_4O_4S$: C, 57.40; H, 6.26: N, 13.39. Found: C, 57.26; H, 6.32; N, 13.32.

Example 35

1-{2-Methyl-2-[2-(methylsulfonyl)ethoxy]propyl}-2-propyl-6,7,8,9-tetrahydro-1H-imidazo[4,5-c]quinolin-4-amine

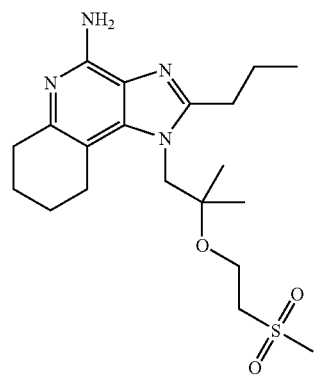

1-{2-Methyl-2-[2-(methylsulfonyl)ethoxy]propyl}-2-propyl-1H-imidazo[4,5-c]quinolin-4-amine (prepared as described in Example 22, 0.8 g, 1.98 mmol) was hydrogenated using the method described in Example 31. After the workup, the white solid was recrystallized from acetonitrile. The crystals were isolated by filtration and dried under vacuum at 65° C. to afford 0.4 g of 1-{2-methyl-2-[2-(methylsulfonyl)ethoxy]propyl}-2-propyl-6,7,8,9-tetrahydro-1H-imidazo[4,5-c]quinolin-4-amine as off-white crystals, mp 188-190° C.

$^1$H NMR (300 MHz, DMSO-$d_6$) δ 5.60 (bs, 2H), 4.31 (bs, 2H), 3.60 (t, J=5.6 Hz, 2H), 3.14 (t, J=5.6 Hz, 2H), 2.93 (m, 2H), 2.85 (t, J=7.5 Hz, 2H), 2.65 (m, 2H) 2.59 (s, 3H), 1.78-1.70 (m, 6H), 1.11 (bs, 6H), 0.95 (t, J=7.5 Hz, 3H);

MS (APCI) m/z 409 (M+H)$^+$;

Anal. Cacld for $C_{20}H_{32}N_4O_3S$: C, 58.80; H, 7.89: N, 13.71. Found: C, 58.67; H, 7.86; N, 13.74.

Example 36

2-Ethyl-1-{2-methyl-2-[2-(methylsulfonyl)ethoxy]propyl}-1H-imidazo[4,5-c]quinolin-4-amine

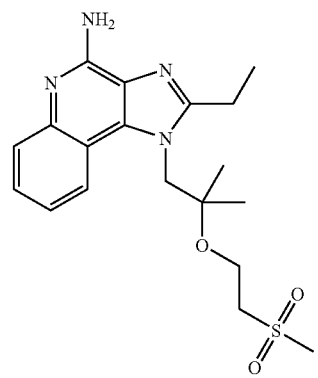

Part A 1-(2-Ethyl-1H-imidazo[4,5-c]quinolin-1-yl)-2-methylpropan-2-ol (4.5 g) was prepared as a white powder using the general method described in Part A of Example 32, with triethyl orthopropionate used in lieu of trimethyl orthovalerate. A Dean Stark apparatus was used to collect approximately 25 mL of solvent during the reaction.

Part B

Sodium hydride (60% dispersion in oil, 30 mg, 0.74 mmol) was added to a stirred solution of 1-(2-ethyl-1H-imidazo[4,5-c]quinolin-1-yl)-2-methylpropan-2-ol (2.00 g, 7.43 mmol) in tetrahydrofuran (30 mL). After five minutes, methyl vinyl sulfone (1.60 g, 14.9 mmol) was added dropwise. The reaction mixture was stirred at room temperature for 1.5 hours and a solid formed. A few drops of water were added to the mixture, which was then concentrated under reduced pressure to yield a solid that was purified by flash chromatography (silica gel, eluted with 5% methanol in dichloromethane) to provide 1.90 g of 2-ethyl-1-{2-methyl-2-[2-(methylsulfonyl)ethoxy]propyl}-1H-imidazo[4,5-c]quinoline as a white solid.

Part C

Using the method of Example 4 Part B, the material from Part B was oxidized to provide 2-ethyl-1-{2-methyl-2-[2-(methylsulfonyl)ethoxy]propyl}-1H-imidazo[4,5-c]quinoline 5-oxide as an off-white foam, which was used in the next step without purification.

Part D

Using the method of Example 4 Part C, the material from Part C was aminated. The crude product was purified by flash chromatography (silica gel, eluted with 5% methanol in dichloromethane) to provide 2.3 g of 2-ethyl-1-{2-methyl-2-[2-(methylsulfonyl)ethoxy]propyl}-1H-imidazo[4,5-c]quinolin-4-amine as a white foam. A portion of the material (1.2 g) was crystallized from acetonitrile to provide 2-ethyl-1-{2-methyl-2-[2-(methylsulfonyl)ethoxy]propyl}-1H-imidazo[4,5-c]quinolin-4-amine as tan, crystalline plates, mp 206-209° C.

$^1$H NMR (300 MHz, DMSO-$d_6$) δ 8.28 (d, J=8.1 Hz, 1H), 7.59 (d, J=8.1 Hz, 1H), 7.40 (t, J=8.1 Hz, 1H), 7.21 (t, J=8.1 Hz, 1H), 6.40 (bs, 2H), 4.67 (bs, 2H), 3.61 (t, J=5.6 Hz, 2H), 3.06-2.99 (m, 4H), 2.57 (s, 3H), 1.35 (t, J=7.5 Hz, 3H), 1.23 (bs, 6H);

MS (APCI) m/z 391 (M+H)$^+$;

Anal. Cacld for $C_{19}H_{26}N_4O_3S$: C, 58.44; H, 6.71: N, 14.35. Found: C, 58.30; H, 6.47; N, 14.48.

Example 37
2-Ethyl-1-{2-methyl-2-[2-(methylsulfonyl)ethoxy]propyl}-6,7,8,9-tetrahydro-1H-imidazo[4,5-c]quinolin-4-amine

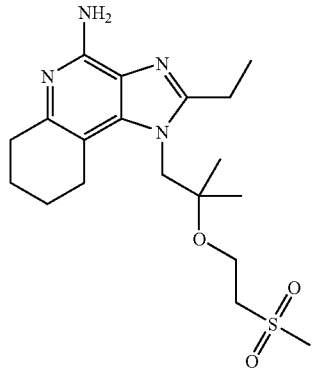

2-Ethyl-1-{2-methyl-2-[2-(methylsulfonyl)ethoxy]propyl}-1H-imidazo[4,5-c]quinolin-4-amine (prepared as described in Example 36, 1.10 g, 2.81 mmol) was hydrogenated using the method described in Example 31. After the workup, the white solid was recrystallized from acetonitrile. The crystals were isolated by filtration and dried under vacuum at 65° C. to afford 0.6 g of 2-ethyl-1-{2-methyl-2-[2-(methylsulfonyl)ethoxy]propyl}-6,7,8,9-tetrahydro-1H-imidazo[4,5-c]quinolin-4-amine as white needles, mp 225-227° C.

$^1$H NMR (300 MHz, DMSO-$d_6$) δ 5.60 (bs, 2H), 4.30 (bs, 2H), 3.61 (t, J=5.6 Hz, 2H), 3.15 (t, J=5.6 Hz, 2H), 2.93-2.85 (m, 4H), 2.66 (m, 2H), 2.60 (s, 3H), 1.74 (m, 4H), 1.27 (t, J=7.5 Hz, 3H), 1.12 (bs, 6H);

MS (APCI) m/z 395 (M+H)$^+$;

Anal. Cacld for $C_{19}H_{30}N_4O_3S$: C, 57.84; H, 7.66: N, 14.20. Found: C, 57.67; H, 7.78; N, 14.24.

Example 38
2-(Methoxymethyl)-1-{2-methyl-2-[2-(methylsulfonyl)ethoxy]propyl}-1H-imidazo[4,5-c]quinolin-4-amine

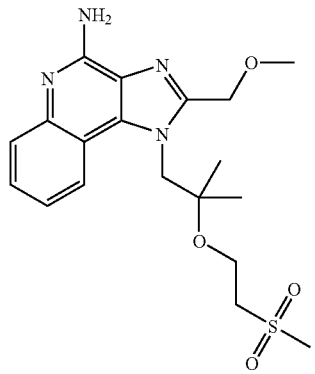

Part A

Methoxyacetyl chloride (2.5 g, 23 mmol) was added dropwise to a solution of 1-[(3-aminoquinolin-4-yl)amino]-2-methylpropan-2-ol (prepared as described in Part A of Example 8, approximately 4.4 g, 19 mmol) in acetonitrile (96 mL). The reaction mixture was stirred for 1 hour at room temperature. A solid formed that was isolated by filtration, washed with acetonitrile, and dried to yield 5.5 g of N-{4-[(2-hydroxy-2-methylpropyl)amino]quinolin-3-yl}-2-methoxyacetamide hydrochloride as a yellow powder.

Part B

A solution of potassium carbonate (3.4 g, 24.3 mmol) in water (9 mL) was added to a stirred suspension of N-{4-[(2-hydroxy-2-methylpropyl)amino]quinolin-3-yl}-2-methoxyacetamide hydrochloride (5.5 g, 16.2 mmol) in ethanol (23 mL). The reaction mixture was heated at reflux for 1.5 hours, then was allowed to cool to room temperature. The mixture was concentrated under reduced pressure to yield an aqueous slurry that was diluted with water (50 mL) and a small amount of brine. The mixture was extracted with dichloromethane (2×50 mL). The organic layers were combined, dried over sodium sulfate, filtered, and concentrated under reduced pressure. The crude oil was purified by flash chromatography (silica gel, 5% methanol in dichloromethane) to yield 4.2 g of 1-[2-(methoxymethyl)-1H-imidazo[4,5-c]quinolin-1-yl]-2-methylpropan-2-ol as an oil that slowly solidified.

Part C

Sodium hydride (60% dispersion in oil, 59 mg, 1.47 mmol) was added to a stirred solution of 1-[2-(methoxymethyl)-1H-imidazo[4,5-c]quinolin-1-yl]-2-methylpropan-2-ol (4.20 g, 14.7 mmol) in tetrahydrofuran (59 mL). After 5 minutes, methyl vinyl sulfone (3.10 g, 29.4 mmol) was added dropwise. The reaction mixture was stirred at room temperature for 17 hours. Water (5 mL) was added and the mixture was concentrated under reduced pressure to afford an oil that was purified by flash chromatography (silica gel, eluted with 5% methanol in dichloromethane) to provide 3.7 g of 2-(methoxymethyl)-1-{2-methyl-2-[2-(methylsulfonyl)ethoxy]propyl}-1H-imidazo[4,5-c]quinoline as a white solid.

Part D

Using the method of Example 4 Part B, the material from Part C was oxidized to provide 2-(methoxymethyl)-1-{2-methyl-2-[2-(methylsulfonyl)ethoxy]propyl}-1H-imidazo[4,5-c]quinoline 5-oxide as an off-white foam, which was used in the next step without purification.

Part E

Using the method of Example 4 Part C, the material from Part D was aminated. The crude product was purified by flash chromatography (silica gel, 5% methanol in dichloromethane) to provide 2.8 g of 2-(methoxymethyl)-1-{2-methyl-2-[2-(methylsulfonyl)ethoxy]propyl}-1H-imidazo[4,5-c]quinolin-4-amine as a white foam. A portion of the material (1.4 g) was crystallized from acetonitrile to provide 2-(methoxymethyl)-1-{2-methyl-2-[2-(methylsulfonyl)ethoxy]propyl}-1H-imidazo[4,5-c]quinolin-4-amine as tan, crystalline plates, mp 186-189° C.

$^1$H NMR (300 MHz, DMSO-$d_6$) δ 8.29 (d, J=8.1 Hz, 1H), 7.60 (d, J=8.1 Hz, 1H), 7.42 (t, J=8.1 Hz, 1H), 7.23 (t, J=8.1 Hz, 1H), 6.56 (bs, 2H), 4.78 (bs, 4H), 3.62 (t, J=5.6 Hz, 2H), 3.31 (s, 3H), 3.11 (t, J=5.6 Hz, 2H), 2.66 (s, 3H), 1.23 (bs, 6H);

MS (APCI) m/z 407 (M+H)$^+$;

Anal. Cacld for $C_{19}H_{26}N_4O_4S$: C, 56.14; H, 6.45: N, 13.78. Found: C, 56.04; H, 6.40; N, 13.96.

Example 39

2-(Methoxymethyl)-1-{2-methyl-2-[2-(methylsulfonyl)ethoxy]propyl}-6,7,8,9-tetrahydro-1H-imidazo[4,5-c]quinolin-4-amine

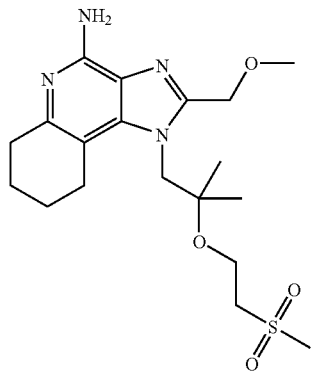

2-(Methoxymethyl)-1-{2-methyl-2-[2-(methylsulfonyl)ethoxy]propyl}-1H-imidazo[4,5-c]quinolin-4-amine (prepared as described in Example 38, 1.40 g, 3.44 mmol) was hydrogenated using the method described in Example 31. After the workup, the white solid was recrystallized from acetonitrile. The crystals were isolated by filtration and dried under vacuum at 65° C. to afford 0.9 g of 2-(methoxymethyl)-1-{2-methyl-2-[2-(methylsulfonyl)ethoxy]propyl}-6,7,8,9-tetrahydro-1H-imidazo[4,5-c]quinolin-4-amine as a white powder, mp 195-197° C.

$^1$H NMR (300 MHz, DMSO-$d_6$) δ 5.81 (bs, 2H), 4.71 (bs, 2H), 4.40 (bs, 2H), 3.62 (t, J=5.6 Hz, 2H), 3.25 (s, 3H), 3.22 (t, J=5.6 Hz, 2H), 2.91 (m, 2H), 2.68 (m, 5H), 1.75 (m, 4H), 1.11 (bs, 6H);

MS (APCI) m/z 411 (M+H)$^+$;

Anal. Cacld for $C_{19}H_{30}N_4O_4S$: C, 55.59; H, 7.37: N, 13.65. Found: C, 55.38; H, 7.48; N, 13.87.

Example 40

2-Ethoxymethyl-1-{2-[2-(methylsulfonyl)ethoxy]-2-methylpropyl}-1H-imidazo[4,5-c][1,5]naphthyridin-4-amine

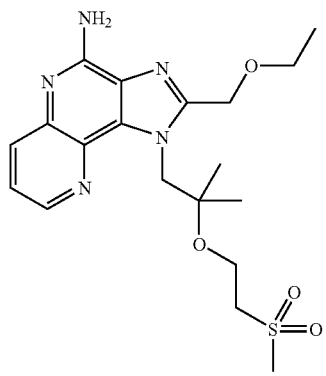

Part A

Under a nitrogen atmosphere 2-amino-1-methylpropan-1-ol (25.5 g, 0.28 mol) was added over a period of 30 minutes to a chilled (15° C.) solution of 4-chloro-3-nitro[1,5]naphthyridine (54.5 g, 0.26 mol) and triethylamine (39.5 g, 0.39 mol) in dichloromethane (1 L). The temperature of the reaction mixture was maintained below about 30° during the addition. After the addition was complete the reaction mixture was stirred at ambient temperature overnight. The resulting precipitate was isolated by filtration, slurried with water, and again isolated by filtration to provide 40.53 g of N-(2-hydroxy-2-methylpropyl)-3-nitro[1,5]naphthyridin-4-amine as a yellow solid.

Part B

N-(2-Hydroxy-2-methylpropyl)-3-nitro[1,5]naphthyridin-4-amine (44.12 g, 0.17 mol), 5% platinum on carbon (4.4 g) and isopropanol (890 mL) were combined in a Parr vessel and placed under hydrogen pressure (35 psi, 2.4×10$^5$ Pa) overnight. The reaction mixture was filtered through a layer of filtering agent. The layer of filtering agent was rinsed well with isopropanol. The filtrate was concentrated under reduced pressure to provide $N^4$-(2-hydroxy-2-methylpropyl)[1,5]naphthyridin-3,4-diamine as a thick oil.

Part C

Under a nitrogen atmosphere, ethoxyacetyl chloride (19.1 g, 0.156 mol) was added over a period of 12 minutes to a mixture of $N^4$-(2-hydroxy-2-methylpropyl)[1,5]naphthyridin-3,4-diamine (28.95 g, 0.125 mol) and pyridine (300 mL). The reaction mixture was stirred at ambient temperature for 4 hours and then heated at reflux for 4 hours. The reaction mixture was allowed to cool to ambient temperature overnight and then concentrated under reduced pressure. The residue was dissolved in 5% aqueous potassium carbonate (200 mL) and then extracted with dichloromethane (200 mL). The extract was filtered to remove some insoluble material, dried over magnesium sulfate, filtered, and then concentrated under high vacuum. The residue was dissolved in dichloromethane (150 mL) and put through a short column of neutral alumina. The eluant was concentrated to provide 31.9 g of 1-(2-ethoxymethyl-1H-imidazo[4,5-c][1,5]naphthyridin-1-yl)-2-methylpropan-2-ol.

Part D 1-(2-Ethoxymethyl-1H-imidazo[4,5-c][1,5]naphthyridin-1-yl)-2-methylpropan-2-ol (29.94 g, 0.083 mol) and dichloromethane (300 mL) were placed in a foil covered flask. 3-Chloroperoxybenzoic acid (about 50%, 28.65 g, 0.083 mol) was added over a period of 50 minutes while maintaining the reaction mixture at 16-20° C. After 40 minutes analysis by thin layer chromatography indicated that the reaction was complete. The reaction mixture was diluted with 5% aqueous potassium carbonate and stirred. The layers were separated. The organic layer was washed with brine, dried over magnesium sulfate, filtered, and then concentrated to provide about 15 g of a yellow paste. This material was stirred with diethyl ether (100 mL) overnight. The resulting solid was isolated by filtration and dried under vacuum to provide 11.84 g of 2-ethoxymethyl-1-(2-hydroxy-2-methylpropyl)-1H-imidazo[4,5-c][1,5]naphthyridine-5N-oxide. The aqueous layer was partially evaporated, combined with additional potassium carbonate, and then extracted with dichloromethane. The extract was dried over magnesium sulfate, filtered, and then concentrated to provide 15.2 g of a dark oil. This material was stirred with diethyl ether (100 mL) overnight. The resulting solid was isolated by filtration and dried under vacuum to provide 11.51 g of 2-ethoxymethyl-1-(2-hydroxy-2-methylpropyl)-1H-imidazo[4,5-c][1,5]naphthyridine-5N-oxide.

Part E

Concentrated ammonium hydroxide (241 mL, 3.7 mol) was added to a solution of 2-ethoxymethyl-1-(2-hydroxy-2-methylpropyl)-1H-imidazo[4,5-c][1,5]naphthyridine-5N-oxide (23.35 g, 0.074 mol) in dichloromethane (300 mL). A solution of p-toluenesulfonyl chloride (15.52 g, 0.081 mol) in dichloromethane (50 mL) was added over a period of 25 minutes with vigorous stirring. The reaction mixture was allowed to stir at ambient temperature overnight. Additional p-toluenesulfonyl chloride (2 g dissolved in 10 mL of dichloromethane) and concentrated ammonium hydroxide (25 mL)

were added and the reaction mixture was stirred for an additional 5 hours. The organic phase was separated, then washed with a solution of potassium carbonate (16 g) in water (300 mL), dried over magnesium sulfate, filtered, and concentrated under reduced pressure to provide 30.17 g of a semisolid residue. The residue was combined with acetonitrile (300 mL), heated to reflux with stirring, and then allowed to cool to ambient temperature with stirring. The resulting solid was isolated by filtration and dried under vacuum at 75° C. to provide 14.4 g of a solid. This material was recrystallized from ethyl acetate (17.5 mL/g) and then dried under vacuum at 75° C. for 22 hours to provide 12.29 g of 1-(4-amino-2-ethoxymethyl-1H-imidazo[4,5-c][1,5]naphthyridin-1-yl)-2-methylpropan-2-ol as an off white solid, m.p 157-159° C. Anal. Calcd for $C_{16}H_{21}N_5O_2$: % C, 60.94; % H, 6.71; % N, 22.21. Found: % C, 61.06; % H, 6.67; % N, 22.37.

Part F

A suspension of 1-(4-amino-2-ethoxymethyl-1H-imidazo[4,5-c][1,5]naphthyridin-1-yl)-2-methylpropan-2-ol (2.87 g, 9.10 mmol), di-tert-butyl di-carbonate (5 g, 22.75 mmol), triethylamine (2.3 g, 22.75 mmol), 4-(dimethylamino)pyridine (111 mg, 0.91 mmol) and acetonitrile (91 mL) was heated to reflux at which time a solution was obtained. The solution was heated at reflux for 2 hours and then concentrated under reduced pressure. The resulting oil was partitioned between dichloromethane (200 mL) and saturated aqueous ammonium chloride (100 mL). The organic layer was separated, washed with saturated aqueous sodium bicarbonate (100 mL), dried over sodium sulfate, filtered, and then concentrated under reduced pressure to provide an orange oil. The oil was purified by column chromatography (silica gel eluted with 7/3 ethyl acetate/hexanes) to provide 4 g of N,N-(bis tert-butoxycarbonyl)-1-(4-amino-2-ethoxymethyl-1H-imidazo[4,5-c][1,5]naphthyridin-1-yl)-2-methylpropan-2-ol as a peach oil which solidified under vacuum.

Part G

Under a nitrogen atmosphere, sodium hydride 31 mg, 60% dispersion in mineral oil) was added to a solution of N,N-(bis tert-butoxycarbonyl)-1-(4-amino-2-ethoxymethyl-1H-imidazo[4,5-c][1,5]naphthyridin-1-yl)-2-methylpropan-2-ol (4 g, 7.7 mmol) in anhydrous tetrahydrofuran (31 mL). After 5 minutes methyl vinyl sulfone (1.6 g, 15.5 mmol) was added and the reaction mixture was stirred at ambient temperature for 30 minutes. Two additional portions of sodium hydride (60 mg each) were added sequentially while monitoring the progress of the reaction by thin layer chromatography. The reaction mixture was quenched with water (a few drops) and then concentrated under reduced pressure. The resulting oil was purified by column chromatography (silica gel eluted with 6/4 ethyl acetate/hexanes) to provide 2.1 g of starting material (N,N-(bis tert-butoxycarbonyl)-1-(4-amino-2-ethoxymethyl-1H-imidazo[4,5-c][1,5]naphthyridin-1-yl)-2-methylpropan-2-ol) and 1.6 g of a mixture of the desired product (N,N-(bis tert-butoxycarbonyl)-2-ethoxymethyl-1-{2-[2-(methylsulfonyl)ethoxy]-2-methylpropyl}-1H-imidazo[4,5-c][1,5]naphthyridin-4-amine) and mono-BOC starting material (N-tert-butoxycarbonyl-1-(4-amino-2-ethoxymethyl-1H-imidazo[4,5-c][1,5]naphthyridin-1-yl)-2-methylpropan-2-ol).

Part H

A solution of the mixture from part G (1.6 g), hydrochloric acid (3.2 mL of a 4M solution in dioxane), and methanol (5 mL) was stirred at ambient temperature for 1 hour and then heated to reflux and maintained at that temperature for 30 minutes. The reaction mixture was cooled and then concentrated under reduced pressure. The resulting oil was combined with water (20 mL) and a precipitate formed. The suspension was adjusted to pH 12 by the addition of aqueous sodium hydroxide (50%) and stirred for 30 minutes. The solid was isolated by filtration and rinsed with water to provide 0.5 g of a white powder. Analysis by $^1$H NMR showed that this material was about a 1:1 mixture of the desired product and 1-(4-amino-2-ethoxymethyl-1H-imidazo[4,5-c][1,5]naphthyridin-1-yl)-2-methylpropan-2-ol. This mixture was separated by HPLC purification over multiple injections. HPLC conditions: Solvent A: 0.5% formic acid/99.5% acetonitrile; Solvent B: 0.5% formic acid/99.5% water. Gradient: 5% solvent B to 15% solvent B over 7 minutes, then 15% solvent B to 95% solvent B in 1 min, held at 95% solvent B for 1 minute, return to initial conditions over 1 minute. The clean fractions were combined and concentrated under reduced pressure to provide about 0.15 g of an oil. The oil was dissolved in water (3 mL). The solution was adjusted to pH 12 by the addition of aqueous sodium hydroxide (50%). A white precipitate formed. The solid was stirred for 1 hour, isolated by filtration, washed with water, and then dried under vacuum at 65° C. for 18 hours to provide 120 mg of 2-ethoxymethyl-1-{2-[2-(methylsulfonyl)ethoxy]-2-methylpropyl}-1H-imidazo[4,5-c][1,5]naphthyridin-4-amine as a white powder, mp 189-191° C. Anal. Calcd for $C_{19}H_{27}N_5O_4S \cdot 0.25H_2O$: % C, 53.57; % H, 6.51; % N, 16.44. Found: % C, 53.24; % H, 6.83; % N, 16.27.

Examples 41~48

The examples in the table below can be prepared by treating the indicated starting material with boron tribromide. The reaction can be carried out by adding a solution of boron tribromide (2.5 equivalents of 1 M in dichloromethane) to a suspension or solution of the staring material (1 equivalent) in dichloromethane at 0° C. The reaction mixture is maintained at 0° C. until complete and then quenched with methanol. The product can be isolated using conventional methods.

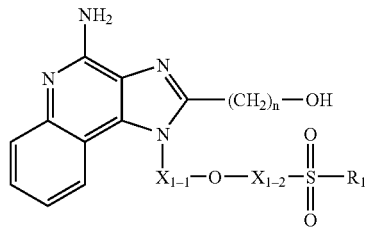

| Example | Starting Material | n | $X_{1-1}$ | $X_{1-2}$ | $R_1$ |
|---|---|---|---|---|---|
| 41 | Example 6 | 1 | —$CH_2CH_2$— | —$CH_2CH_2$— | —$CH_3$ |
| 42 | Example 7 | 2 | —$CH_2CH_2$— | —$CH_2CH_2$— | —$CH_3$ |
| 43 | Example 8 | 1 | —$CH_2C(CH_3)_2$— | —$CH_2CH_2$— | phenyl |
| 44 | Example 9 | 1 | —$CH_2C(CH_3)_2$— | —$CH_2CH_2$— | —$CH_3$ |
| 45 | Example 23 | 1 | —$CH_2$-cyc$(CH_2)_5$— | —$CH_2CH_2$— | —$CH_3$ |
| 46 | Example 24 | 1 | —$CH_2$-cyc$(CH_2)_6$— | —$CH_2CH_2$— | —$CH_3$ |
| 47 | Example 26 | 1 | —$CH_2$-cyc$(CH_2)_4$— | —$CH_2CH_2$— | —$CH_3$ |
| 48 | Example 34 | 1 | —$CH_2$-cyc$(CH_2)_3$— | —$CH_2CH_2$— | —$CH_3$ |

Examples 49-50

Examples in the table below can be prepared using the method described for Examples 41-48.

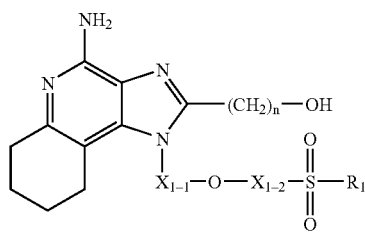

| Example | Starting Material | n | $X_{1-1}$ | $X_{1-2}$ | $R_1$ |
|---|---|---|---|---|---|
| 49 | Example 28 | 1 | —CH$_2$C(CH$_3$)$_2$— | —CH$_2$CH$_2$— | —CH$_3$ |
| 50 | Example 27 | 1 | —CH$_2$-cyc(CH$_2$)$_4$— | —CH$_2$CH$_2$— | —CH$_3$ |

Exemplary Compounds

Certain exemplary compounds have the following Formula (Ia-6) wherein $X_{1-1}$, $X_{1-2}$, $R_1$, and $R_2$ are defined in the table below, wherein each line of the table represents a specific compound.

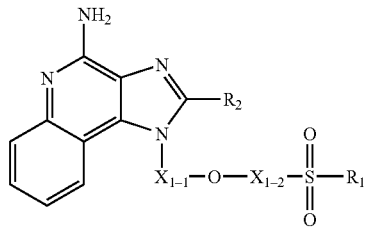

IIa-6

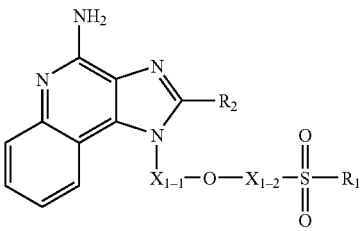

IIa-6

| $X_{1-1}$ | $X_{1-2}$ | $R_1$ | $R_2$ |
|---|---|---|---|
| ethylene | ethylene | methyl | methyl |
| ethylene | ethylene | methyl | ethyl |
| ethylene | ethylene | methyl | propyl |
| ethylene | ethylene | methyl | butyl |
| ethylene | ethylene | methyl | ethoxymethyl |
| ethylene | ethylene | methyl | 2-methoxyethyl |
| ethylene | ethylene | ethyl | methyl |
| ethylene | ethylene | ethyl | ethyl |
| ethylene | ethylene | ethyl | propyl |
| ethylene | ethylene | ethyl | butyl |
| ethylene | ethylene | ethyl | ethoxymethyl |
| ethylene | ethylene | ethyl | 2-methoxyethyl |
| ethylene | ethylene | propyl | methyl |
| ethylene | ethylene | propyl | ethyl |
| ethylene | ethylene | propyl | propyl |
| ethylene | ethylene | propyl | butyl |
| ethylene | ethylene | propyl | ethoxymethyl |
| ethylene | ethylene | propyl | 2-methoxyethyl |
| ethylene | ethylene | 1-methyethyl | methyl |
| ethylene | ethylene | 1-methyethyl | ethyl |
| ethylene | ethylene | 1-methyethyl | propyl |
| ethylene | ethylene | 1-methyethyl | butyl |
| ethylene | ethylene | 1-methyethyl | ethoxymethyl |
| ethylene | ethylene | 1-methyethyl | 2-methoxyethyl |
| ethylene | propylene | methyl | methyl |
| ethylene | propylene | methyl | ethyl |
| ethylene | propylene | methyl | propyl |
| ethylene | propylene | methyl | butyl |
| ethylene | propylene | methyl | ethoxymethyl |
| ethylene | propylene | methyl | 2-methoxyethyl |
| ethylene | propylene | ethyl | methyl |
| ethylene | propylene | ethyl | ethyl |
| ethylene | propylene | ethyl | propyl |
| ethylene | propylene | ethyl | butyl |
| ethylene | propylene | ethyl | ethoxymethyl |
| ethylene | propylene | ethyl | 2-methoxyethyl |
| ethylene | propylene | propyl | methyl |
| ethylene | propylene | propyl | ethyl |
| ethylene | propylene | propyl | propyl |
| ethylene | propylene | propyl | butyl |
| ethylene | propylene | propyl | ethoxymethyl |
| ethylene | propylene | propyl | 2-methoxyethyl |
| ethylene | propylene | 1-methyethyl | methyl |
| ethylene | propylene | 1-methyethyl | ethyl |
| ethylene | propylene | 1-methyethyl | propyl |
| ethylene | propylene | 1-methyethyl | butyl |
| ethylene | propylene | 1-methyethyl | ethoxymethyl |
| ethylene | propylene | 1-methyethyl | 2-methoxyethyl |
| propylene | ethylene | methyl | methyl |
| propylene | ethylene | methyl | ethyl |
| propylene | ethylene | methyl | propyl |
| propylene | ethylene | methyl | butyl |
| propylene | ethylene | methyl | ethoxymethyl |
| propylene | ethylene | methyl | 2-methoxyethyl |
| propylene | ethylene | ethyl | methyl |
| propylene | ethylene | ethyl | ethyl |
| propylene | ethylene | ethyl | propyl |
| propylene | ethylene | ethyl | butyl |
| propylene | ethylene | ethyl | ethoxymethyl |
| propylene | ethylene | ethyl | 2-methoxyethyl |
| propylene | ethylene | propyl | methyl |
| propylene | ethylene | propyl | ethyl |
| propylene | ethylene | propyl | propyl |
| propylene | ethylene | propyl | butyl |
| propylene | ethylene | propyl | ethoxymethyl |
| propylene | ethylene | propyl | 2-methoxyethyl |
| propylene | ethylene | 1-methyethyl | methyl |
| propylene | ethylene | 1-methyethyl | ethyl |
| propylene | ethylene | 1-methyethyl | propyl |
| propylene | ethylene | 1-methyethyl | butyl |
| propylene | ethylene | 1-methyethyl | ethoxymethyl |
| propylene | ethylene | 1-methyethyl | 2-methoxyethyl |
| propylene | propylene | methyl | methyl |
| propylene | propylene | methyl | ethyl |
| propylene | propylene | methyl | propyl |
| propylene | propylene | methyl | butyl |
| propylene | propylene | methyl | ethoxymethyl |
| propylene | propylene | methyl | 2-methoxyethyl |
| propylene | propylene | ethyl | methyl |
| propylene | propylene | ethyl | ethyl |
| propylene | propylene | ethyl | propyl |
| propylene | propylene | ethyl | butyl |
| propylene | propylene | ethyl | ethoxymethyl |
| propylene | propylene | ethyl | 2-methoxyethyl |
| propylene | propylene | propyl | methyl |
| propylene | propylene | propyl | ethyl |
| propylene | propylene | propyl | propyl |
| propylene | propylene | propyl | butyl |
| propylene | propylene | propyl | ethoxymethyl |
| propylene | propylene | propyl | 2-methoxyethyl |
| propylene | propylene | 1-methyethyl | methyl |
| propylene | propylene | 1-methyethyl | ethyl |
| propylene | propylene | 1-methyethyl | propyl |
| propylene | propylene | 1-methyethyl | butyl |
| propylene | propylene | 1-methyethyl | ethoxymethyl |
| propylene | propylene | 1-methyethyl | 2-methoxyethyl |

Certain exemplary compounds, including some of those described above in the Examples, have the following Formulas (IIa-6, IIIa-4, IVa-2, and XLII) and the following substituents ($X_{1-1}$, $X_{1-2}$, $R_1$, and $R_2$) wherein each line of the table is matched with each Formula to represent a specific embodiment of the invention and wherein

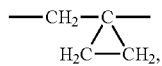

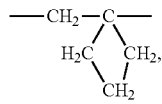

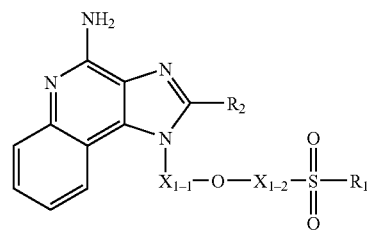

IIa-6

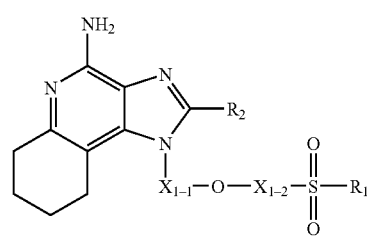

IIIa-4

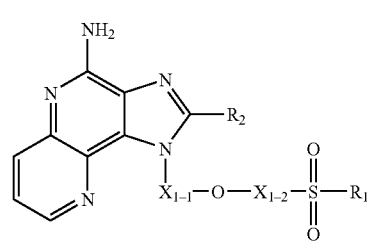

IVa-2

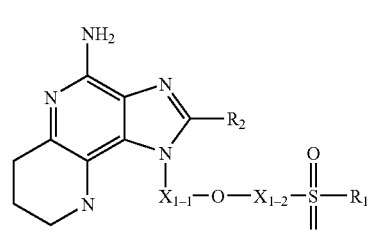

XLII

| $X_{1-1}$ | $X_{1-2}$ | $R_1$ | $R_2$ |
|---|---|---|---|
| —CH$_2$CH$_2$— | —CH$_2$CH$_2$— | —CH$_3$ | H |
| —CH$_2$CH$_2$— | —CH$_2$CH$_2$— | —CH$_3$ | —CH$_3$ |
| —CH$_2$CH$_2$— | —CH$_2$CH$_2$— | —CH$_3$ | —CH$_2$CH$_3$ |
| —CH$_2$CH$_2$— | —CH$_2$CH$_2$— | —CH$_3$ | —(CH$_2$)$_2$CH$_3$ |
| —CH$_2$CH$_2$— | —CH$_2$CH$_2$— | —CH$_3$ | —(CH$_2$)$_3$CH$_3$ |
| —CH$_2$CH$_2$— | —CH$_2$CH$_2$— | —CH$_3$ | —CH$_2$OCH$_2$CH$_3$ |
| —CH$_2$CH$_2$— | —CH$_2$CH$_2$— | —CH$_3$ | —(CH$_2$)$_2$OCH$_3$ |
| —CH$_2$CH$_2$— | —CH$_2$CH$_2$— | —CH$_3$ | —CH$_2$OH |

-continued

—CH₂—cyc(CH₂)₃— is

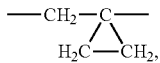

and —CH₂—cyc(CH₂)₄— is

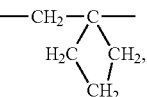

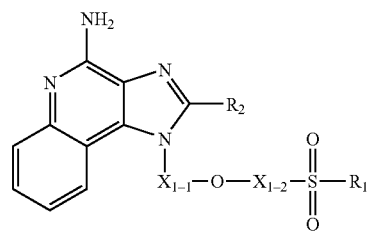

IIa-6

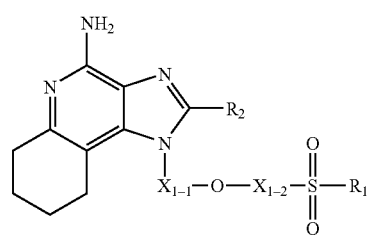

IIIa-4

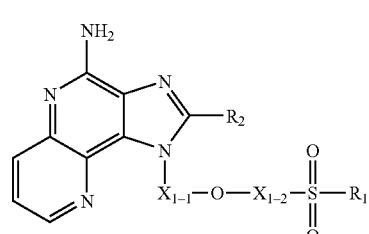

IVa-2

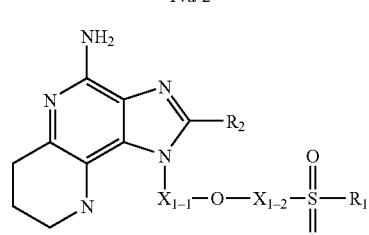

XLII

| X₁₋₁ | X₁₋₂ | R₁ | R₂ |
|---|---|---|---|
| —CH₂CH₂— | —CH₂CH₂— | —CH₃ | —(CH₂)₂OH |
| —CH₂CH₂— | —CH₂CH₂— | —CH₂CH₃ | H |
| —CH₂CH₂— | —CH₂CH₂— | —CH₂CH₃ | —CH₃ |
| —CH₂CH₂— | —CH₂CH₂— | —CH₂CH₃ | —CH₂CH₃ |
| —CH₂CH₂— | —CH₂CH₂— | —CH₂CH₃ | —(CH₂)₂CH₃ |
| —CH₂CH₂— | —CH₂CH₂— | —CH₂CH₃ | —(CH₂)₃CH₃ |
| —CH₂CH₂— | —CH₂CH₂— | —CH₂CH₃ | —CH₂OCH₂CH₃ |
| —CH₂CH₂— | —CH₂CH₂— | —CH₂CH₃ | —(CH₂)₂OCH₃ |
| —CH₂CH₂— | —CH₂CH₂— | —CH₂CH₃ | —CH₂OH |
| —CH₂CH₂— | —CH₂CH₂— | —CH₂CH₃ | —(CH₂)₂OH |
| —CH₂CH₂— | —CH₂CH₂— | —(CH₂)₂CH₃ | H |
| —CH₂CH₂— | —CH₂CH₂— | —(CH₂)₂CH₃ | —CH₃ |
| —CH₂CH₂— | —CH₂CH₂— | —(CH₂)₂CH₃ | —CH₂CH₃ |

-continued

—CH$_2$—cyc(CH$_2$)$_3$— is

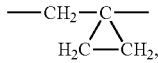

and —CH$_2$—cyc(CH$_2$)$_4$— is

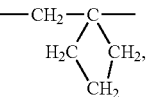

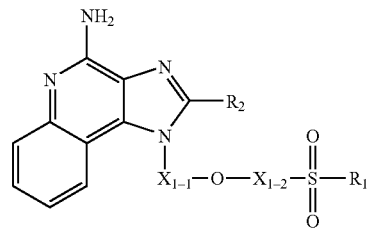

IIa-6

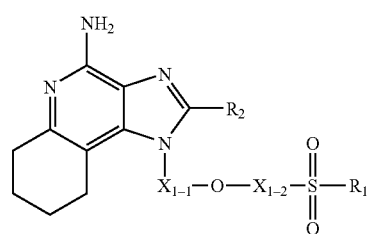

IIIa-4

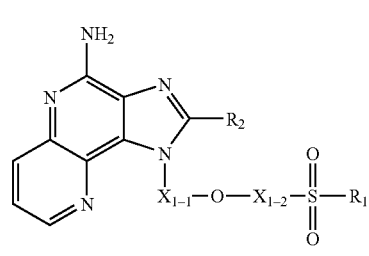

IVa-2

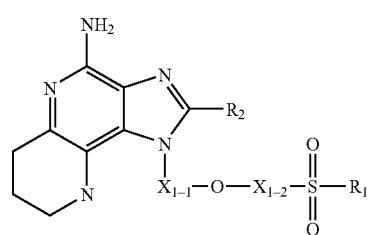

XLII

| $X_{1-1}$ | $X_{1-2}$ | $R_1$ | $R_2$ |
|---|---|---|---|
| —CH$_2$CH$_2$— | —CH$_2$CH$_2$— | —(CH$_2$)$_2$CH$_3$ | —(CH$_2$)$_2$CH$_3$ |
| —CH$_2$CH$_2$— | —CH$_2$CH$_2$— | —(CH$_2$)$_2$CH$_3$ | —(CH$_2$)$_3$CH$_3$ |
| —CH$_2$CH$_2$— | —CH$_2$CH$_2$— | —(CH$_2$)$_2$CH$_3$ | —CH$_2$OCH$_2$CH$_3$ |
| —CH$_2$CH$_2$— | —CH$_2$CH$_2$— | —(CH$_2$)$_2$CH$_3$ | —(CH$_2$)$_2$OCH$_3$ |
| —CH$_2$CH$_2$— | —CH$_2$CH$_2$— | —(CH$_2$)$_2$CH$_3$ | —CH$_2$OH |
| —CH$_2$CH$_2$— | —CH$_2$CH$_2$— | —(CH$_2$)$_2$CH$_3$ | —(CH$_2$)$_2$OH |
| —CH$_2$CH$_2$— | —CH$_2$CH$_2$— | —CH(CH$_3$)$_2$ | H |
| —CH$_2$CH$_2$— | —CH$_2$CH$_2$— | —CH(CH$_3$)$_2$ | —CH$_3$ |
| —CH$_2$CH$_2$— | —CH$_2$CH$_2$— | —CH(CH$_3$)$_2$ | —CH$_2$CH$_3$ |
| —CH$_2$CH$_2$— | —CH$_2$CH$_2$— | —CH(CH$_3$)$_2$ | —(CH$_2$)$_2$CH$_3$ |
| —CH$_2$CH$_2$— | —CH$_2$CH$_2$— | —CH(CH$_3$)$_2$ | —(CH$_2$)$_3$CH$_3$ |
| —CH$_2$CH$_2$— | —CH$_2$CH$_2$— | —CH(CH$_3$)$_2$ | —CH$_2$OCH$_2$CH$_3$ |
| —CH$_2$CH$_2$— | —CH$_2$CH$_2$— | —CH(CH$_3$)$_2$ | —(CH$_2$)$_2$OCH$_3$ |

-continued

—CH₂—cyc(CH₂)₃— is

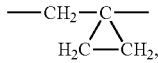

and —CH₂—cyc(CH₂)₄— is

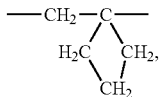

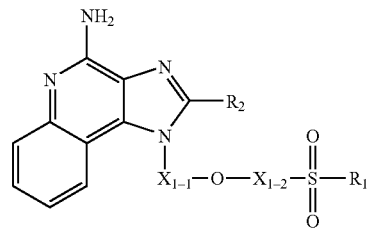

IIa-6

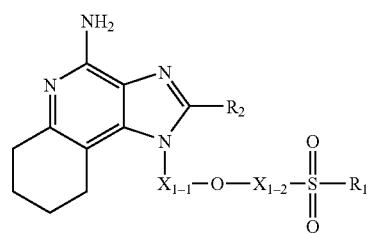

IIIa-4

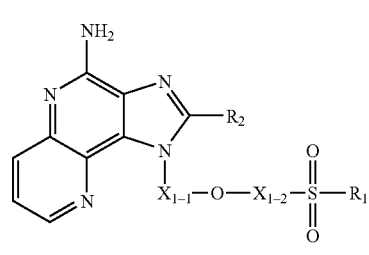

IVa-2

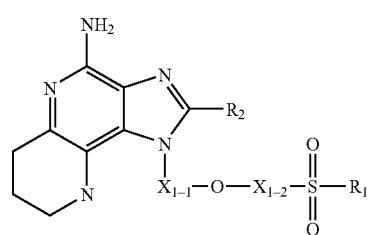

XLII

| $X_{1\text{-}1}$ | $X_{1\text{-}2}$ | $R_1$ | $R_2$ |
|---|---|---|---|
| —CH₂CH₂— | —CH₂CH₂— | —CH(CH₃)₂ | —CH₂OH |
| —CH₂CH₂— | —CH₂CH₂— | —CH(CH₃)₂ | —(CH₂)₂OH |
| —CH₂CH₂— | —CH₂CH₂CH₂— | —CH₃ | H |
| —CH₂CH₂— | —CH₂CH₂CH₂— | —CH₃ | —CH₃ |
| —CH₂CH₂— | —CH₂CH₂CH₂— | —CH₃ | —CH₂CH₃ |
| —CH₂CH₂— | —CH₂CH₂CH₂— | —CH₃ | —(CH₂)₂CH₃ |
| —CH₂CH₂— | —CH₂CH₂CH₂— | —CH₃ | —(CH₂)₃CH₃ |
| —CH₂CH₂— | —CH₂CH₂CH₂— | —CH₃ | —CH₂OCH₂CH₃ |
| —CH₂CH₂— | —CH₂CH₂CH₂— | —CH₃ | —(CH₂)₂OCH₃ |
| —CH₂CH₂— | —CH₂CH₂CH₂— | —CH₃ | —CH₂OH |
| —CH₂CH₂— | —CH₂CH₂CH₂— | —CH₃ | —(CH₂)₂OH |
| —CH₂CH₂— | —CH₂CH₂CH₂— | —CH₂CH₃ | H |
| —CH₂CH₂— | —CH₂CH₂CH₂— | —CH₂CH₃ | —CH₃ |

-continued

—CH₂—cyc(CH₂)₃— is

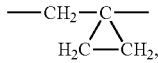

and —CH₂—cyc(CH₂)₄— is

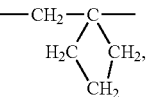

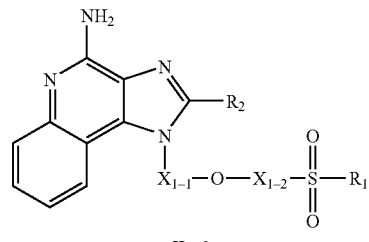

IIa-6

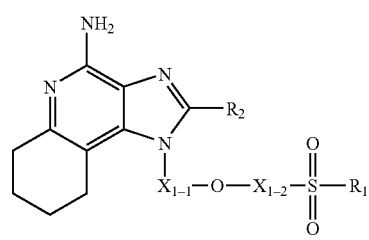

IIIa-4

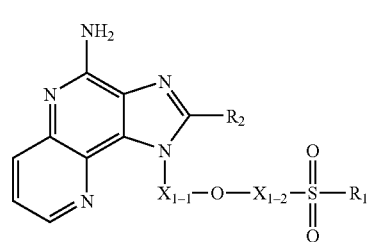

IVa-2

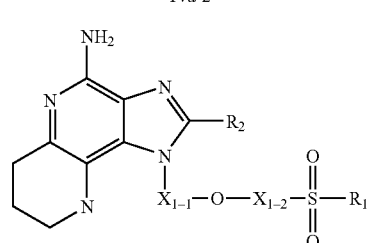

XLII

| X₁₋₁ | X₁₋₂ | R₁ | R₂ |
|---|---|---|---|
| —CH₂CH₂— | —CH₂CH₂CH₂— | —CH₂CH₃ | —CH₂CH₃ |
| —CH₂CH₂— | —CH₂CH₂CH₂— | —CH₂CH₃ | —(CH₂)₂CH₃ |
| —CH₂CH₂— | —CH₂CH₂CH₂— | —CH₂CH₃ | —(CH₂)₃CH₃ |
| —CH₂CH₂— | —CH₂CH₂CH₂— | —CH₂CH₃ | —CH₂OCH₂CH₃ |
| —CH₂CH₂— | —CH₂CH₂CH₂— | —CH₂CH₃ | —(CH₂)₂OCH₃ |
| —CH₂CH₂— | —CH₂CH₂CH₂— | —CH₂CH₃ | —CH₂OH |
| —CH₂CH₂— | —CH₂CH₂CH₂— | —CH₂CH₃ | —(CH₂)₂OH |
| —CH₂CH₂— | —CH₂CH₂CH₂— | —(CH₂)₂CH₃ | H |
| —CH₂CH₂— | —CH₂CH₂CH₂— | —(CH₂)₂CH₃ | —CH₃ |
| —CH₂CH₂— | —CH₂CH₂CH₂— | —(CH₂)₂CH₃ | —CH₂CH₃ |
| —CH₂CH₂— | —CH₂CH₂CH₂— | —(CH₂)₂CH₃ | —(CH₂)₂CH₃ |
| —CH₂CH₂— | —CH₂CH₂CH₂— | —(CH₂)₂CH₃ | —(CH₂)₃CH₃ |
| —CH₂CH₂— | —CH₂CH₂CH₂— | —(CH₂)₂CH₃ | —CH₂OCH₂CH₃ |

-continued

—CH₂—cyc(CH₂)₃— is

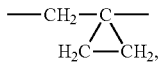

and —CH₂—cyc(CH₂)₄— is

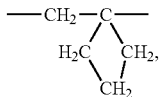

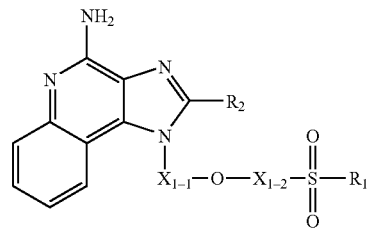

IIa-6

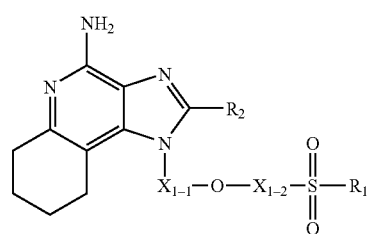

IIIa-4

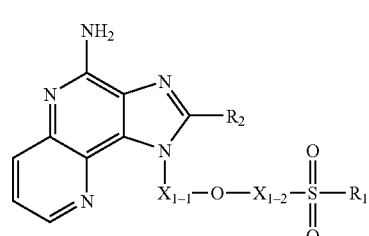

IVa-2

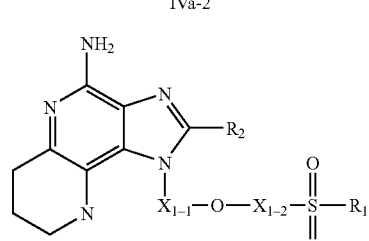

XLII

| $X_{1-1}$ | $X_{1-2}$ | $R_1$ | $R_2$ |
|---|---|---|---|
| —CH₂CH₂— | —CH₂CH₂CH₂— | —(CH₂)₂CH₃ | —(CH₂)₂OCH₃ |
| —CH₂CH₂— | —CH₂CH₂CH₂— | —(CH₂)₂CH₃ | —CH₂OH |
| —CH₂CH₂— | —CH₂CH₂CH₂— | —(CH₂)₂CH₃ | —(CH₂)₂OH |
| —CH₂CH₂— | —CH₂CH₂CH₂— | —CH(CH₃)₂ | H |
| —CH₂CH₂— | —CH₂CH₂CH₂— | —CH(CH₃)₂ | —CH₃ |
| —CH₂CH₂— | —CH₂CH₂CH₂— | —CH(CH₃)₂ | —CH₂CH₃ |
| —CH₂CH₂— | —CH₂CH₂CH₂— | —CH(CH₃)₂ | —(CH₂)₂CH₃ |
| —CH₂CH₂— | —CH₂CH₂CH₂— | —CH(CH₃)₂ | —(CH₂)₃CH₃ |
| —CH₂CH₂— | —CH₂CH₂CH₂— | —CH(CH₃)₂ | —CH₂OCH₂CH₃ |
| —CH₂CH₂— | —CH₂CH₂CH₂— | —CH(CH₃)₂ | —(CH₂)₂OCH₃ |
| —CH₂CH₂— | —CH₂CH₂CH₂— | —CH(CH₃)₂ | —CH₂OH |
| —CH₂CH₂— | —CH₂CH₂CH₂— | —CH(CH₃)₂ | —(CH₂)₂OH |
| —CH₂CH₂CH₂— | —CH₂CH₂— | —CH₃ | H |

-continued

—CH₂—cyc(CH₂)₃— is

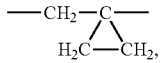

and —CH₂—cyc(CH₂)₄— is

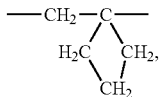

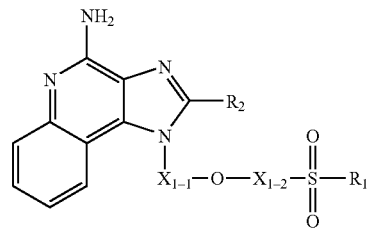

IIa-6

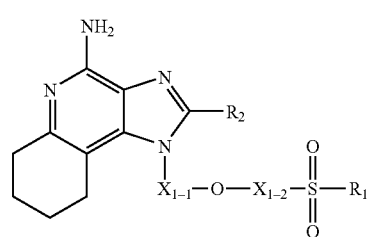

IIIa-4

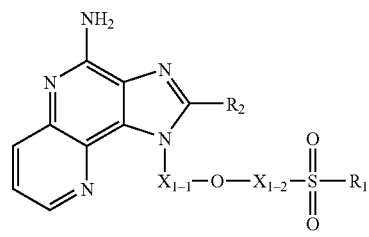

IVa-2

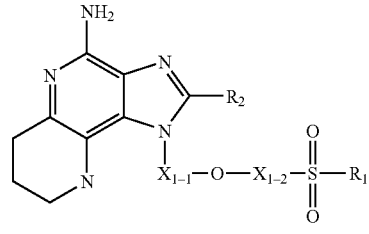

XLII

| $X_{1-1}$ | $X_{1-2}$ | $R_1$ | $R_2$ |
|---|---|---|---|
| —CH₂CH₂CH₂— | —CH₂CH₂— | —CH₃ | —CH₃ |
| —CH₂CH₂CH₂— | —CH₂CH₂— | —CH₃ | —CH₂CH₃ |
| —CH₂CH₂CH₂— | —CH₂CH₂— | —CH₃ | —(CH₂)₂CH₃ |
| —CH₂CH₂CH₂— | —CH₂CH₂— | —CH₃ | —(CH₂)₃CH₃ |
| —CH₂CH₂CH₂— | —CH₂CH₂— | —CH₃ | —CH₂OCH₂CH₃ |
| —CH₂CH₂CH₂— | —CH₂CH₂— | —CH₃ | —(CH₂)₂OCH₃ |
| —CH₂CH₂CH₂— | —CH₂CH₂— | —CH₃ | —CH₂OH |
| —CH₂CH₂CH₂— | —CH₂CH₂— | —CH₃ | —(CH₂)₂OH |
| —CH₂CH₂CH₂— | —CH₂CH₂— | —CH₂CH₃ | H |
| —CH₂CH₂CH₂— | —CH₂CH₂— | —CH₂CH₃ | —CH₃ |
| —CH₂CH₂CH₂— | —CH₂CH₂— | —CH₂CH₃ | —CH₂CH₃ |
| —CH₂CH₂CH₂— | —CH₂CH₂— | —CH₂CH₃ | —(CH₂)₂CH₃ |
| —CH₂CH₂CH₂— | —CH₂CH₂— | —CH₂CH₃ | —(CH₂)₃CH₃ |

-continued

—CH₂—cyc(CH₂)₃— is

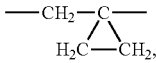

and —CH₂—cyc(CH₂)₄— is

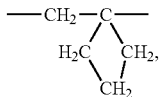

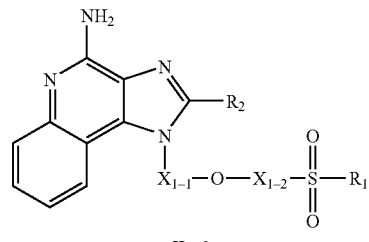

IIa-6

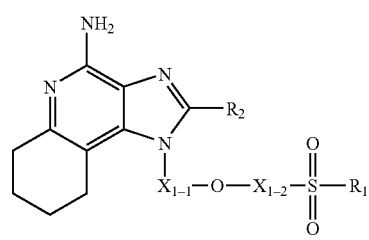

IIIa-4

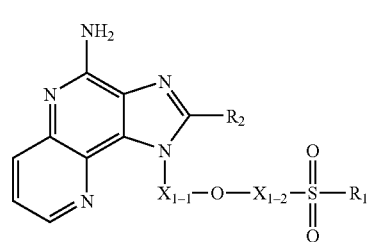

IVa-2

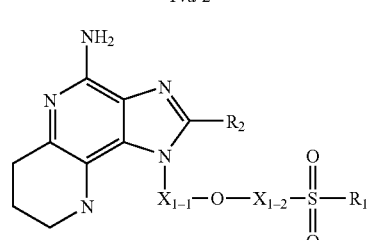

XLII

| $X_{1-1}$ | $X_{1-2}$ | $R_1$ | $R_2$ |
|---|---|---|---|
| —CH₂CH₂CH₂— | —CH₂CH₂— | —CH₂CH₃ | —CH₂OCH₂CH₃ |
| —CH₂CH₂CH₂— | —CH₂CH₂— | —CH₂CH₃ | —(CH₂)₂OCH₃ |
| —CH₂CH₂CH₂— | —CH₂CH₂— | —CH₂CH₃ | —CH₂OH |
| —CH₂CH₂CH₂— | —CH₂CH₂— | —CH₂CH₃ | —(CH₂)₂OH |
| —CH₂CH₂CH₂— | —CH₂CH₂— | —(CH₂)₂CH₃ | H |
| —CH₂CH₂CH₂— | —CH₂CH₂— | —(CH₂)₂CH₃ | —CH₃ |
| —CH₂CH₂CH₂— | —CH₂CH₂— | —(CH₂)₂CH₃ | —CH₂CH₃ |
| —CH₂CH₂CH₂— | —CH₂CH₂— | —(CH₂)₂CH₃ | —(CH₂)₂CH₃ |
| —CH₂CH₂CH₂— | —CH₂CH₂— | —(CH₂)₂CH₃ | —(CH₂)₃CH₃ |
| —CH₂CH₂CH₂— | —CH₂CH₂— | —(CH₂)₂CH₃ | —CH₂OCH₂CH₃ |
| —CH₂CH₂CH₂— | —CH₂CH₂— | —(CH₂)₂CH₃ | —(CH₂)₂OCH₃ |
| —CH₂CH₂CH₂— | —CH₂CH₂— | —(CH₂)₂CH₃ | —CH₂OH |
| —CH₂CH₂CH₂— | —CH₂CH₂— | —(CH₂)₂CH₃ | —(CH₂)₂OH |

-continued

—CH₂—cyc(CH₂)₃— is

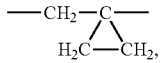

and —CH₂—cyc(CH₂)₄— is

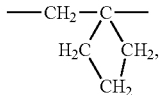

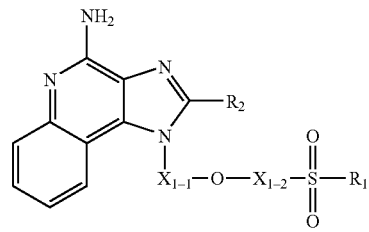

IIa-6

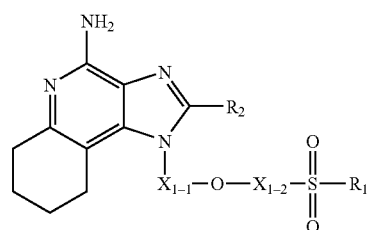

IIIa-4

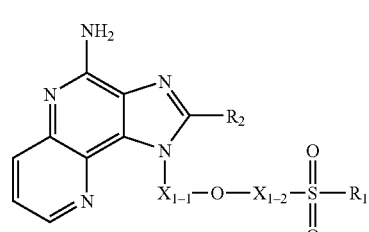

IVa-2

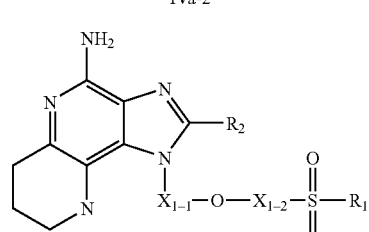

XLII

| X₁₋₁ | X₁₋₂ | R₁ | R₂ |
|---|---|---|---|
| —CH₂CH₂CH₂— | —CH₂CH₂— | —CH(CH₃)₂ | H |
| —CH₂CH₂CH₂— | —CH₂CH₂— | —CH(CH₃)₂ | —CH₃ |
| —CH₂CH₂CH₂— | —CH₂CH₂— | —CH(CH₃)₂ | —CH₂CH₃ |
| —CH₂CH₂CH₂— | —CH₂CH₂— | —CH(CH₃)₂ | —(CH₂)₂CH₃ |
| —CH₂CH₂CH₂— | —CH₂CH₂— | —CH(CH₃)₂ | —(CH₂)₃CH₃ |
| —CH₂CH₂CH₂— | —CH₂CH₂— | —CH(CH₃)₂ | —CH₂OCH₂CH₃ |
| —CH₂CH₂CH₂— | —CH₂CH₂— | —CH(CH₃)₂ | —(CH₂)₂OCH₃ |
| —CH₂CH₂CH₂— | —CH₂CH₂— | —CH(CH₃)₂ | —CH₂OH |
| —CH₂CH₂CH₂— | —CH₂CH₂— | —CH(CH₃)₂ | —(CH₂)₂OH |
| —CH₂CH₂CH₂— | —CH₂CH₂CH₂— | —CH₃ | H |
| —CH₂CH₂CH₂— | —CH₂CH₂CH₂— | —CH₃ | —CH₃ |
| —CH₂CH₂CH₂— | —CH₂CH₂CH₂— | —CH₃ | —CH₂CH₃ |
| —CH₂CH₂CH₂— | —CH₂CH₂CH₂— | —CH₃ | —(CH₂)₂CH₃ |

-continued

—CH₂—cyc(CH₂)₃— is

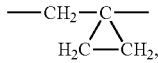

and —CH₂—cyc(CH₂)₄— is

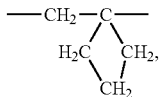

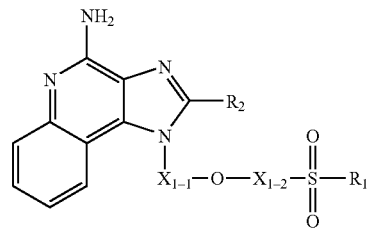

IIa-6

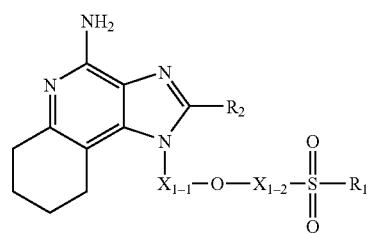

IIIa-4

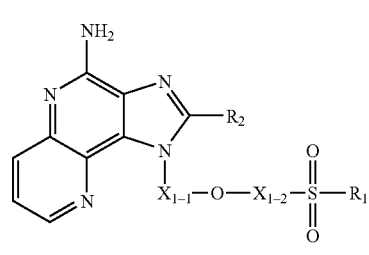

IVa-2

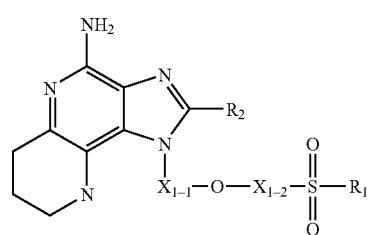

XLII

| $X_{1-1}$ | $X_{1-2}$ | $R_1$ | $R_2$ |
|---|---|---|---|
| —CH₂CH₂CH₂— | —CH₂CH₂CH₂— | —CH₃ | —(CH₂)₃CH₃ |
| —CH₂CH₂CH₂— | —CH₂CH₂CH₂— | —CH₃ | —CH₂OCH₂CH₃ |
| —CH₂CH₂CH₂— | —CH₂CH₂CH₂— | —CH₃ | —(CH₂)₂OCH₃ |
| —CH₂CH₂CH₂— | —CH₂CH₂CH₂— | —CH₃ | —CH₂OH |
| —CH₂CH₂CH₂— | —CH₂CH₂CH₂— | —CH₃ | —(CH₂)₂OH |
| —CH₂CH₂CH₂— | —CH₂CH₂CH₂— | —CH₂CH₃ | H |
| —CH₂CH₂CH₂— | —CH₂CH₂CH₂— | —CH₂CH₃ | —CH₃ |
| —CH₂CH₂CH₂— | —CH₂CH₂CH₂— | —CH₂CH₃ | —CH₂CH₃ |
| —CH₂CH₂CH₂— | —CH₂CH₂CH₂— | —CH₂CH₃ | —(CH₂)₂CH₃ |
| —CH₂CH₂CH₂— | —CH₂CH₂CH₂— | —CH₂CH₃ | —(CH₂)₃CH₃ |
| —CH₂CH₂CH₂— | —CH₂CH₂CH₂— | —CH₂CH₃ | —CH₂OCH₂CH₃ |
| —CH₂CH₂CH₂— | —CH₂CH₂CH₂— | —CH₂CH₃ | —(CH₂)₂OCH₃ |
| —CH₂CH₂CH₂— | —CH₂CH₂CH₂— | —CH₂CH₃ | —CH₂OH |

-continued

—CH₂—cyc(CH₂)₃— is

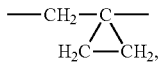

and —CH₂—cyc(CH₂)₄— is

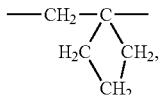

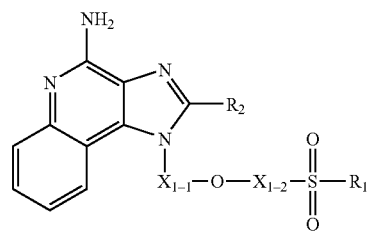

IIa-6

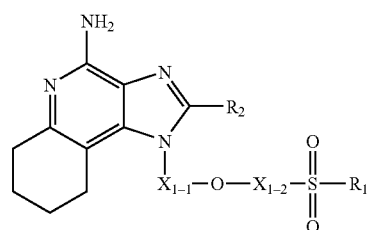

IIIa-4

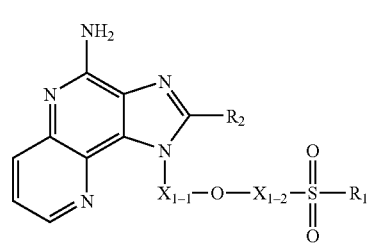

IVa-2

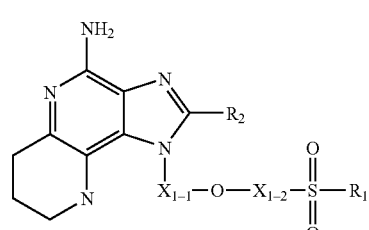

XLII

| $X_{1-1}$ | $X_{1-2}$ | $R_1$ | $R_2$ |
|---|---|---|---|
| —CH₂CH₂CH₂— | —CH₂CH₂CH₂— | —CH₂CH₃ | —(CH₂)₂OH |
| —CH₂CH₂CH₂— | —CH₂CH₂CH₂— | —(CH₂)₂CH₃ | H |
| —CH₂CH₂CH₂— | —CH₂CH₂CH₂— | —(CH₂)₂CH₃ | —CH₃ |
| —CH₂CH₂CH₂— | —CH₂CH₂CH₂— | —(CH₂)₂CH₃ | —CH₂CH₃ |
| —CH₂CH₂CH₂— | —CH₂CH₂CH₂— | —(CH₂)₂CH₃ | —(CH₂)₂CH₃ |
| —CH₂CH₂CH₂— | —CH₂CH₂CH₂— | —(CH₂)₂CH₃ | —(CH₂)₃CH₃ |
| —CH₂CH₂CH₂— | —CH₂CH₂CH₂— | —(CH₂)₂CH₃ | —CH₂OCH₂CH₃ |
| —CH₂CH₂CH₂— | —CH₂CH₂CH₂— | —(CH₂)₂CH₃ | —(CH₂)₂OCH₃ |
| —CH₂CH₂CH₂— | —CH₂CH₂CH₂— | —(CH₂)₂CH₃ | —CH₂OH |
| —CH₂CH₂CH₂— | —CH₂CH₂CH₂— | —(CH₂)₂CH₃ | —(CH₂)₂OH |
| —CH₂CH₂CH₂— | —CH₂CH₂CH₂— | —CH(CH₃)₂ | H |
| —CH₂CH₂CH₂— | —CH₂CH₂CH₂— | —CH(CH₃)₂ | —CH₃ |
| —CH₂CH₂CH₂— | —CH₂CH₂CH₂— | —CH(CH₃)₂ | —CH₂CH₃ |

-continued

—CH₂—cyc(CH₂)₃— is

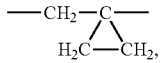

and —CH₂—cyc(CH₂)₄— is

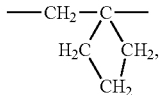

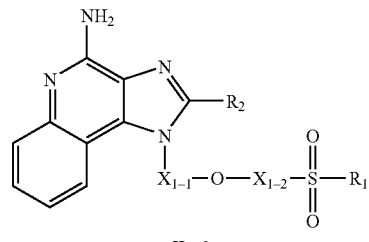

IIa-6

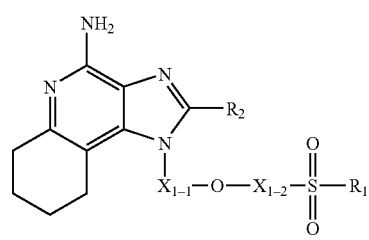

IIIa-4

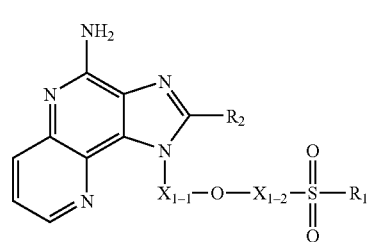

IVa-2

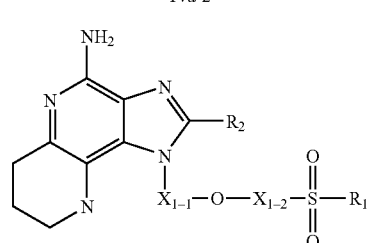

XLII

| $X_{1-1}$ | $X_{1-2}$ | $R_1$ | $R_2$ |
|---|---|---|---|
| —CH₂CH₂CH₂— | —CH₂CH₂CH₂— | —CH(CH₃)₂ | —(CH₂)₂CH₃ |
| —CH₂CH₂CH₂— | —CH₂CH₂CH₂— | —CH(CH₃)₂ | —(CH₂)₃CH₃ |
| —CH₂CH₂CH₂— | —CH₂CH₂CH₂— | —CH(CH₃)₂ | —CH₂OCH₂CH₃ |
| —CH₂CH₂CH₂— | —CH₂CH₂CH₂— | —CH(CH₃)₂ | —(CH₂)₂OCH₃ |
| —CH₂CH₂CH₂— | —CH₂CH₂CH₂— | —CH(CH₃)₂ | —CH₂OH |
| —CH₂CH₂CH₂— | —CH₂CH₂CH₂— | —CH(CH₃)₂ | —(CH₂)₂OH |
| —CH₂C(CH₃)₂— | —CH₂CH₂— | —CH₃ | H |
| —CH₂C(CH₃)₂— | —CH₂CH₂— | —CH₃ | —CH₃ |
| —CH₂C(CH₃)₂— | —CH₂CH₂— | —CH₃ | —CH₂CH₃ |
| —CH₂C(CH₃)₂— | —CH₂CH₂— | —CH₃ | —(CH₂)₂CH₃ |
| —CH₂C(CH₃)₂— | —CH₂CH₂— | —CH₃ | —(CH₂)₃CH₃ |
| —CH₂C(CH₃)₂— | —CH₂CH₂— | —CH₃ | —CH₂OCH₂CH₃ |
| —CH₂C(CH₃)₂— | —CH₂CH₂— | —CH₃ | —(CH₂)₂OCH₃ |

-continued

—CH₂—cyc(CH₂)₃— is

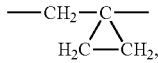

and —CH₂—cyc(CH₂)₄— is

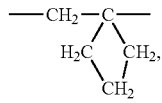

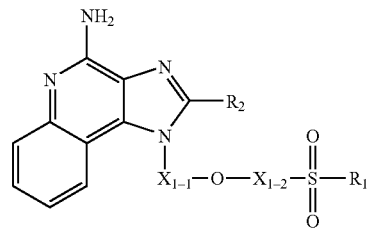

IIa-6

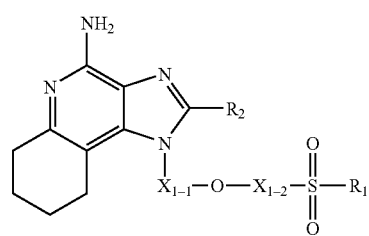

IIIa-4

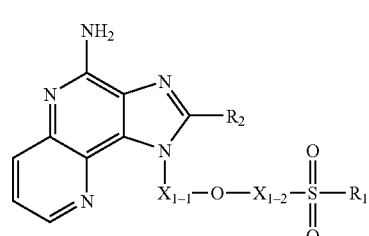

IVa-2

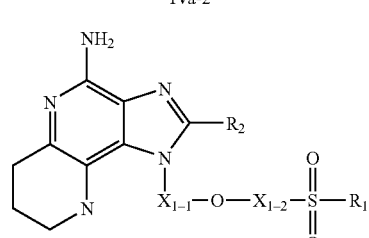

XLII

| X₁₋₁ | X₁₋₂ | R₁ | R₂ |
|---|---|---|---|
| —CH₂C(CH₃)₂— | —CH₂CH₂— | —CH₃ | —CH₂OH |
| —CH₂C(CH₃)₂— | —CH₂CH₂— | —CH₃ | —(CH₂)₂OH |
| —CH₂C(CH₃)₂— | —CH₂CH₂— | —CH₂CH₃ | H |
| —CH₂C(CH₃)₂— | —CH₂CH₂— | —CH₂CH₃ | —CH₃ |
| —CH₂C(CH₃)₂— | —CH₂CH₂— | —CH₂CH₃ | —CH₂CH₃ |
| —CH₂C(CH₃)₂— | —CH₂CH₂— | —CH₂CH₃ | —(CH₂)₂CH₃ |
| —CH₂C(CH₃)₂— | —CH₂CH₂— | —CH₂CH₃ | —(CH₂)₃CH₃ |
| —CH₂C(CH₃)₂— | —CH₂CH₂— | —CH₂CH₃ | —CH₂OCH₂CH₃ |
| —CH₂C(CH₃)₂— | —CH₂CH₂— | —CH₂CH₃ | —(CH₂)₂OCH₃ |
| —CH₂C(CH₃)₂— | —CH₂CH₂— | —CH₂CH₃ | —CH₂OH |
| —CH₂C(CH₃)₂— | —CH₂CH₂— | —CH₂CH₃ | —(CH₂)₂OH |
| —CH₂C(CH₃)₂— | —CH₂CH₂— | —(CH₂)₂CH₃ | H |
| —CH₂C(CH₃)₂— | —CH₂CH₂— | —(CH₂)₂CH₃ | —CH₃ |

-continued

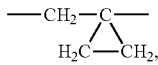

—CH₂—cyc(CH₂)₃— is

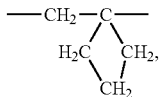

and —CH₂—cyc(CH₂)₄— is

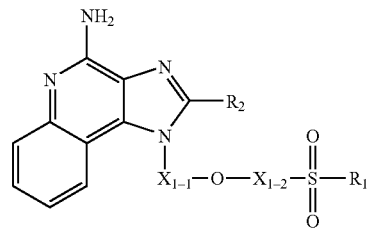

IIa-6

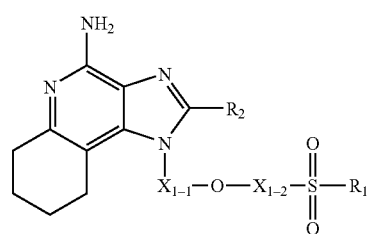

IIIa-4

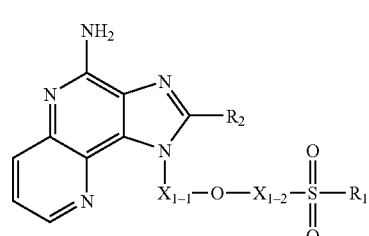

IVa-2

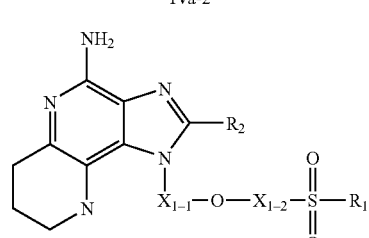

XLII

| X₁₋₁ | X₁₋₂ | R₁ | R₂ |
|---|---|---|---|
| —CH₂C(CH₃)₂— | —CH₂CH₂— | —(CH₂)₂CH₃ | —CH₂CH₃ |
| —CH₂C(CH₃)₂— | —CH₂CH₂— | —(CH₂)₂CH₃ | —(CH₂)₂CH₃ |
| —CH₂C(CH₃)₂— | —CH₂CH₂— | —(CH₂)₂CH₃ | —(CH₂)₃CH₃ |
| —CH₂C(CH₃)₂— | —CH₂CH₂— | —(CH₂)₂CH₃ | —CH₂OCH₂CH₃ |
| —CH₂C(CH₃)₂— | —CH₂CH₂— | —(CH₂)₂CH₃ | —(CH₂)₂OCH₃ |
| —CH₂C(CH₃)₂— | —CH₂CH₂— | —(CH₂)₂CH₃ | —CH₂OH |
| —CH₂C(CH₃)₂— | —CH₂CH₂— | —(CH₂)₂CH₃ | —(CH₂)₂OH |
| —CH₂C(CH₃)₂— | —CH₂CH₂— | —CH(CH₃)₂ | H |
| —CH₂C(CH₃)₂— | —CH₂CH₂— | —CH(CH₃)₂ | —CH₃ |
| —CH₂C(CH₃)₂— | —CH₂CH₂— | —CH(CH₃)₂ | —CH₂CH₃ |
| —CH₂C(CH₃)₂— | —CH₂CH₂— | —CH(CH₃)₂ | —(CH₂)₂CH₃ |
| —CH₂C(CH₃)₂— | —CH₂CH₂— | —CH(CH₃)₂ | —(CH₂)₃CH₃ |
| —CH₂C(CH₃)₂— | —CH₂CH₂— | —CH(CH₃)₂ | —CH₂OCH₂CH₃ |

-continued

—CH₂—cyc(CH₂)₃— is

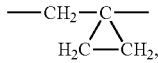

and —CH₂—cyc(CH₂)₄— is

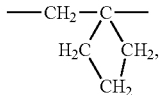

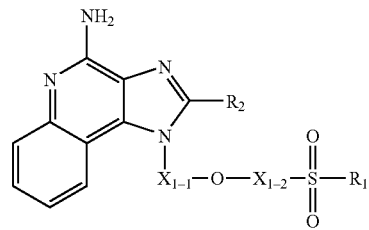

IIa-6

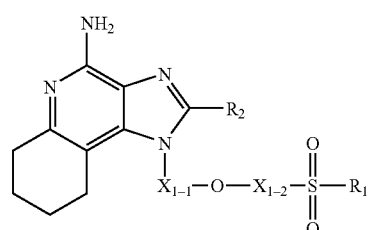

IIIa-4

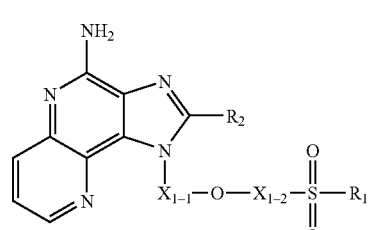

IVa-2

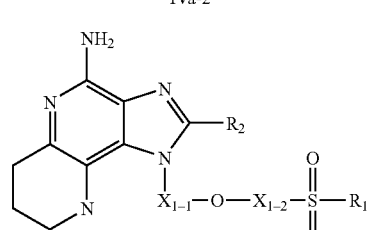

XLII

| $X_{1-1}$ | $X_{1-2}$ | $R_1$ | $R_2$ |
|---|---|---|---|
| —CH₂C(CH₃)₂— | —CH₂CH₂— | —CH(CH₃)₂ | —(CH₂)₂OCH₃ |
| —CH₂C(CH₃)₂— | —CH₂CH₂— | —CH(CH₃)₂ | —CH₂OH |
| —CH₂C(CH₃)₂— | —CH₂CH₂— | —CH(CH₃)₂ | —(CH₂)₂OH |
| —CH₂C(CH₃)₂— | —CH₂CH₂CH₂— | —CH₃ | H |
| —CH₂C(CH₃)₂— | —CH₂CH₂CH₂— | —CH₃ | —CH₃ |
| —CH₂C(CH₃)₂— | —CH₂CH₂CH₂— | —CH₃ | —CH₂CH₃ |
| —CH₂C(CH₃)₂— | —CH₂CH₂CH₂— | —CH₃ | —(CH₂)₂CH₃ |
| —CH₂C(CH₃)₂— | —CH₂CH₂CH₂— | —CH₃ | —(CH₂)₃CH₃ |
| —CH₂C(CH₃)₂— | —CH₂CH₂CH₂— | —CH₃ | —CH₂OCH₂CH₃ |
| —CH₂C(CH₃)₂— | —CH₂CH₂CH₂— | —CH₃ | —(CH₂)₂OCH₃ |
| —CH₂C(CH₃)₂— | —CH₂CH₂CH₂— | —CH₃ | —CH₂OH |
| —CH₂C(CH₃)₂— | —CH₂CH₂CH₂— | —CH₃ | —(CH₂)₂OH |
| —CH₂C(CH₃)₂— | —CH₂CH₂CH₂— | —CH₂CH₃ | H |

-continued

—CH₂—cyc(CH₂)₃— is

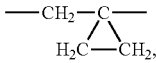

and —CH₂—cyc(CH₂)₄— is

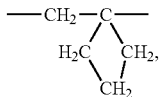

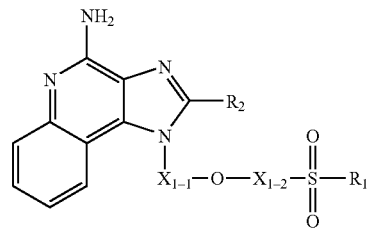

IIa-6

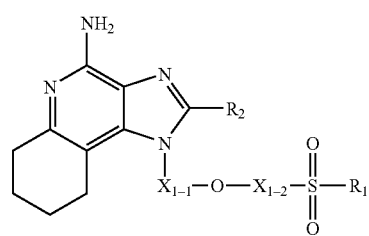

IIIa-4

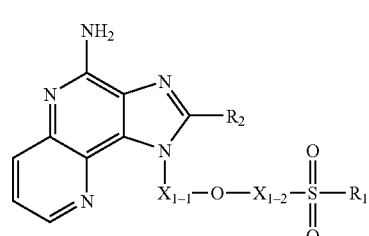

IVa-2

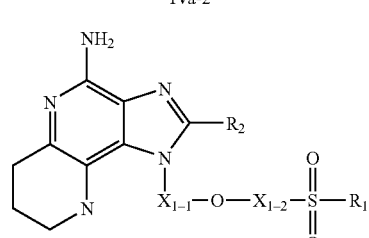

XLII

| $X_{1-1}$ | $X_{1-2}$ | $R_1$ | $R_2$ |
|---|---|---|---|
| —CH₂C(CH₃)₂— | —CH₂CH₂CH₂— | —CH₂CH₃ | —CH₃ |
| —CH₂C(CH₃)₂— | —CH₂CH₂CH₂— | —CH₂CH₃ | —CH₂CH₃ |
| —CH₂C(CH₃)₂— | —CH₂CH₂CH₂— | —CH₂CH₃ | —(CH₂)₂CH₃ |
| —CH₂C(CH₃)₂— | —CH₂CH₂CH₂— | —CH₂CH₃ | —(CH₂)₃CH₃ |
| —CH₂C(CH₃)₂— | —CH₂CH₂CH₂— | —CH₂CH₃ | —CH₂OCH₂CH₃ |
| —CH₂C(CH₃)₂— | —CH₂CH₂CH₂— | —CH₂CH₃ | —(CH₂)₂OCH₃ |
| —CH₂C(CH₃)₂— | —CH₂CH₂CH₂— | —CH₂CH₃ | —CH₂OH |
| —CH₂C(CH₃)₂— | —CH₂CH₂CH₂— | —CH₂CH₃ | —(CH₂)₂OH |
| —CH₂C(CH₃)₂— | —CH₂CH₂CH₂— | —(CH₂)₂CH₃ | H |
| —CH₂C(CH₃)₂— | —CH₂CH₂CH₂— | —(CH₂)₂CH₃ | —CH₃ |
| —CH₂C(CH₃)₂— | —CH₂CH₂CH₂— | —(CH₂)₂CH₃ | —CH₂CH₃ |
| —CH₂C(CH₃)₂— | —CH₂CH₂CH₂— | —(CH₂)₂CH₃ | —(CH₂)₂CH₃ |
| —CH₂C(CH₃)₂— | —CH₂CH₂CH₂— | —(CH₂)₂CH₃ | —(CH₂)₃CH₃ |

-continued

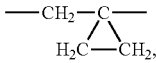   is

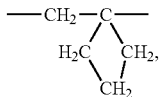

and —CH₂—cyc(CH₂)₄— is

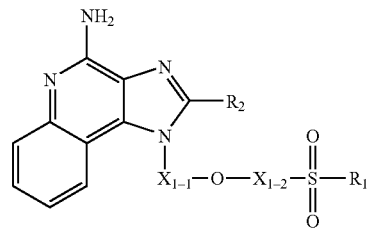

IIa-6

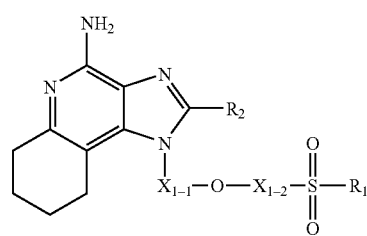

IIIa-4

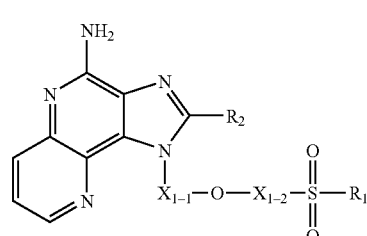

IVa-2

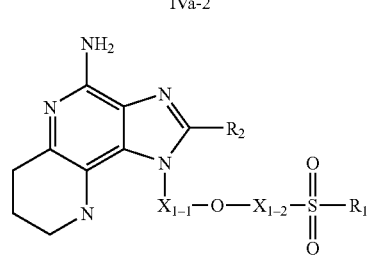

XLII

| X₁₋₁ | X₁₋₂ | R₁ | R₂ |
|---|---|---|---|
| —CH₂C(CH₃)₂— | —CH₂CH₂CH₂— | —(CH₂)₂CH₃ | —CH₂OCH₂CH₃ |
| —CH₂C(CH₃)₂— | —CH₂CH₂CH₂— | —(CH₂)₂CH₃ | —(CH₂)₂OCH₃ |
| —CH₂C(CH₃)₂— | —CH₂CH₂CH₂— | —(CH₂)₂CH₃ | —CH₂OH |
| —CH₂C(CH₃)₂— | —CH₂CH₂CH₂— | —(CH₂)₂CH₃ | —(CH₂)₂OH |
| —CH₂C(CH₃)₂— | —CH₂CH₂CH₂— | —CH(CH₃)₂ | H |
| —CH₂C(CH₃)₂— | —CH₂CH₂CH₂— | —CH(CH₃)₂ | —CH₃ |
| —CH₂C(CH₃)₂— | —CH₂CH₂CH₂— | —CH(CH₃)₂ | —CH₂CH₃ |
| —CH₂C(CH₃)₂— | —CH₂CH₂CH₂— | —CH(CH₃)₂ | —(CH₂)₂CH₃ |
| —CH₂C(CH₃)₂— | —CH₂CH₂CH₂— | —CH(CH₃)₂ | —(CH₂)₃CH₃ |
| —CH₂C(CH₃)₂— | —CH₂CH₂CH₂— | —CH(CH₃)₂ | —CH₂OCH₂CH₃ |
| —CH₂C(CH₃)₂— | —CH₂CH₂CH₂— | —CH(CH₃)₂ | —(CH₂)₂OCH₃ |
| —CH₂C(CH₃)₂— | —CH₂CH₂CH₂— | —CH(CH₃)₂ | —CH₂OH |
| —CH₂C(CH₃)₂— | —CH₂CH₂CH₂— | —CH(CH₃)₂ | —(CH₂)₂OH |

-continued

—CH₂—cyc(CH₂)₃— is

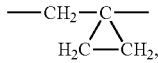

and —CH₂—cyc(CH₂)₄— is

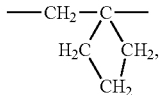

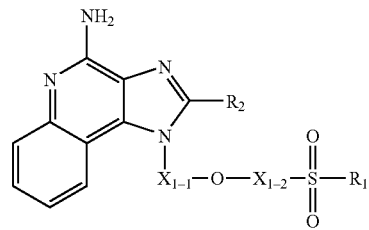

IIa-6

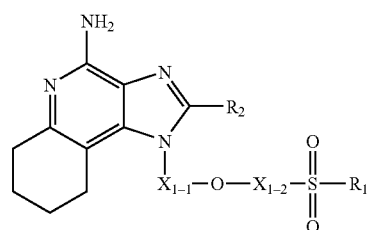

IIIa-4

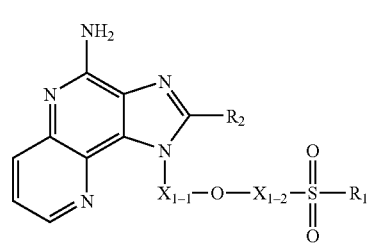

IVa-2

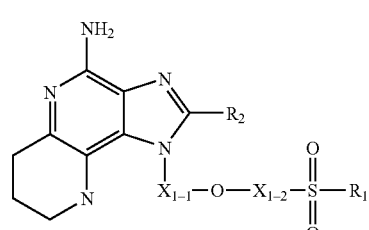

XLII

| $X_{1-1}$ | $X_{1-2}$ | $R_1$ | $R_2$ |
|---|---|---|---|
| —CH₂-cyc(CH₂)₃— | —CH₂CH₂— | —CH₃ | H |
| —CH₂-cyc(CH₂)₃— | —CH₂CH₂— | —CH₃ | —CH₃ |
| —CH₂-cyc(CH₂)₃— | —CH₂CH₂— | —CH₃ | —CH₂CH₃ |
| —CH₂-cyc(CH₂)₃— | —CH₂CH₂— | —CH₃ | —(CH₂)₂CH₃ |
| —CH₂-cyc(CH₂)₃— | —CH₂CH₂— | —CH₃ | —(CH₂)₃CH₃ |
| —CH₂-cyc(CH₂)₃— | —CH₂CH₂— | —CH₃ | —CH₂OCH₂CH₃ |
| —CH₂-cyc(CH₂)₃— | —CH₂CH₂— | —CH₃ | —(CH₂)₂OCH₃ |
| —CH₂-cyc(CH₂)₃— | —CH₂CH₂— | —CH₃ | —CH₂OH |
| —CH₂-cyc(CH₂)₃— | —CH₂CH₂— | —CH₃ | —(CH₂)₂OH |
| —CH₂-cyc(CH₂)₃— | —CH₂CH₂— | —CH₂CH₃ | H |
| —CH₂-cyc(CH₂)₃— | —CH₂CH₂— | —CH₂CH₃ | —CH₃ |
| —CH₂-cyc(CH₂)₃— | —CH₂CH₂— | —CH₂CH₃ | —CH₂CH₃ |
| —CH₂-cyc(CH₂)₃— | —CH₂CH₂— | —CH₂CH₃ | —(CH₂)₂CH₃ |

-continued

—CH₂—cyc(CH₂)₃— is

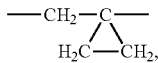

and —CH₂—cyc(CH₂)₄— is

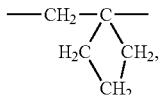

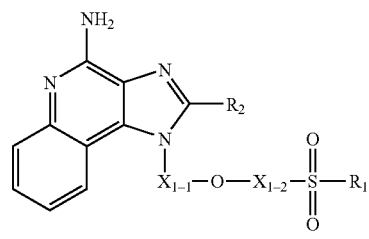

IIa-6

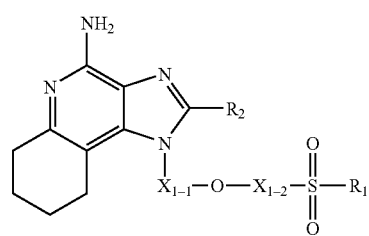

IIIa-4

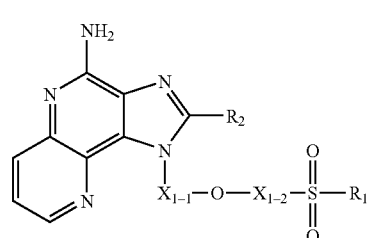

IVa-2

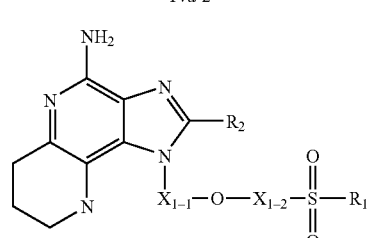

XLII

| $X_{1-1}$ | $X_{1-2}$ | $R_1$ | $R_2$ |
|---|---|---|---|
| —CH₂-cyc(CH₂)₃— | —CH₂CH₂— | —CH₂CH₃ | —(CH₂)₃CH₃ |
| —CH₂-cyc(CH₂)₃— | —CH₂CH₂— | —CH₂CH₃ | —CH₂OCH₂CH₃ |
| —CH₂-cyc(CH₂)₃— | —CH₂CH₂— | —CH₂CH₃ | —(CH₂)₂OCH₃ |
| —CH₂-cyc(CH₂)₃— | —CH₂CH₂— | —CH₂CH₃ | —CH₂OH |
| —CH₂-cyc(CH₂)₃— | —CH₂CH₂— | —CH₂CH₃ | —(CH₂)₂OH |
| —CH₂-cyc(CH₂)₃— | —CH₂CH₂— | —(CH₂)₂CH₃ | H |
| —CH₂-cyc(CH₂)₃— | —CH₂CH₂— | —(CH₂)₂CH₃ | —CH₃ |
| —CH₂-cyc(CH₂)₃— | —CH₂CH₂— | —(CH₂)₂CH₃ | —CH₂CH₃ |
| —CH₂-cyc(CH₂)₃— | —CH₂CH₂— | —(CH₂)₂CH₃ | —(CH₂)₂CH₃ |
| —CH₂-cyc(CH₂)₃— | —CH₂CH₂— | —(CH₂)₂CH₃ | —(CH₂)₃CH₃ |
| —CH₂-cyc(CH₂)₃— | —CH₂CH₂— | —(CH₂)₂CH₃ | —CH₂OCH₂CH₃ |
| —CH₂-cyc(CH₂)₃— | —CH₂CH₂— | —(CH₂)₂CH₃ | —(CH₂)₂OCH₃ |
| —CH₂-cyc(CH₂)₃— | —CH₂CH₂— | —(CH₂)₂CH₃ | —CH₂OH |

-continued

—CH$_2$—cyc(CH$_2$)$_3$— is

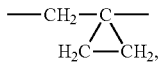

and —CH$_2$—cyc(CH$_2$)$_4$— is

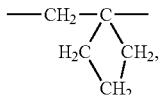

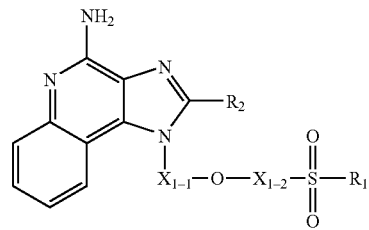

IIa-6

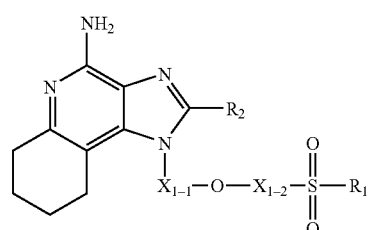

IIIa-4

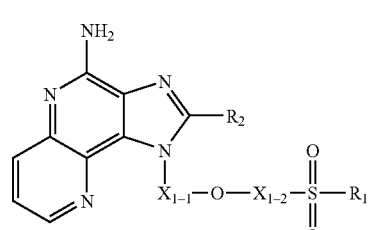

IVa-2

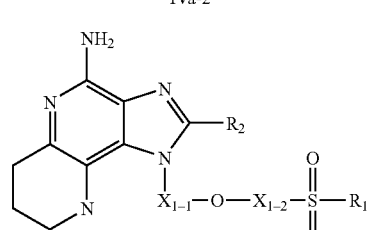

XLII

| X$_{1-1}$ | X$_{1-2}$ | R$_1$ | R$_2$ |
|---|---|---|---|
| —CH$_2$-cyc(CH$_2$)$_3$— | —CH$_2$CH$_2$— | —(CH$_2$)$_2$CH$_3$ | —(CH$_2$)$_2$OH |
| —CH$_2$-cyc(CH$_2$)$_3$— | —CH$_2$CH$_2$— | —CH(CH$_3$)$_2$ | H |
| —CH$_2$-cyc(CH$_2$)$_3$— | —CH$_2$CH$_2$— | —CH(CH$_3$)$_2$ | —CH$_3$ |
| —CH$_2$-cyc(CH$_2$)$_3$— | —CH$_2$CH$_2$— | —CH(CH$_3$)$_2$ | —CH$_2$CH$_3$ |
| —CH$_2$-cyc(CH$_2$)$_3$— | —CH$_2$CH$_2$— | —CH(CH$_3$)$_2$ | —(CH$_2$)$_2$CH$_3$ |
| —CH$_2$-cyc(CH$_2$)$_3$— | —CH$_2$CH$_2$— | —CH(CH$_3$)$_2$ | —(CH$_2$)$_3$CH$_3$ |
| —CH$_2$-cyc(CH$_2$)$_3$— | —CH$_2$CH$_2$— | —CH(CH$_3$)$_2$ | —CH$_2$OCH$_2$CH$_3$ |
| —CH$_2$-cyc(CH$_2$)$_3$— | —CH$_2$CH$_2$— | —CH(CH$_3$)$_2$ | —(CH$_2$)$_2$OCH$_3$ |
| —CH$_2$-cyc(CH$_2$)$_3$— | —CH$_2$CH$_2$— | —CH(CH$_3$)$_2$ | —CH$_2$OH |
| —CH$_2$-cyc(CH$_2$)$_3$— | —CH$_2$CH$_2$— | —CH(CH$_3$)$_2$ | —(CH$_2$)$_2$OH |
| —CH$_2$-cyc(CH$_2$)$_3$— | —CH$_2$CH$_2$CH$_2$— | —CH$_3$ | H |
| —CH$_2$-cyc(CH$_2$)$_3$— | —CH$_2$CH$_2$CH$_2$— | —CH$_3$ | —CH$_3$ |
| —CH$_2$-cyc(CH$_2$)$_3$— | —CH$_2$CH$_2$CH$_2$— | —CH$_3$ | —CH$_2$CH$_3$ |

-continued

—CH₂—cyc(CH₂)₃— is

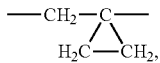

and —CH₂—cyc(CH₂)₄— is

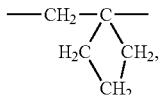

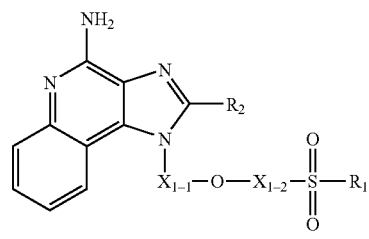

IIa-6

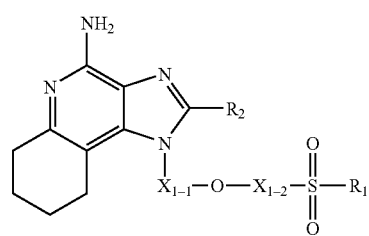

IIIa-4

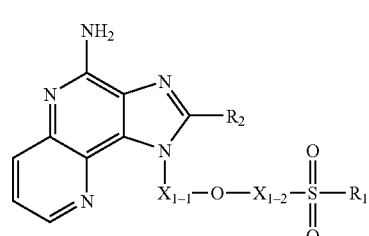

IVa-2

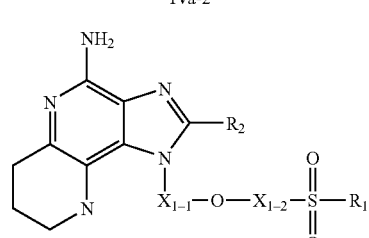

XLII

| X₁₋₁ | X₁₋₂ | R₁ | R₂ |
|---|---|---|---|
| —CH₂-cyc(CH₂)₃— | —CH₂CH₂CH₂— | —CH₃ | —(CH₂)₂CH₃ |
| —CH₂-cyc(CH₂)₃— | —CH₂CH₂CH₂— | —CH₃ | —(CH₂)₃CH₃ |
| —CH₂-cyc(CH₂)₃— | —CH₂CH₂CH₂— | —CH₃ | —CH₂OCH₂CH₃ |
| —CH₂-cyc(CH₂)₃— | —CH₂CH₂CH₂— | —CH₃ | —(CH₂)₂OCH₃ |
| —CH₂-cyc(CH₂)₃— | —CH₂CH₂CH₂— | —CH₃ | —CH₂OH |
| —CH₂-cyc(CH₂)₃— | —CH₂CH₂CH₂— | —CH₃ | —(CH₂)₂OH |
| —CH₂-cyc(CH₂)₃— | —CH₂CH₂CH₂— | —CH₂CH₃ | H |
| —CH₂-cyc(CH₂)₃— | —CH₂CH₂CH₂— | —CH₂CH₃ | —CH₃ |
| —CH₂-cyc(CH₂)₃— | —CH₂CH₂CH₂— | —CH₂CH₃ | —CH₂CH₃ |
| —CH₂-cyc(CH₂)₃— | —CH₂CH₂CH₂— | —CH₂CH₃ | —(CH₂)₂CH₃ |
| —CH₂-cyc(CH₂)₃— | —CH₂CH₂CH₂— | —CH₂CH₃ | —(CH₂)₃CH₃ |
| —CH₂-cyc(CH₂)₃— | —CH₂CH₂CH₂— | —CH₂CH₃ | —CH₂OCH₂CH₃ |
| —CH₂-cyc(CH₂)₃— | —CH₂CH₂CH₂— | —CH₂CH₃ | —(CH₂)₂OCH₃ |

-continued

—CH₂—cyc(CH₂)₃— is

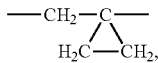

and —CH₂—cyc(CH₂)₄— is

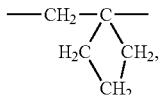

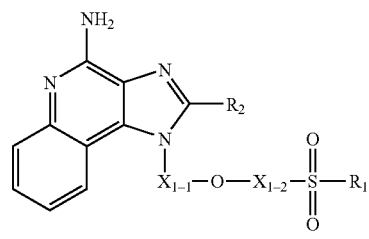

IIa-6

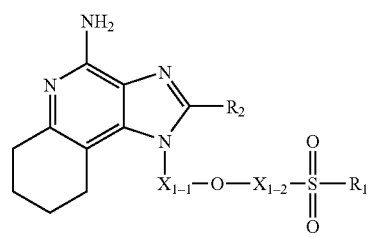

IIIa-4

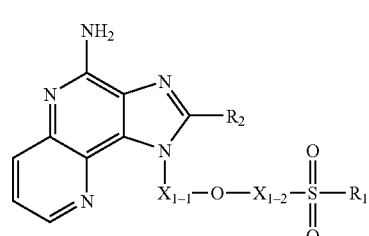

IVa-2

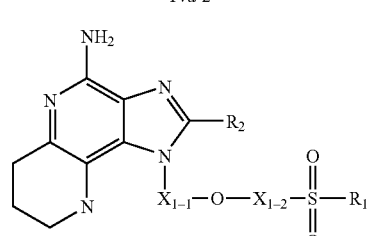

XLII

| X₁₋₁ | X₁₋₂ | R₁ | R₂ |
|---|---|---|---|
| —CH₂-cyc(CH₂)₃— | —CH₂CH₂CH₂— | —CH₂CH₃ | —CH₂OH |
| —CH₂-cyc(CH₂)₃— | —CH₂CH₂CH₂— | —CH₂CH₃ | —(CH₂)₂OH |
| —CH₂-cyc(CH₂)₃— | —CH₂CH₂CH₂— | —(CH₂)₂CH₃ | H |
| —CH₂-cyc(CH₂)₃— | —CH₂CH₂CH₂— | —(CH₂)₂CH₃ | —CH₃ |
| —CH₂-cyc(CH₂)₃— | —CH₂CH₂CH₂— | —(CH₂)₂CH₃ | —CH₂CH₃ |
| —CH₂-cyc(CH₂)₃— | —CH₂CH₂CH₂— | —(CH₂)₂CH₃ | —(CH₂)₂CH₃ |
| —CH₂-cyc(CH₂)₃— | —CH₂CH₂CH₂— | —(CH₂)₂CH₃ | —(CH₂)₃CH₃ |
| —CH₂-cyc(CH₂)₃— | —CH₂CH₂CH₂— | —(CH₂)₂CH₃ | —CH₂OCH₂CH₃ |
| —CH₂-cyc(CH₂)₃— | —CH₂CH₂CH₂— | —(CH₂)₂CH₃ | —(CH₂)₂OCH₃ |
| —CH₂-cyc(CH₂)₃— | —CH₂CH₂CH₂— | —(CH₂)₂CH₃ | —CH₂OH |
| —CH₂-cyc(CH₂)₃— | —CH₂CH₂CH₂— | —(CH₂)₂CH₃ | —(CH₂)₂OH |
| —CH₂-cyc(CH₂)₃— | —CH₂CH₂CH₂— | —CH(CH₃)₂ | H |
| —CH₂-cyc(CH₂)₃— | —CH₂CH₂CH₂— | —CH(CH₃)₂ | —CH₃ |

-continued

—CH₂—cyc(CH₂)₃— is

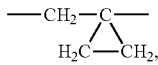

and —CH₂—cyc(CH₂)₄— is

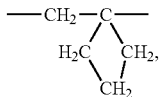

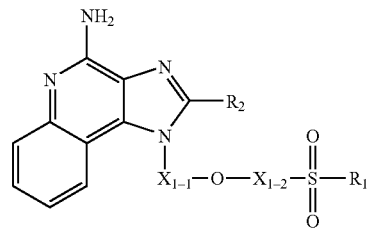

IIa-6

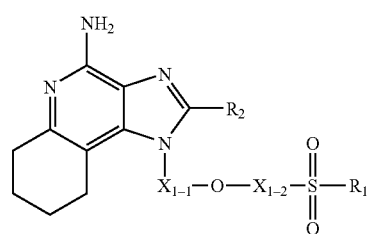

IIIa-4

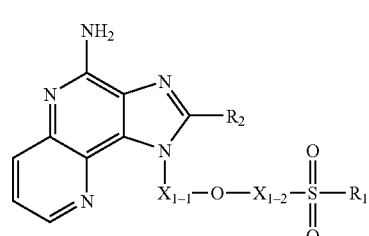

IVa-2

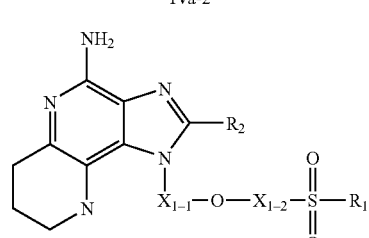

XLII

| X₁₋₁ | X₁₋₂ | R₁ | R₂ |
|---|---|---|---|
| —CH₂-cyc(CH₂)₃— | —CH₂CH₂CH₂— | —CH(CH₃)₂ | —CH₂CH₃ |
| —CH₂-cyc(CH₂)₃— | —CH₂CH₂CH₂— | —CH(CH₃)₂ | —(CH₂)₂CH₃ |
| —CH₂-cyc(CH₂)₃— | —CH₂CH₂CH₂— | —CH(CH₃)₂ | —(CH₂)₃CH₃ |
| —CH₂-cyc(CH₂)₃— | —CH₂CH₂CH₂— | —CH(CH₃)₂ | —CH₂OCH₂CH₃ |
| —CH₂-cyc(CH₂)₃— | —CH₂CH₂CH₂— | —CH(CH₃)₂ | —(CH₂)₂OCH₃ |
| —CH₂-cyc(CH₂)₃— | —CH₂CH₂CH₂— | —CH(CH₃)₂ | —CH₂OH |
| —CH₂-cyc(CH₂)₃— | —CH₂CH₂CH₂— | —CH(CH₃)₂ | —(CH₂)₂OH |
| —CH₂-cyc(CH₂)₄— | —CH₂CH₂— | —CH₃ | H |
| —CH₂-cyc(CH₂)₄— | —CH₂CH₂— | —CH₃ | —CH₃ |
| —CH₂-cyc(CH₂)₄— | —CH₂CH₂— | —CH₃ | —CH₂CH₃ |
| —CH₂-cyc(CH₂)₄— | —CH₂CH₂— | —CH₃ | —(CH₂)₂CH₃ |
| —CH₂-cyc(CH₂)₄— | —CH₂CH₂— | —CH₃ | —(CH₂)₃CH₃ |
| —CH₂-cyc(CH₂)₄— | —CH₂CH₂— | —CH₃ | —CH₂OCH₂CH₃ |

-continued

—CH₂—cyc(CH₂)₃— is

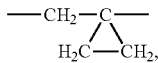

and —CH₂—cyc(CH₂)₄— is

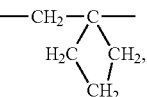

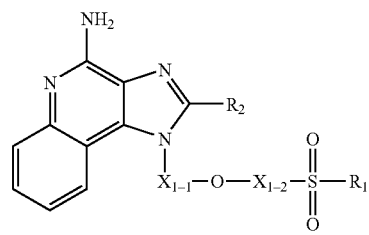

IIa-6

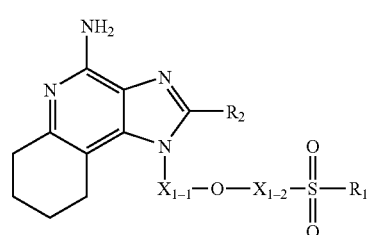

IIIa-4

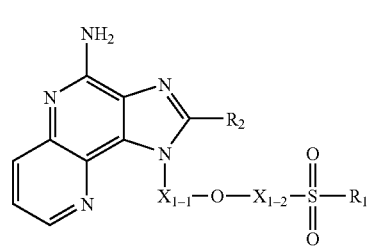

IVa-2

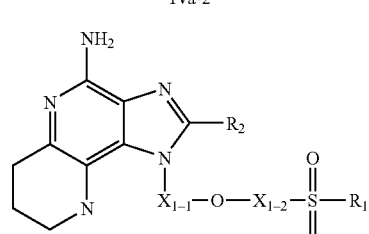

XLII

| $X_{1-1}$ | $X_{1-2}$ | $R_1$ | $R_2$ |
|---|---|---|---|
| —CH₂-cyc(CH₂)₄— | —CH₂CH₂— | —CH₃ | —(CH₂)₂OCH₃ |
| —CH₂-cyc(CH₂)₄— | —CH₂CH₂— | —CH₃ | —CH₂OH |
| —CH₂-cyc(CH₂)₄— | —CH₂CH₂— | —CH₃ | —(CH₂)₂OH |
| —CH₂-cyc(CH₂)₄— | —CH₂CH₂— | —CH₂CH₃ | H |
| —CH₂-cyc(CH₂)₄— | —CH₂CH₂— | —CH₂CH₃ | —CH₃ |
| —CH₂-cyc(CH₂)₄— | —CH₂CH₂— | —CH₂CH₃ | —CH₂CH₃ |
| —CH₂-cyc(CH₂)₄— | —CH₂CH₂— | —CH₂CH₃ | —(CH₂)₂CH₃ |
| —CH₂-cyc(CH₂)₄— | —CH₂CH₂— | —CH₂CH₃ | —(CH₂)₃CH₃ |
| —CH₂-cyc(CH₂)₄— | —CH₂CH₂— | —CH₂CH₃ | —CH₂OCH₂CH₃ |
| —CH₂-cyc(CH₂)₄— | —CH₂CH₂— | —CH₂CH₃ | —(CH₂)₂OCH₃ |
| —CH₂-cyc(CH₂)₄— | —CH₂CH₂— | —CH₂CH₃ | —CH₂OH |
| —CH₂-cyc(CH₂)₄— | —CH₂CH₂— | —CH₂CH₃ | —(CH₂)₂OH |
| —CH₂-cyc(CH₂)₄— | —CH₂CH₂— | —(CH₂)₂CH₃ | H |

-continued

—CH$_2$—cyc(CH$_2$)$_3$— is

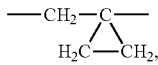

and —CH$_2$—cyc(CH$_2$)$_4$— is

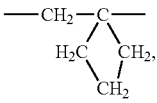

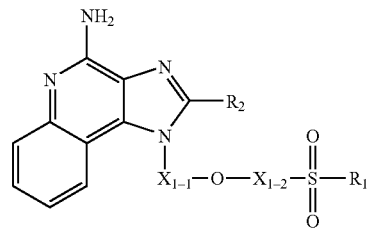

IIa-6

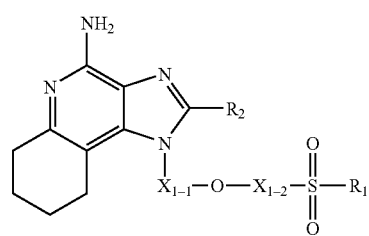

IIIa-4

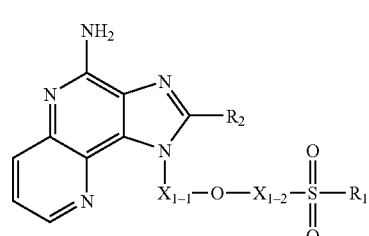

IVa-2

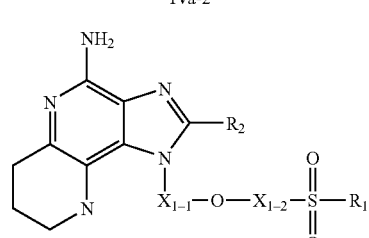

XLII

| X$_{1-1}$ | X$_{1-2}$ | R$_1$ | R$_2$ |
|---|---|---|---|
| —CH$_2$-cyc(CH$_2$)$_4$— | —CH$_2$CH$_2$— | —(CH$_2$)$_2$CH$_3$ | —CH$_3$ |
| —CH$_2$-cyc(CH$_2$)$_4$— | —CH$_2$CH$_2$— | —(CH$_2$)$_2$CH$_3$ | —CH$_2$CH$_3$ |
| —CH$_2$-cyc(CH$_2$)$_4$— | —CH$_2$CH$_2$— | —(CH$_2$)$_2$CH$_3$ | —(CH$_2$)$_2$CH$_3$ |
| —CH$_2$-cyc(CH$_2$)$_4$— | —CH$_2$CH$_2$— | —(CH$_2$)$_2$CH$_3$ | —(CH$_2$)$_3$CH$_3$ |
| —CH$_2$-cyc(CH$_2$)$_4$— | —CH$_2$CH$_2$— | —(CH$_2$)$_2$CH$_3$ | —CH$_2$OCH$_2$CH$_3$ |
| —CH$_2$-cyc(CH$_2$)$_4$— | —CH$_2$CH$_2$— | —(CH$_2$)$_2$CH$_3$ | —(CH$_2$)$_2$OCH$_3$ |
| —CH$_2$-cyc(CH$_2$)$_4$— | —CH$_2$CH$_2$— | —(CH$_2$)$_2$CH$_3$ | —CH$_2$OH |
| —CH$_2$-cyc(CH$_2$)$_4$— | —CH$_2$CH$_2$— | —(CH$_2$)$_2$CH$_3$ | —(CH$_2$)$_2$OH |
| —CH$_2$-cyc(CH$_2$)$_4$— | —CH$_2$CH$_2$— | —CH(CH$_3$)$_2$ | H |
| —CH$_2$-cyc(CH$_2$)$_4$— | —CH$_2$CH$_2$— | —CH(CH$_3$)$_2$ | —CH$_3$ |
| —CH$_2$-cyc(CH$_2$)$_4$— | —CH$_2$CH$_2$— | —CH(CH$_3$)$_2$ | —CH$_2$CH$_3$ |
| —CH$_2$-cyc(CH$_2$)$_4$— | —CH$_2$CH$_2$— | —CH(CH$_3$)$_2$ | —(CH$_2$)$_2$CH$_3$ |
| —CH$_2$-cyc(CH$_2$)$_4$— | —CH$_2$CH$_2$— | —CH(CH$_3$)$_2$ | —(CH$_2$)$_3$CH$_3$ |

-continued

—CH₂—cyc(CH₂)₃— is

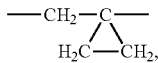

and —CH₂—cyc(CH₂)₄— is

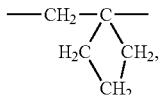

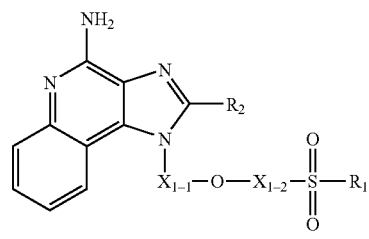

IIa-6

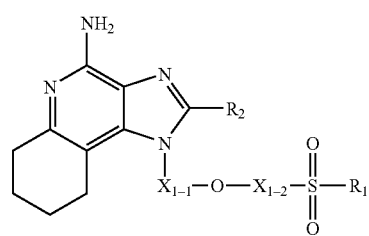

IIIa-4

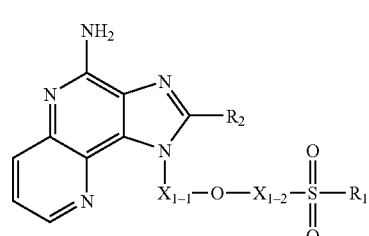

IVa-2

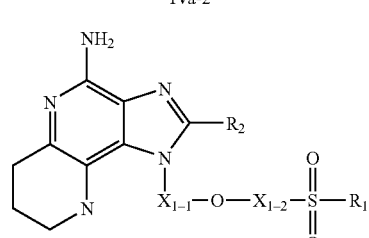

XLII

| $X_{1-1}$ | $X_{1-2}$ | $R_1$ | $R_2$ |
|---|---|---|---|
| —CH₂-cyc(CH₂)₄— | —CH₂CH₂— | —CH(CH₃)₂ | —CH₂OCH₂CH₃ |
| —CH₂-cyc(CH₂)₄— | —CH₂CH₂— | —CH(CH₃)₂ | —(CH₂)₂OCH₃ |
| —CH₂-cyc(CH₂)₄— | —CH₂CH₂— | —CH(CH₃)₂ | —CH₂OH |
| —CH₂-cyc(CH₂)₄— | —CH₂CH₂— | —CH(CH₃)₂ | —(CH₂)₂OH |
| —CH₂-cyc(CH₂)₄— | —CH₂CH₂CH₂— | —CH₃ | H |
| —CH₂-cyc(CH₂)₄— | —CH₂CH₂CH₂— | —CH₃ | —CH₃ |
| —CH₂-cyc(CH₂)₄— | —CH₂CH₂CH₂— | —CH₃ | —CH₂CH₃ |
| —CH₂-cyc(CH₂)₄— | —CH₂CH₂CH₂— | —CH₃ | —(CH₂)₂CH₃ |
| —CH₂-cyc(CH₂)₄— | —CH₂CH₂CH₂— | —CH₃ | —(CH₂)₃CH₃ |
| —CH₂-cyc(CH₂)₄— | —CH₂CH₂CH₂— | —CH₃ | —CH₂OCH₂CH₃ |
| —CH₂-cyc(CH₂)₄— | —CH₂CH₂CH₂— | —CH₃ | —(CH₂)₂OCH₃ |
| —CH₂-cyc(CH₂)₄— | —CH₂CH₂CH₂— | —CH₃ | —CH₂OH |
| —CH₂-cyc(CH₂)₄— | —CH₂CH₂CH₂— | —CH₃ | —(CH₂)₂OH |

-continued

—CH₂—cyc(CH₂)₃— is

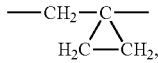

and —CH₂—cyc(CH₂)₄— is

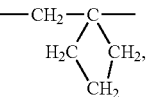

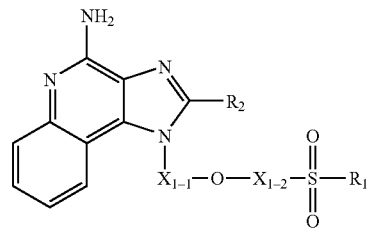

IIa-6

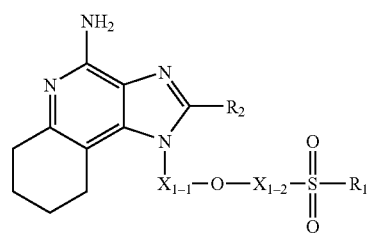

IIIa-4

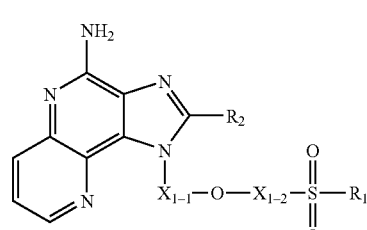

IVa-2

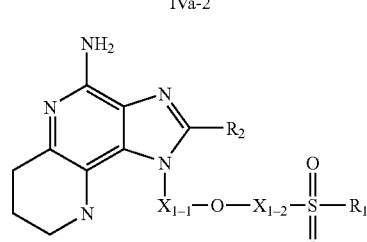

XLII

| $X_{1-1}$ | $X_{1-2}$ | $R_1$ | $R_2$ |
|---|---|---|---|
| —CH₂-cyc(CH₂)₄— | —CH₂CH₂CH₂— | —CH₂CH₃ | H |
| —CH₂-cyc(CH₂)₄— | —CH₂CH₂CH₂— | —CH₂CH₃ | —CH₃ |
| —CH₂-cyc(CH₂)₄— | —CH₂CH₂CH₂— | —CH₂CH₃ | —CH₂CH₃ |
| —CH₂-cyc(CH₂)₄— | —CH₂CH₂CH₂— | —CH₂CH₃ | —(CH₂)₂CH₃ |
| —CH₂-cyc(CH₂)₄— | —CH₂CH₂CH₂— | —CH₂CH₃ | —(CH₂)₃CH₃ |
| —CH₂-cyc(CH₂)₄— | —CH₂CH₂CH₂— | —CH₂CH₃ | —CH₂OCH₂CH₃ |
| —CH₂-cyc(CH₂)₄— | —CH₂CH₂CH₂— | —CH₂CH₃ | —(CH₂)₂OCH₃ |
| —CH₂-cyc(CH₂)₄— | —CH₂CH₂CH₂— | —CH₂CH₃ | —CH₂OH |
| —CH₂-cyc(CH₂)₄— | —CH₂CH₂CH₂— | —CH₂CH₃ | —(CH₂)₂OH |
| —CH₂-cyc(CH₂)₄— | —CH₂CH₂CH₂— | —(CH₂)₂CH₃ | H |
| —CH₂-cyc(CH₂)₄— | —CH₂CH₂CH₂— | —(CH₂)₂CH₃ | —CH₃ |
| —CH₂-cyc(CH₂)₄— | —CH₂CH₂CH₂— | —(CH₂)₂CH₃ | —CH₂CH₃ |
| —CH₂-cyc(CH₂)₄— | —CH₂CH₂CH₂— | —(CH₂)₂CH₃ | —(CH₂)₂CH₃ |

-continued

—CH₂—cyc(CH₂)₃— is

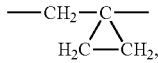

and —CH₂—cyc(CH₂)₄— is

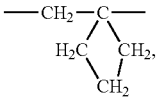

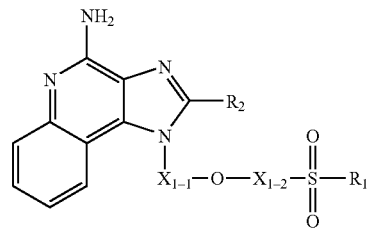

IIa-6

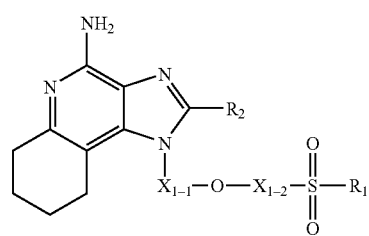

IIIa-4

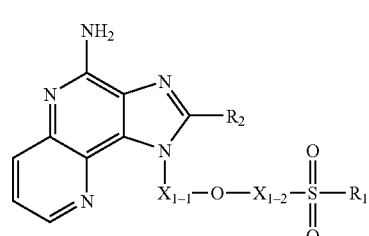

IVa-2

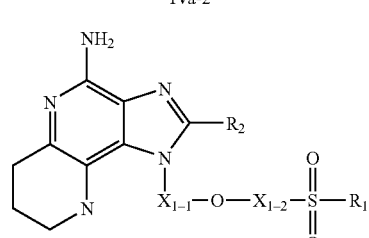

XLII

| $X_{1-1}$ | $X_{1-2}$ | $R_1$ | $R_2$ |
|---|---|---|---|
| —CH₂-cyc(CH₂)₄— | —CH₂CH₂CH₂— | —(CH₂)₂CH₃ | —(CH₂)₃CH₃ |
| —CH₂-cyc(CH₂)₄— | —CH₂CH₂CH₂— | —(CH₂)₂CH₃ | —CH₂OCH₂CH₃ |
| —CH₂-cyc(CH₂)₄— | —CH₂CH₂CH₂— | —(CH₂)₂CH₃ | —(CH₂)₂OCH₃ |
| —CH₂-cyc(CH₂)₄— | —CH₂CH₂CH₂— | —(CH₂)₂CH₃ | —CH₂OH |
| —CH₂-cyc(CH₂)₄— | —CH₂CH₂CH₂— | —(CH₂)₂CH₃ | —(CH₂)₂OH |
| —CH₂-cyc(CH₂)₄— | —CH₂CH₂CH₂— | —CH(CH₃)₂ | H |
| —CH₂-cyc(CH₂)₄— | —CH₂CH₂CH₂— | —CH(CH₃)₂ | —CH₃ |
| —CH₂-cyc(CH₂)₄— | —CH₂CH₂CH₂— | —CH(CH₃)₂ | —CH₂CH₃ |
| —CH₂-cyc(CH₂)₄— | —CH₂CH₂CH₂— | —CH(CH₃)₂ | —(CH₂)₂CH₃ |
| —CH₂-cyc(CH₂)₄— | —CH₂CH₂CH₂— | —CH(CH₃)₂ | —(CH₂)₃CH₃ |
| —CH₂-cyc(CH₂)₄— | —CH₂CH₂CH₂— | —CH(CH₃)₂ | —CH₂OCH₂CH₃ |
| —CH₂-cyc(CH₂)₄— | —CH₂CH₂CH₂— | —CH(CH₃)₂ | —(CH₂)₂OCH₃ |
| —CH₂-cyc(CH₂)₄— | —CH₂CH₂CH₂— | —CH(CH₃)₂ | —CH₂OH |

-continued

—CH₂—cyc(CH₂)₃— is

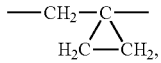

and —CH₂—cyc(CH₂)₄— is

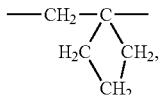

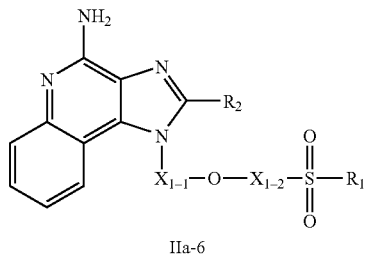

IIa-6

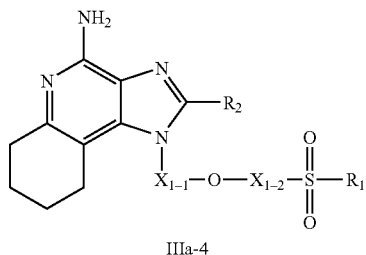

IIIa-4

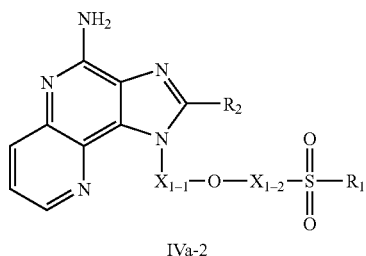

IVa-2

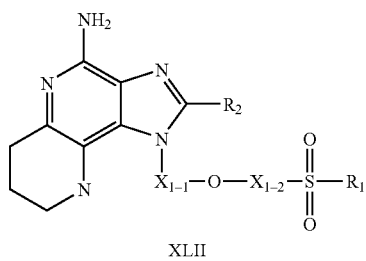

XLII

| $X_{1-1}$ | $X_{1-2}$ | $R_1$ | $R_2$ |
|---|---|---|---|
| —CH₂-cyc(CH₂)₄— | —CH₂CH₂CH₂— | —CH(CH₃)₂ | —(CH₂)₂OH |

Cytokine Induction in Human Cells

Compounds of the invention have been found to induce cytokine biosynthesis when tested using the method described below.

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4\times10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30-0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (a) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula Ia:

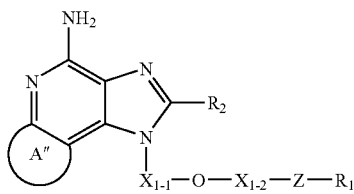

Ia wherein:
$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;

Z is selected from the group consisting of —S—, —S(O)—, and —S(O)$_2$—;

$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino,
$C_{1-10}$ alkylamino, di($C_{1-10}$ alkyl)amino, and in the case of $C_{1-10}$ alkyl, $C_{2-10}$ alkenyl,
$C_{2-10}$ alkynyl, and heterocyclyl, oxo; wherein heteroaryl,
$C_{1-10}$ alkylheteroarylenyl, and heterocyclyl are attached to Z through a carbon atom;

A" is a fused benzene ring, wherein the benzene ring is unsubstituted or substituted by one or more R groups, or A" is a fused cyclohexene ring, wherein the ring is fully saturated except for the bond where the ring is fused, wherein the cyclohexene ring is unsubstituted or substituted by one or more $R_4$ groups;

each R is independently selected from the group consisting of alkyl, alkoxy, hydroxy, fluoro, and trifluoromethyl;

each $R_4$ is independently selected from the group consisting of halogen, hydroxy, alkyl, alkenyl, haloalkyl, alkoxy, alkylthio, and —N($R_9$)$_2$;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—,    —S(O)$_{0-2}$—,    —S(O)$_2$—N($R_8$)—,

—C($R_6$)—,    —C($R_6$)—O—,    —O—C($R_6$)—,

—O—C(O)—O—,    —N($R_8$)—Q—,

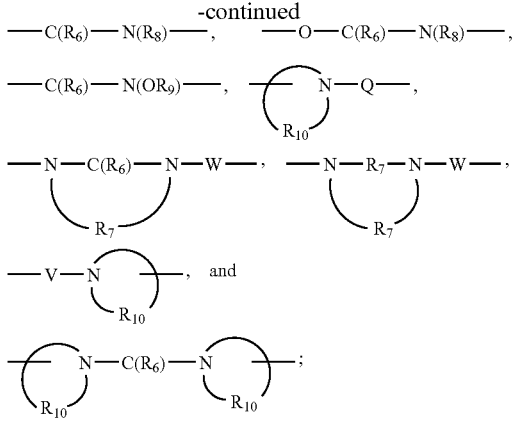

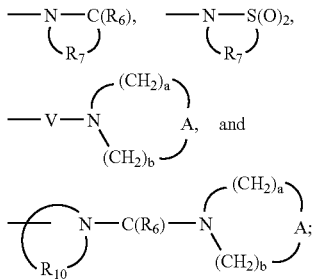

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

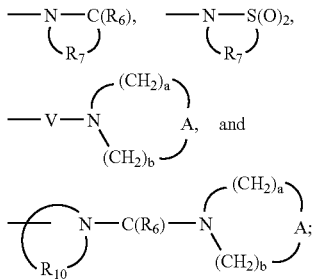

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

2. A compound of the Formula IIa:

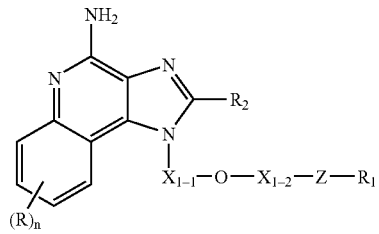

wherein:
$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;
Z is selected from the group consisting of —S—, —S(O)—, and —S(O)$_2$—;
$R_1$ is selected from the group consisting of:
$C_{1-10}$ alkyl,
$C_{2-10}$ alkenyl,
$C_{2-10}$ alkynyl,
aryl,
aryl-$C_{1-10}$ alkylenyl,
aryloxy-$C_{1-10}$ alkylenyl,
$C_{1-10}$ alkylarylenyl,
heteroaryl,
heteroaryl-$C_{1-10}$ alkylenyl,
heteroaryloxy-$C_{1-10}$ alkylenyl,
$C_{1-10}$ alkylheteroarylenyl,
heterocyclyl,
heterocyclyl-$C_{1-10}$ alkylenyl, and
$C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino,
$C_{1-10}$ alkylamino, di($C_{1-10}$ alkyl)amino, and in the case of $C_{1-10}$ alkyl, $C_{2-10}$ alkenyl,
$C_{2-10}$ alkynyl, and heterocyclyl, oxo; wherein heteroaryl,
$C_{1-10}$ alkylheteroarylenyl, and heterocyclyl are attached to Z through a carbon atom;
R is selected from the group consisting of alkyl, alkoxy, hydroxy, fluoro, and trifluoromethyl;
n is 0 to 4;
$R_2$ is selected from the group consisting of
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

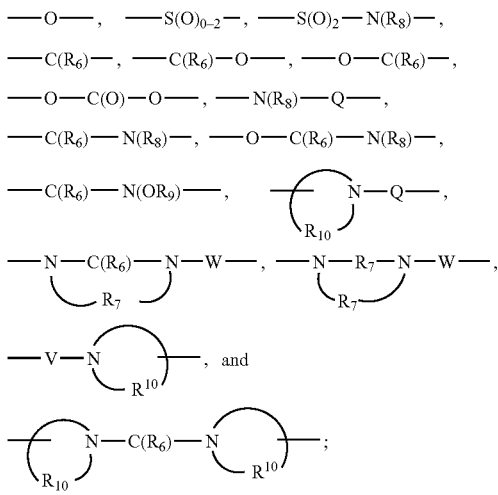

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

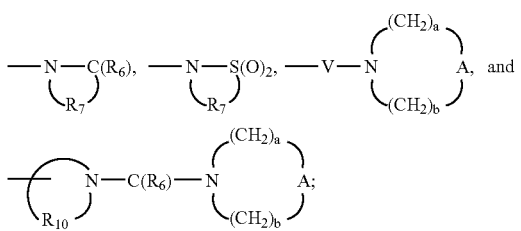

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$;
W is selected from the group consisting of a bond, —C(O)—, and —S(O)$_2$—; and a and b are independently integers from 1 to 6 with the proviso that a+b is ≦7; or a pharmaceutically acceptable salt thereof.

3. A compound of the Formula IIa:

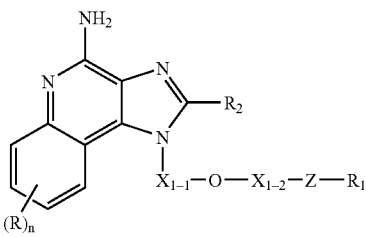

IIa wherein:
X$_{1-1}$ and X$_{1-2}$ are independently selected from the group consisting of C$_{1-10}$ alkylene, C$_{4-10}$ alkenylene, and C$_{4-10}$ alkynylene; wherein the terminal carbon atoms of alkenylene and alkynylene are tetrahedral;
Z is selected from the group consisting of —S—, —S(O)—, and —S(O)$_2$—;
R$_1$ is selected from the group consisting of:
C$_{1-10}$ alkyl,
C$_{2-10}$ alkenyl,
C$_{2-10}$ alkynyl,
aryl,
aryl-C$_{1-10}$ alkylenyl,
aryloxy-C$_{1-10}$ alkylenyl,
C$_{1-10}$ alkylarylenyl,
heteroaryl,
heteroaryl-C$_{1-10}$ alkylenyl,
heteroaryloxy-C$_{1-10}$ alkylenyl,
C$_{1-10}$ alkylheteroarylenyl,
heterocyclyl,
heterocyclyl-C$_{1-10}$ alkylenyl, and
C$_{1-10}$ alkyl, C$_{2-10}$ alkenyl, C$_{2-10}$ alkynyl, aryl, aryl-C$_{1-10}$ alkylenyl, aryloxy-C$_{1-10}$ alkylenyl, C$_{1-10}$ alkylarylenyl, heteroaryl, heteroaryl-C$_{1-10}$ alkylenyl, heteroaryloxy-C$_{1-10}$ alkylenyl, C$_{1-10}$ alkylheteroarylenyl, heterocyclyl, and heterocyclyl-C$_{1-10}$ alkylenyl substituted by one or more substituents independently selected from the group consisting of C$_{1-10}$ alkyl, C$_{1-10}$ alkoxy, hydroxy-C$_{1-10}$ alkyl, halo-C$_{1-10}$ alkyl, halo-C$_{1-10}$ alkoxy, halogen, nitro, hydroxy, cyano, aryl, aryloxy, heteroaryl, heteroaryloxy, heterocyclyl, amino, C$_{1-10}$ alkylamino, di(C$_{1-10}$ alkyl)amino, and in the case of C$_{1-10}$ alkyl, C$_{2-10}$ alkenyl, C$_{2-10}$ alkynyl, and heterocyclyl, oxo; wherein heteroaryl, C$_{1-10}$ alkylheteroarylenyl, and heterocyclyl are attached to Z through a carbon atom;
R is selected from the group consisting of alkyl, alkoxy, hydroxy, fluoro, and trifluoromethyl;
n is 0 to 4;
R$_2$ is selected from the group consisting of
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

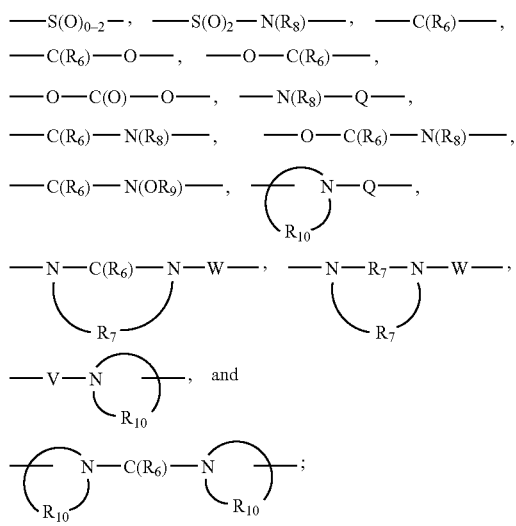

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

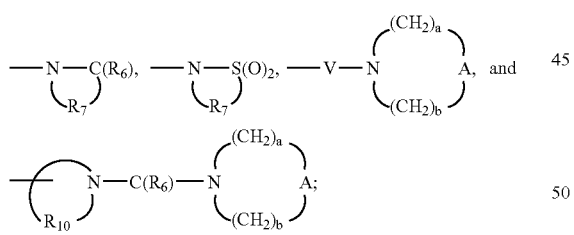

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

4. A compound of the Formula IIIa:

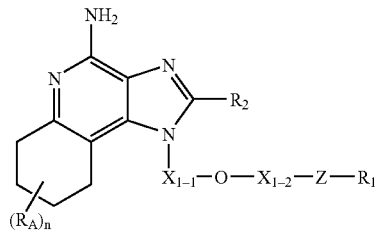

wherein:
$X_{1-1}$ and $X_{1-2}$ are independently selected from the group consisting of $C_{1-10}$ alkylene, $C_{4-10}$ alkenylene, and $C_{4-10}$ alkynylene; wherein the terminal carbon atoms of alkenylene and alkynylene are tetrahedral;
Z is selected from the group consisting of —S—, —S(O)—, and —S(O)$_2$—;
$R_1$ is selected from the group consisting of:
  $C_{1-10}$ alkyl,
  $C_{2-10}$ alkenyl,
  $C_{2-10}$ alkynyl,
  aryl,
  aryl-$C_{1-10}$ alkylenyl,
  aryloxy-$C_{1-10}$ alkylenyl,
  $C_{1-10}$ alkylarylenyl,
  heteroaryl,
  heteroaryl-$C_{1-10}$ alkylenyl,
  heteroaryloxy-$C_{1-10}$ alkylenyl,
  $C_{1-10}$ alkylheteroarylenyl,
  heterocyclyl,
  heterocyclyl-$C_{1-10}$ alkylenyl, and
  $C_{1-10}$ alkyl, $C_{2-10}$ alkenyl, $C_{2-10}$ alkynyl, aryl, aryl-$C_{1-10}$ alkylenyl, aryloxy-$C_{1-10}$ alkylenyl, $C_{1-10}$ alkylarylenyl, heteroaryl, heteroaryl-$C_{1-10}$ alkylenyl, heteroaryloxy-$C_{1-10}$ alkylenyl, $C_{1-10}$ alkylheteroarylenyl, heterocyclyl, and heterocyclyl-$C_{1-10}$ alkylenyl substituted by one or more substituents independently selected from the group consisting of $C_{1-10}$ alkyl, $C_{1-10}$ alkoxy, hydroxy-$C_{1-10}$ alkyl, halo-$C_{1-10}$ alkyl, halo-$C_{1-10}$ alkoxy, halogen, nitro, hydroxy, cyano, aryl, aryloxy, heteroaryl, heteroaryloxy, heterocyclyl, amino,
  $C_{1-10}$ alkylamino, di($C_{1-10}$ alkyl)amino, and in the case of $C_{1-10}$ alkyl, $C_{2-10}$ alkenyl, $C_{2-10}$ alkynyl, and heterocyclyl, oxo; wherein heteroaryl, $C_{1-10}$ alkylheteroarylenyl, and heterocyclyl are attached to Z through a carbon atom;
$R_A$ is selected from the group consisting of:
  halogen,
  hydroxy,
  alkyl,
  alkenyl,
  haloalkyl,
  alkoxy,
  alkylthio, and
  —N(R$_9$)$_2$;
n is 0 to 4;
$R_2$ is selected from the group consisting of
  —R$_4$,
  —X—R$_4$, —X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

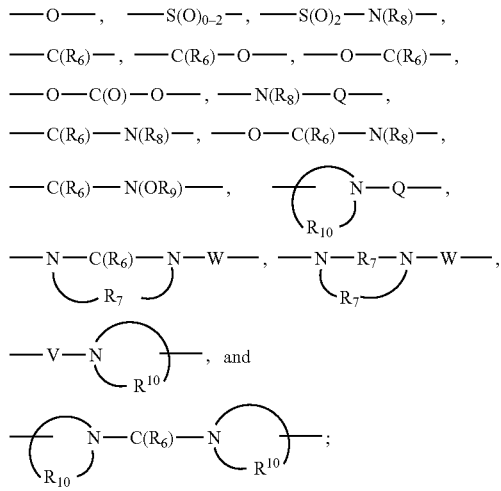

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

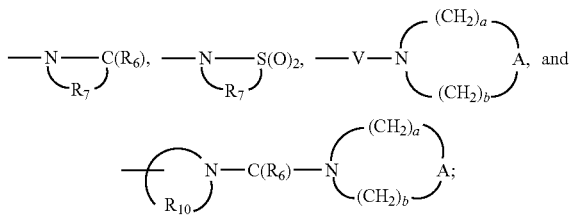

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;

A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

5. A compound of the Formula IIIa:

IIIa

[structure]

wherein:
X$_{1-1}$ and X$_{1-2}$ are independently selected from the group consisting of C$_{1-10}$ alkylene, C$_{4-10}$ alkenylene, and C$_{4-10}$ alkynylene; wherein the terminal carbon atoms of alkenylene and alkynylene are tetrahedral;
Z is selected from the group consisting of —S—, —S(O)—, and —S(O)$_2$—;
R$_1$ is selected from the group consisting of:
  C$_{1-10}$ alkyl,
  C$_{2-10}$ alkenyl,
  C$_{2-10}$ alkynyl,
  aryl,
  aryl-C$_{1-10}$ alkylenyl,
  aryloxy-C$_{1-10}$ alkylenyl,
  C$_{1-10}$ alkylarylenyl,
  heteroaryl,
  heteroaryl-C$_{1-10}$ alkylenyl,
  heteroaryloxy-C$_{1-10}$ alkylenyl,
  C$_{1-10}$ alkylheteroarylenyl,
  heterocyclyl,
  heterocyclyl-C$_{1-10}$ alkylenyl, and
  C$_{1-10}$ alkyl, C$_{2-10}$ alkenyl, C$_{2-10}$ alkynyl, aryl, aryl-C$_{1-10}$ alkylenyl, aryloxy-C$_{1-10}$ alkylenyl, C$_{1-10}$ alkylarylenyl, heteroaryl, heteroaryl-C$_{1-10}$ alkylenyl, heteroaryloxy-C$_{1-10}$ alkylenyl, C$_{1-10}$ alkylheteroarylenyl, heterocyclyl, and heterocyclyl-C$_{1-10}$ alkylenyl substituted by one or more substituents independently selected from the group consisting of C$_{1-10}$ alkyl, C$_{1-10}$ alkoxy, hydroxy-C$_{1-10}$ alkyl, halo-C$_{1-10}$ alkyl, halo-C$_{1-10}$ alkoxy, halogen, nitro, hydroxy, cyano, aryl, aryloxy, heteroaryl, heteroaryloxy, heterocyclyl, amino,
  C$_{1-10}$ alkylamino, di(C$_{1-10}$ alkyl)amino, and in the case of C$_{1-10}$ alkyl, C$_{2-10}$ alkenyl,
  C$_{2-10}$ alkynyl, and heterocyclyl, oxo; wherein heteroaryl,
  C$_{1-10}$ alkylheteroarylenyl, and heterocyclyl are attached to Z through a carbon atom;
R$_A$ is selected from the group consisting of:
  halogen,
  hydroxy,
  alkyl,
  alkenyl, haloalkyl,
alkoxy,
alkylthio, and
—N($R_9$)$_2$;
n is 0 to 4;
$R_2$ is selected from the group consisting of
—$R_4$,
—X—$R_4$,
—X—Y—$R_4$, and
—X—$R_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

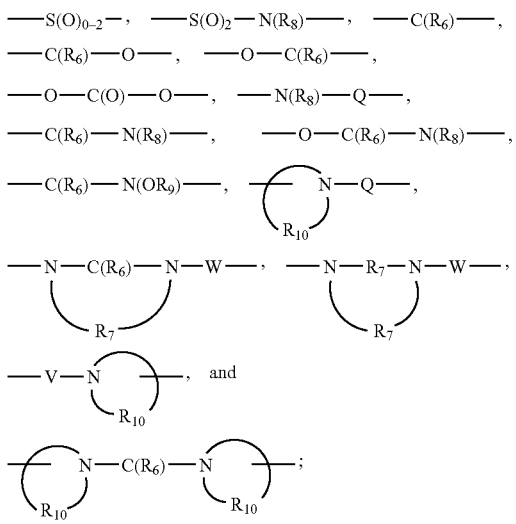

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of:

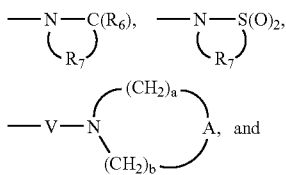

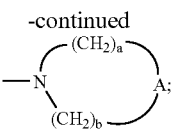

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N($R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

6. The compound or salt of claim 2 wherein n is 0.
7. The compound or salt of claim 1 wherein $R_2$ is hydrogen, alkyl, hydroxyalkylenyl, or alkoxyalkylenyl.
8. The compound or salt of claim 7 wherein $R_2$ is hydrogen, methyl, ethyl, propyl, butyl, 2-hydroxyethyl, hydroxymethyl, 2-methoxyethyl, or ethoxymethyl.
9. The compound or salt of claim 1 wherein Z is —S(O)$_2$—.
10. The compound or salt of claim 1 wherein Z is —S(O)—.
11. The compound or salt of claim 1 wherein Z is —S—.
12. The compound or salt of claim 1 wherein $R_1$ is linear or branched $C_{1-4}$ alkyl, aryl, or 5 to 10 membered heteroaryl containing one or two heteroatoms, wherein the alkyl, aryl, or heteroaryl group may be unsubstituted or substituted with one or more substituents.
13. The compound or salt of claim 12 wherein $R_1$ is methyl, ethyl, 1-propyl, 2-propyl, 2-methylpropyl, 2-hydroxy-2-methylpropyl, phenyl, -4-chlorophenyl, or 4-fluorophenyl.
14. The compound or salt of claim 1 wherein $X_{1-1}$ and $X_{1-2}$ are independently selected from $C_{2-7}$ alkylene groups.
15. The compound or salt of claim 14 wherein $X_{1-1}$ is —(CH$_2$)$_{2-4}$—, —CH$_2$—C(CH$_3$)$_2$—, or —CH$_2$-cyclic (CH$_2$)$_{3-6}$—.
16. The compound or salt of claim 15 wherein $X_{1-2}$ is —(CH$_2$)$_2$— or —(CH$_2$)$_3$—.
17. A pharmaceutical composition comprising a therapeutically effective amount of a compound or salt of claim 1 in combination with a pharmaceutically acceptable carrier.
18. A method of inducing cytokine biosynthesis in an animal comprising administering an effective amount of a compound or salt of claim 1 to the animal.
19. The compound or salt of claim 2 wherein $R_2$ is hydrogen, alkyl, hydroxyalkylenyl, or alkoxyalkylenyl.
20. The compound or salt of claim 19 wherein $R_2$ is hydrogen, methyl, ethyl, propyl, butyl, 2-hydroxyethyl, hydroxymethyl, 2-methoxyethyl, or ethoxymethyl.
21. The compound or salt of claim 2 wherein Z is —S(O)$_2$—.
22. The compound or salt of claim 2 wherein $R_1$ is linear or branched $C_{1-4}$ alkyl, aryl, or 5 to 10 membered heteroaryl containing one or two heteroatoms, wherein the alkyl, aryl, or heteroaryl group may be unsubstituted or substituted with one or more substituents.

23. The compound or salt of claim 22 wherein $R_1$ is methyl, ethyl, 1-propyl, 2-propyl, 2-methylpropyl, 2-hydroxy-2-methylpropyl, phenyl, 4-chlorophenyl, or 4-fluorophenyl.

24. The compound or salt of claim 2 wherein $X_{1-1}$ and $X_{1-2}$ are independently selected from $C_{2-7}$ alkylene groups.

25. The compound or salt of claim 24 wherein $X_{1-1}$ is —$(CH_2)_{2-4}$—, —$CH_2$—$C(CH_3)_2$—, or —$CH_2$-cyclic $(CH_2)_{3-6}$—.

26. The compound or salt of claim 25 wherein $X_{1-2}$ is —$(CH_2)_2$— or —$(CH_2)_3$—.

27. The compound or salt of claim 4 wherein n is 0.

28. The compound or salt of claim 4 wherein $R_2$ is hydrogen, alkyl, hydroxyalkylenyl, or alkoxyalkylenyl.

29. The compound or salt of claim 28 wherein $R_2$ is hydrogen, methyl, ethyl, propyl, butyl, 2-hydroxyethyl, hydroxymethyl, 2-methoxyethyl, or ethoxymethyl.

30. The compound or salt of claim 4 wherein Z is —$S(O)_2$—.

31. The compound or salt of claim 4 wherein $R_1$ is linear or branched $C_{1-4}$ alkyl, aryl, or 5 to 10 membered heteroaryl containing one or two heteroatoms, wherein the alkyl, aryl, or heteroaryl group may be unsubstituted or substituted with one or more substituents.

32. The compound or salt of claim 31 wherein $R_1$ is methyl, ethyl, 1-propyl, 2-propyl, 2-methylpropyl, 2-hydroxy-2-methylpropyl, phenyl, 4-chlorophenyl, or 4-fluorophenyl.

33. The compound or salt of claim 4 wherein $X_{1-1}$ and $X_{1-2}$ are independently selected from $C_{2-7}$ alkylene groups.

34. The compound or salt of claim 33 wherein $X_{1-1}$ is —$(CH_2)_{2-4}$—, —$CH_2$—$C(CH_3)_2$—, or —$CH_2$-cyclic $(CH_2)_{3-6}$—.

35. The compound or salt of claim 34 wherein $X_{1-2}$ is —$(CH_2)_2$— or —$(CH_2)_3$—.

36. A pharmaceutical composition comprising a therapeutically effective amount of a compound or salt of claim 2 in combination with a pharmaceutically acceptable carrier.

37. A method of inducing cytokine biosynthesis in an animal comprising administering an effective amount of a compound or salt of claim 2 to the animal.

38. A pharmaceutical composition comprising a therapeutically effective amount of a compound or salt of claim 4 in combination with a pharmaceutically acceptable carrier.

39. A method of inducing cytokine biosynthesis in an animal comprising administering an effective amount of a compound or salt of claim 4 to the animal.

\* \* \* \* \*

UNITED STATES PATENT AND TRADEMARK OFFICE
CERTIFICATE OF CORRECTION

PATENT NO. : 7,939,526 B2
APPLICATION NO. : 10/596117
DATED : May 10, 2011
INVENTOR(S) : Matt R Radmer et al.

It is certified that error appears in the above-identified patent and that said Letters Patent is hereby corrected as shown below:

List of References

- Page 1, Col. 2 (Other Publications), Lines 4-6 - After "1983." delete "Brennan at al., "Automated Bioassay of Interferons in Micro-test Plates.", Biotechniques, Jun./Jul., 78, 1983." and insert the same on First Page, Col. 2, Line 5, as a new entry.

- Page 1, Col. 2(Other Publications), Line 4 - Delete "at al." and insert -- et al. --, therefor.

- Page 2, Col. 1(Other Publications), Line 4 - Delete "Rice et al." and insert -- Coleman, et al. --, therefor.

Specification

- Col. 5, Line 7 - Delete "–(O)$_2$–;" and insert -- –S(O)$_2$–; --, therefor.

- Col. 7, Line 63 - Delete "–(O)$_2$–;" and insert -- –S(O)$_2$–; --, therefor.

- Col. 13, Line 42 - Delete "alynyl," and insert -- alkynyl, --, therefor.

- Col. 21, Line 15 - Delete "–(O)$_2$–;" and insert -- –S(O)$_2$–; --, therefor.

- Col. 25, Line 8 - Before "alkoxy," delete "to".

- Col. 29, Line 9 - Delete "allyl," and insert -- alkyl, -- therefor.

- Col. 29, Line 41 - Delete "–(O)$_2$–;" and insert -- –S(O)$_2$–; --, therefor.

- Col. 29, Line 62 - Delete "$C_{1-10}$" and insert -- $C_{4-10}$ --, therefor.

Signed and Sealed this
Thirteenth Day of March, 2012

David J. Kappos
*Director of the United States Patent and Trademark Office*

CERTIFICATE OF CORRECTION (continued)  Page 2 of 4
U.S. Pat. No. 7,939,526 B2

Specification Cont'd

- Col. 30, Line 13 - Below "consisting of:" insert -- –(O)–; --.

- Col. 31, Line 21 - Delete "substitutent." and insert -- substituent. --, therefor.

- Col. 35, Line 67 - After "of" insert -- –(O)–, --.

- Col. 36, Line 67 - Delete "oxo.-" and insert -- oxo. --, therefor.

- Col. 37, Line 39 - After "Ia," insert -- II, --.

- Col. 38, Line 55 - Delete "VI." and insert -- VIII. --, therefor.

- Col. 39, Line 8 - Delete "L" and insert -- I, --, therefor.

- Col. 39, Line 16 to Col. 40 Line 9 - Delete "In step (4b) an N-oxide of Formula IX is aminated to provide a 1$H$-imidazo[4,5-$c$]quinolin-4-amine of Formula IIa-1, which is a subgenus of Formula I, Ia, II, IIa, and IIb. The reaction is carried out in two parts. In part (i) a compound of Formula IX is reacted with an acylating agent. Suitable acylating agents include alkyl- or arylsulfonyl chorides (e.g., benesulfonyl chloride). In part (ii) the product of part (i) is reacted with an excess of an aminating agent. Suitable animenzenesulfonyl choride, methanesulfonyl choride, or p-toluating agents include ammonia (e.g. in the form of ammonium hydroxide) and ammonium salts (e.g., ammonium carenesulfonyl chloride). In part (ii) the product of part (i) is reacted with an excess of an aminating agent. Suitable animbonate, ammonium bicarbonate, ammonium phosphate). The reaction can be carried out by dissolving a compound of Formula IX in a suitable solvent such as dichloromethane or chlorofonn, adding ammonium hydroxide to the solution, and then adding p-toluenesulfonyl chloride. The product or a pharmaceutically acceptable salt thereof can be isolated using conventional methods."

and insert -- In step (4b) an N-oxide of Formula IX is aminated to provide a 1$H$-imidazo[4,5-$c$]quinolin-4-amine of Formula IIa-1, which is a subgenus of Formulas I, Ia, II, IIa, and IIb. The reaction is carried out in two parts. In part (i) a compound of Formula IX is reacted with an acylating agent. Suitable acylating agents include alkyl- or arylsulfonyl chlorides (e.g., benzenesulfonyl chloride, methanesulfonyl chloride, or $p$-toluenesulfonyl chloride). In part (ii) the product of part (i) is reacted with an excess of an aminating agent. Suitable aminating agents include ammonia (e.g. in the form of ammonium hydroxide) and ammonium salts (e.g., ammonium carbonate, ammonium bicarbonate, ammonium phosphate). The reaction can be carried out by dissolving a compound of Formula IX in a suitable solvent such as dichloromethane or chloroform, adding ammonium hydroxide to the solution, and then adding $p$-toluenesulfonyl chloride. The product or a pharmaceutically acceptable salt thereof can be isolated using conventional methods. --, therefor.

- Col. 41, Line 1 - Delete "4 amines" and insert -- 4-amines --, therefor.

CERTIFICATE OF CORRECTION (continued)

Specification Cont'd

- Col. 42, Line 63 - Delete "substitutents." and insert -- substituents. --, therefor.

- Col. 44, Line 11 - Delete "hydroxpropoxy" and insert -- hydroxypropoxy --, therefor.

- Col. 44, Line 29 - Delete "XXI." and insert -- XXII. --, therefor.

- Col. 44, Line 48 - Delete "XXV" and insert -- XXIV --, therefor.

- Col. 51, Line 10 - Delete "VII" and insert -- I --, therefor.

- Col. 55, Line 32 - Delete "papillomavirises," and insert -- papillomaviruses, --, therefor.

- Col. 55, Line 58 - Delete "myelogeous" and insert -- myelogenous --, therefor.

- Col. 55, Line 67 - Delete "greata;" and insert -- areata; --, therefor.

- Col. 56, Line 18 - Delete "hemophilus" and insert -- haemophilus --, therefor.

- Col. 59, Line 39 - Delete "(72 µL)." and insert -- (72 mL). --, therefor.

- Col. 59, Lines 61 - Delete "(50 ml)," and insert -- (50 mL), --, therefor.

- Col. 61, Line 8 - Delete "S. 0.25" and insert -- S.0.25 --, therefor.

- Col. 63, Line 3 - Delete "(M+1)$^+$;" and insert -- (M+H)$^+$ --, therefor.

- Col. 66, Line 4 - Delete "60%" and insert-- ~60% --, therefor.

- Col. 68, Line 13 - Delete "(M+" and insert -- (M+H)$^+$; --, therefor.

- Col. 70, Line 56 - Delete "[(3-nitroquinolinyl)" and insert -- [(3-nitroquinolin-4-yl) --, therefor.

- Col. 73, Line 34 - After "13.39" insert -- . --.

- Col. 75, Lines 28-35 - Delete "mp 150.0-151.0° C. $^1$H NMR (300 MHz, DMSO) δ 8.72 (d, J=4.7 Hz, 1H), 8.13 (t, J=7.8 Hz, 1H), 7.97-8.01 (m, 2H), 7.71-7.73 (m, 1H), 7.58 (d, J=7.3 Hz, 1H), 7.37 (t, J=8.2 Hz, 1H), 7.17 (t, J=7.0 Hz, 1H), 6.38 (s, 2H), 4.67 (t, J=5.2 Hz, 2H), 3.76 (t, J=5.2 Hz, 2H), 3.28-3.38 (m, 4H), 2.86 (t, J=7.6 Hz, 2H), 1.82 (apparent hextet, J=7.6, 7.4, 7.3 Hz, 2H), 1.69-1.71 (m, 2H), 0.99 (t, J=7.4 Hz, 3H); MS (APCI) m/z 454 (M+H)$^+$; Anal. calcd for $C_{23}H_{27}N_5O_3S$: C, 60.91; H, 6.00; N, 15.44. Found: C, 60.59; H, 5.91; N, 15.32." and insert the same on Col. 75, Line 27, after "powder," as the continuation of the same paragraph.

Specification Cont'd

- Col. 75, Line 61 - Delete "3.5g" and insert -- ~3.5g --, therefor.

- Col. 76, Line 9 - Delete "[3-(ethylsulfinyl)" and insert -- [3-(Methylsulfinyl) --, therefor.

- Col. 76, Line 43 - Delete "pentet," and insert -- (pentet, --, therefor.

- Col. 83, Line 46 - Delete "(M+H);" and insert -- (M+H)$^+$; --, therefor.

- Col. 84, Lines 34 - Delete "quinolin amine" and insert -- quinolin-4-amine --, therefor.

- Col. 91, Line 63 - Delete "3.60," and insert -- 3.60 --, therefor.

- Col. 91, Line 67 - Delete "(M+H);" and insert -- (M+H)$^+$; --, therefor.

- Col. 92, Line 29 - After "Russ." delete "i".

- Col. 100, Line 23 - Delete "41~48" and insert -- 41-48 --, therefor.

- Col. 101, Line 2 - Delete "Examples" and insert -- The examples --, therefor.

- Col. 101, Lines 56-60 - Delete "methyethyl" and insert -- methylethyl --, therefor.

- Col. 102, Lines 23-28 - Delete "methyethyl" and insert -- methylethyl --, therefor.

- Col. 102, Lines 42-47 - Delete "methyethyl" and insert -- methylethyl --, therefor.

- Col. 102, Lines 62-66 - Delete "methyethyl" and insert -- methylethyl --, therefor.